(12) United States Patent
Straubinger et al.

(10) Patent No.: US 9,138,315 B2
(45) Date of Patent: Sep. 22, 2015

(54) MEDICAL DEVICE FOR TREATING A HEART VALVE INSUFFICIENCY OR STENOSIS

(75) Inventors: Helmut Straubinger, Aschheim (DE); Johannes Jung, Karlsruhe (DE)

(73) Assignee: JENAVALVE TECHNOLOGY GMBH, Munich (DE)

( * ) Notice: Subject to any disclaimer, the term of this patent is extended or adjusted under 35 U.S.C. 154(b) by 866 days.

(21) Appl. No.: 11/812,095

(22) Filed: Jun. 14, 2007

(65) Prior Publication Data

US 2008/0255661 A1    Oct. 16, 2008

Related U.S. Application Data

(63) Continuation of application No. 11/785,072, filed on Apr. 13, 2007, now Pat. No. 7,896,915.

(30) Foreign Application Priority Data

May 15, 2007    (EP) .................................... 07009728

(51) Int. Cl.
    *A61F 2/24*    (2006.01)
    *A61F 2/95*    (2013.01)
(52) U.S. Cl.
    CPC ............ *A61F 2/2436* (2013.01); *A61F 2/2427* (2013.01); *A61F 2/2418* (2013.01); *A61F 2002/9517* (2013.01)
(58) Field of Classification Search
    CPC ... A61F 2/2427; A61F 2/2436; A61F 2/2418; A61F 2/2409; A61F 2/95; A61F 2/962; A61F 2002/9665
    USPC ................... 623/1.11, 1.12, 2.11, 2.14, 2.17; 606/108
    See application file for complete search history.

(56) References Cited

U.S. PATENT DOCUMENTS 4,950,227 A  * 8/1990 Savin et al. .................. 623/1.12
5,002,566 A    3/1991 Carpentier et al.
(Continued)

FOREIGN PATENT DOCUMENTS

AU    2006308187 A1    5/2007
AU    2006310681 A1    5/2007
(Continued)

OTHER PUBLICATIONS

File history for German Patent DE 195 46 692 filed Dec. 14, 1995 and patented Jul. 11, 2002.
(Continued)

*Primary Examiner* — Julian W Woo
*Assistant Examiner* — Christopher L Templeton
(74) *Attorney, Agent, or Firm* — Bookoff McAndrews, PLLC

(57) ABSTRACT

A medical device for treating a heart valve insufficiency, with an endoprosthesis which can be introduced into a patient's body and expanded to secure a heart valve prosthesis in the patient's aorta with a catheter. In an embodiment, the endoprosthesis has a plurality of positioning arches configured to be positioned with respect to a patient's aorta and a plurality of retaining arches to support a heart valve prosthesis. The endoprosthesis includes a collapsed mode during the process of introducing it into the patient's body and an expanded mode when it is implanted. The endoprosthesis may be introduced into a patient's body and expanded via a catheter. In an embodiment, the catheter has first and second slide mechanisms configured to independently manipulate first and second sleeve elements to sequentially expand the endoprosthesis from the collapsed mode to the expanded mode.

38 Claims, 59 Drawing Sheets

(56) References Cited

U.S. PATENT DOCUMENTS

| | | |
|---|---|---|
| 5,061,277 A | 10/1991 | Carpentier et al. |
| 5,094,661 A | 3/1992 | Levy et al. |
| 5,104,407 A | 4/1992 | Lam et al. |
| 5,167,628 A | 12/1992 | Boyles |
| 5,197,979 A | 3/1993 | Quintero et al. |
| 5,201,757 A * | 4/1993 | Heyn et al. .................... 606/198 |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,433,723 A * | 7/1995 | Lindenberg et al. .......... 606/198 |
| 5,456,713 A | 10/1995 | Chuter |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 5,984,964 A | 11/1999 | Roberts et al. |
| 6,001,126 A | 12/1999 | Nguyen-Thien-Nhon |
| 5,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,143,021 A * | 11/2000 | Staehle .................... 623/1.11 |
| 6,146,415 A * | 11/2000 | Fitz .................... 623/1.11 |
| 6,168,614 B1 | 1/2001 | Andersen et al. |
| 6,177,514 B1 | 1/2001 | Pathak et al. |
| 6,183,481 B1 | 2/2001 | Lee et al. |
| 6,190,393 B1 * | 2/2001 | Bevier et al. .................... 606/108 |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,267,783 B1 * | 7/2001 | Letendre et al. .................... 623/1.13 |
| 6,283,995 B1 | 9/2001 | Moe et al. |
| 6,287,338 B1 | 9/2001 | Sarnowski et al. |
| 6,287,339 B1 | 9/2001 | Vazquez et al. |
| 6,312,465 B1 | 11/2001 | Griffin et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,365 B1 * | 4/2002 | Diaz .................... 606/108 |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,562,063 B1 * | 5/2003 | Euteneuer et al. ........... 623/1.12 |
| 6,572,642 B2 | 6/2003 | Rinaldi et al. |
| 6,582,460 B1 * | 6/2003 | Cryer .................... 623/1.11 |
| 6,582,462 B1 | 6/2003 | Andersen et al. |
| 6,585,766 B1 | 7/2003 | Huynh et al. |
| 6,613,086 B1 | 9/2003 | Moe et al. |
| 6,673,101 B1 * | 1/2004 | Fitzgerald et al. ........... 623/1.11 |
| 6,673,106 B2 * | 1/2004 | Mitelberg et al. .............. 623/1.2 |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 2,121,182 A1 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,849,084 B2 * | 2/2005 | Rabkin et al. ................ 623/1.12 |
| 6,860,898 B2 | 3/2005 | Stack et al. |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,939,370 B2 | 9/2005 | Hartley et al. |
| 6,945,997 B2 | 9/2005 | Huynh et al. |
| 6,964,676 B1 * | 11/2005 | Gerberding et al. ......... 623/1.11 |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,074,236 B2 * | 7/2006 | Rabkin et al. ................ 623/1.12 |
| 7,078,163 B2 | 7/2006 | Torrianni |
| 7,081,132 B2 | 7/2006 | Cook et al. |
| 7,137,184 B2 | 11/2006 | Schreck |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,258,891 B2 * | 8/2007 | Pacetti et al. ................. 427/2.24 |
| 7,264,632 B2 * | 9/2007 | Wright et al. ................ 623/1.12 |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 7,553,324 B2 * | 6/2009 | Andreas et al. .............. 623/1.12 |
| 7,608,099 B2 * | 10/2009 | Johnson et al. .............. 623/1.11 |
| 7,655,034 B2 * | 2/2010 | Mitchell et al. .............. 623/1.15 |
| 7,771,463 B2 * | 8/2010 | Ton et al. .................... 623/1.11 |
| 7,794,487 B2 * | 9/2010 | Majercak et al. ............ 623/1.11 |
| 8,147,534 B2 * | 4/2012 | Berez et al. .................... 623/1.11 |
| 2001/0011187 A1 | 8/2001 | Pavcnik et al. |
| 2001/0039450 A1 | 11/2001 | Pavcnik et al. |
| 2001/0051822 A1 * | 12/2001 | Stack et al. .................... 623/1.11 |
| 2002/0032481 A1 | 3/2002 | Gabbay |
| 2002/0055775 A1 | 5/2002 | Carpentier et al. |
| 2002/0120323 A1 * | 8/2002 | Thompson et al. ........... 623/1.11 |
| 2002/0123790 A1 | 9/2002 | White et al. |
| 2002/0133226 A1 | 9/2002 | Marquez et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |

(56) References Cited

U.S. PATENT DOCUMENTS

| | | |
|---|---|---|
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0212410 A1* | 11/2003 | Stenzel et al. ............ 606/108 |
| 2003/0236570 A1 | 12/2003 | Cook et al. |
| 2004/0006380 A1 | 1/2004 | Buck et al. |
| 2004/0015228 A1* | 1/2004 | Lombardi et al. .......... 623/1.18 |
| 2004/0039436 A1 | 2/2004 | Spenser et al. |
| 2004/0049204 A1* | 3/2004 | Harari et al. ............... 606/108 |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0093063 A1* | 5/2004 | Wright et al. ............... 623/1.12 |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193180 A1* | 9/2004 | Buzzard et al. ............ 606/108 |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149159 A1 | 7/2005 | Andreas et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222664 A1 | 10/2005 | Parker |
| 2005/0222668 A1 | 10/2005 | Schaeffer et al. |
| 2005/0234546 A1 | 10/2005 | Nugent et al. |
| 2005/0251243 A1* | 11/2005 | Seppala et al. ............. 623/1.11 |
| 2005/0251251 A1* | 11/2005 | Cribier ....................... 623/2.11 |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0058872 A1 | 3/2006 | Salahieh et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0229718 A1 | 10/2006 | Marquez |
| 2006/0229719 A1 | 10/2006 | Marquez et al. |
| 2006/0246584 A1 | 11/2006 | Covelli |
| 2006/0253191 A1 | 11/2006 | Salahieh et al. |
| 2006/0259134 A1 | 11/2006 | Schwammenthal et al. |
| 2006/0259136 A1 | 11/2006 | Nguyen et al. |
| 2006/0265056 A1 | 11/2006 | Nguyen et al. |
| 2006/0276873 A1 | 12/2006 | Sato |
| 2006/0276874 A1 | 12/2006 | Wilson et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0078504 A1 | 4/2007 | Mialhe |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0233222 A1* | 10/2007 | Roeder et al. ............. 623/1.11 |
| 2007/0239271 A1 | 10/2007 | Nguyen |
| 2007/0244551 A1 | 10/2007 | Stobie |
| 2007/0255386 A1* | 11/2007 | Tenne .......................... 623/1.11 |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0039925 A1* | 2/2008 | Ishimaru et al. ............ 623/1.12 |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0147182 A1* | 6/2008 | Righini et al. ............. 623/2.11 |
| 2008/0154355 A1 | 6/2008 | Benichou et al. |
| 2008/0172119 A1* | 7/2008 | Yamasaki et al. ............ 623/1.11 |
| 2008/0200977 A1 | 8/2008 | Paul et al. |
| 2008/0215143 A1 | 9/2008 | Seguin |
| 2008/0255660 A1 | 10/2008 | Guyenot et al. |
| 2008/0262590 A1 | 10/2008 | Murray |
| 2008/0262602 A1 | 10/2008 | Wilk et al. |
| 2008/0269878 A1 | 10/2008 | Iobbi |
| 2008/0275549 A1 | 11/2008 | Rowe |
| 2009/0005863 A1 | 1/2009 | Goetz et al. |

(56) References Cited

U.S. PATENT DOCUMENTS

| | | | |
|---|---|---|---|
| 2009/0112309 A1* | 4/2009 | Jaramillo et al. | 623/1.26 |
| 2009/0234443 A1 | 9/2009 | Ottma et al. | |
| 2010/0137979 A1* | 6/2010 | Tuval et al. | 623/2.11 |

FOREIGN PATENT DOCUMENTS

| | | |
|---|---|---|
| CA | 2436258 A1 | 1/2005 |
| CA | 2595233 | 7/2006 |
| CA | 2627555 | 5/2007 |
| DE | 195 46 692 A1 | 6/1997 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 A1 | 5/2007 |
| DE | 10 2005 052628 A1 | 5/2007 |
| DE | 202007005491 U1 | 7/2007 |
| EP | 0084395 A1 | 7/1983 |
| EP | 0458877 | 8/1990 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0871414 | 9/1995 |
| EP | 0 592 410 B1 | 10/1995 |
| EP | 0756498 | 10/1995 |
| EP | 0 592 410 B1 | 11/1995 |
| EP | 0786970 | 5/1996 |
| EP | 0729364 B1 | 9/1996 |
| EP | 0756498 B1 | 5/1997 |
| EP | 0778775 B1 | 6/1997 |
| EP | 0786970 | 8/1997 |
| EP | 0888142 | 9/1997 |
| EP | 0971649 | 10/1998 |
| EP | 0928615 A1 | 7/1999 |
| EP | 1051204 | 7/1999 |
| EP | 1089676 | 12/1999 |
| EP | 0986348 B1 | 3/2000 |
| EP | 1117446 | 4/2000 |
| EP | 1 164 976 | 8/2000 |
| EP | 1158937 | 9/2000 |
| EP | 1 251 805 B1 | 10/2000 |
| EP | 1041942 B1 | 10/2000 |
| EP | 1041943 B1 | 10/2000 |
| EP | 1171061 | 10/2000 |
| EP | 1206179 | 2/2001 |
| EP | 1 233 731 | 5/2001 |
| EP | 1117446 B1 | 7/2001 |
| EP | 1 255 510 | 8/2001 |
| EP | 1259193 | 9/2001 |
| EP | 1 233 731 B1 | 5/2002 |
| EP | 1 330 213 | 5/2002 |
| EP | 1206179 B1 | 5/2002 |
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |
| EP | 1281375 A2 | 2/2003 |
| EP | 1408882 | 2/2003 |
| EP | 1 435 878 | 4/2003 |
| EP | 1 435 879 | 4/2003 |
| EP | 1 441 672 | 6/2003 |
| EP | 1 017 868 B1 | 9/2003 |
| EP | 1354569 A1 | 10/2003 |
| EP | 1494616 | 10/2003 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 663 070 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1469797 B1 | 11/2005 |
| EP | 1835948 | 6/2006 |
| EP | 1863545 | 9/2006 |
| EP | 1893132 | 11/2006 |
| EP | 1901681 | 12/2006 |
| EP | 1 255 510 B1 | 3/2007 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 2003-523262 | 8/2003 |
| JP | 2003-524504 | 8/2003 |
| JP | 2005-118585 | 5/2005 |
| JP | 2007-296375 | 11/2007 |
| JP | 2008539305 | 11/2008 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO 98/43556 | 10/1998 |
| WO | WO-98/46165 | 10/1998 |
| WO | WO-99/37337 | 7/1999 |
| WO | WO-99/66863 | 12/1999 |
| WO | WO 00/15148 | 3/2000 |
| WO | WO-00/18445 | 4/2000 |
| WO | WO 00/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 01/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 02/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |

(56) References Cited

FOREIGN PATENT DOCUMENTS

| WO | WO 03/028592 A1 | 4/2003 |
|---|---|---|
| WO | WO 03/047468 A1 | 6/2003 |
| WO | WO-03/079928 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/051620 A1 | 5/2007 |
| WO | WO 2007/059252 A1 | 5/2007 |
| WO | WO-2007/071436 A | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2006/076890 | 7/2008 |
| WO | WO 2008/079962 A1 | 7/2008 |
| WO | WO 2008/101083 A2 | 8/2008 |
| WO | WO 2008/125153 A1 | 10/2008 |
| WO | WO 2008/138584 A1 | 11/2008 |

OTHER PUBLICATIONS

Aortenklappenbioprothese erfolgreich in der Entwicklung, (1 page) May 16, 2003.

Translation of Aortenklappenbioprothese erfolgreich in der Entwicklung (2 pages).

Screen shots from http://www.fraunhofer.de/presse/filme/2006/index.jsp (2 pages), 2006.

Liang, Ma, et al., "Double-crowned valved stents for off-pump mitral valve replacement," European Journal of Cardio-Thoracic Surgery, 194-198 (5 pages), Jun. 13, 2005.

Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.

Translation of DE 19546692 A1 (4 pages).

Translation of EP 1469797 B1 (16 pages).

U.S. Appl. No. 12/084,421, filed May 1, 2008.

Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).

Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).

Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

\* cited by examiner

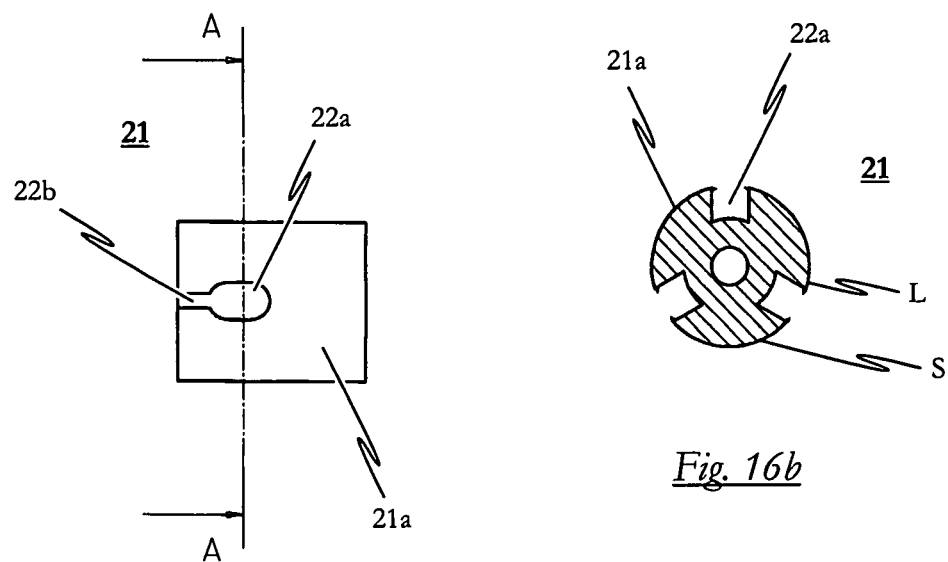
Fig. 16a
Fig. 16b
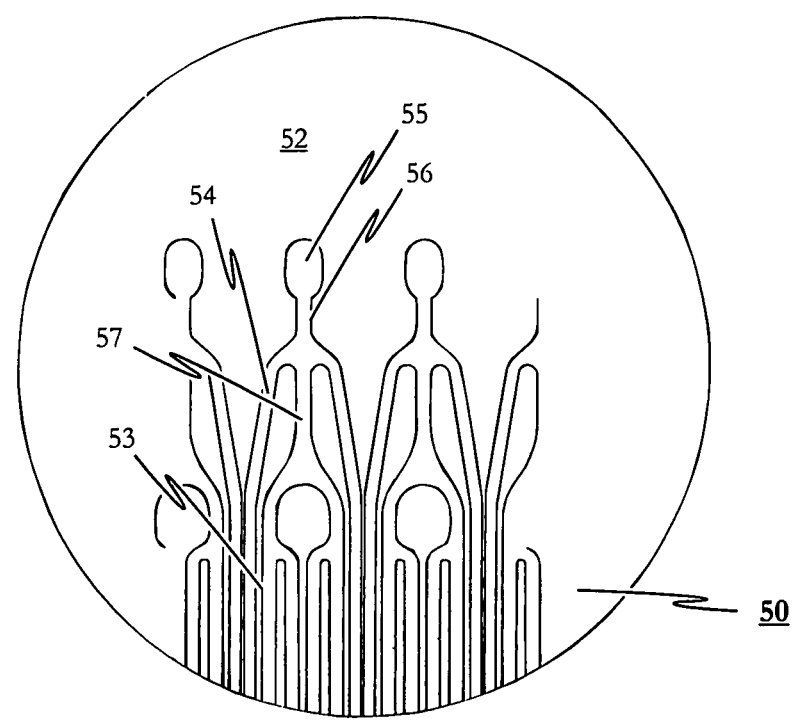
Fig. 16c

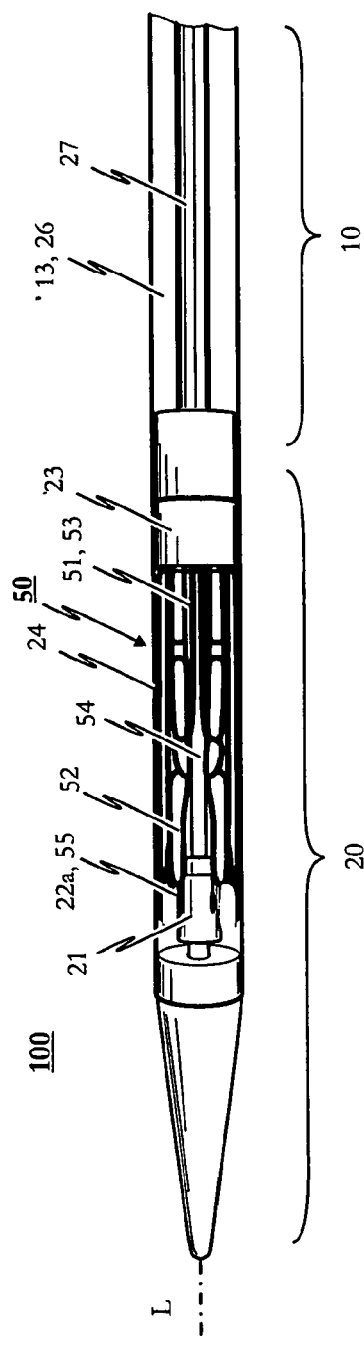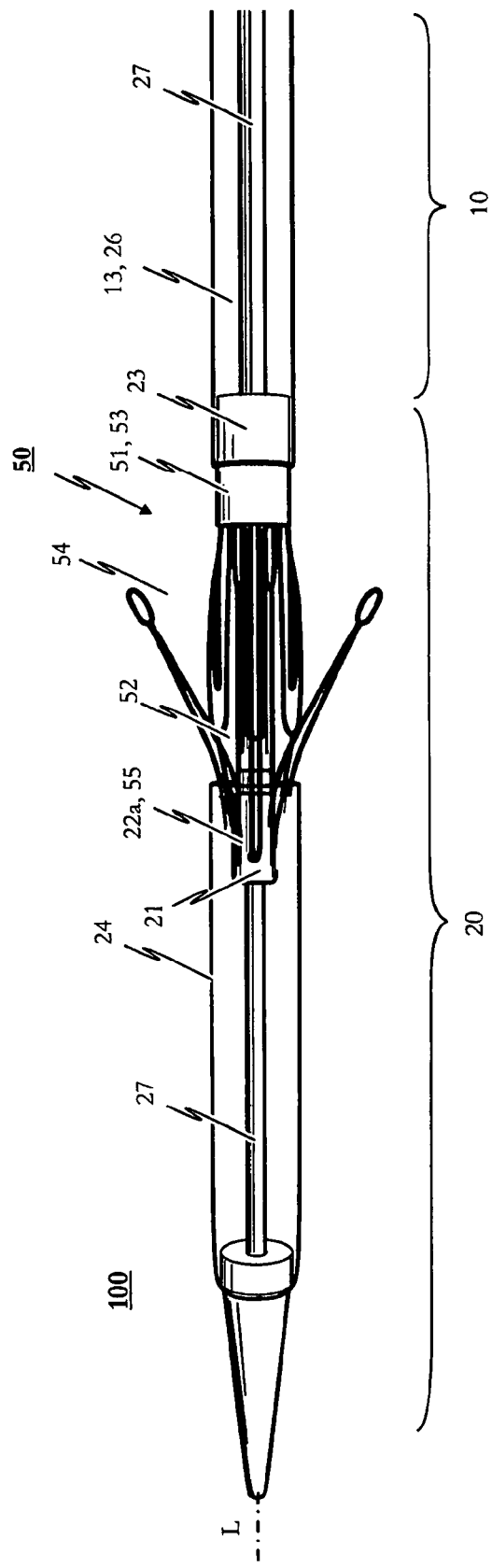
Fig. 17a
Fig. 17b

MEDICAL DEVICE FOR TREATING A HEART VALVE INSUFFICIENCY OR STENOSIS

This is a continuation-in-part application of U.S. application Ser. No. 11/785,072 filed Apr. 13, 2007, now U.S. Pat. No. 7,896,915.

FIELD OF INVENTION

This invention relates to a medical device for treating a heart valve insufficiency or stenosis. The medical device includes an endoprosthesis which can be introduced into a patient's body with minimal invasion and automatically expanded to position and secure a heart valve prosthesis in the patient's aorta.

BACKGROUND OF INVENTION

The expression "narrowing of a heart valve and/or heart valve insufficiency" is intended to include a functional defect of one or more heart valves which is either genetic or has developed over time due to age or disease. A valve defect of this type might affect each of the four coronary valves, although the valves in the left ventricle (aortal and mitral valves) are affected much more often than the right-hand part of the heart (pulmonary and tricuspid valves). The functional defect can result in narrowing (stenosis), inability to close (insufficiency) or a combination of the two (combined vitium).

The operating principle of medical devices for treating a heart valve insufficiency or stenosis is already generally known in the field of medical technology. Biological or mechanical valve models are currently available as a means for replacing human heart valves. Replacement valves are typically stitched to the base of the native heart valve once the diseased valve has been removed. The procedure requires an opening to be made in the thorax to undertake this intervention, the patient's circulation must be supported by a heart and lung machine and the heart arrested whilst the heart valve prosthesis is implanted. This is a risky surgical intervention which places the patient at considerable risk and involves a long post-operative phase of treatment. In multi-morbid patients in particular, the risk of carrying out such intervention is rarely justifiable.

In more recent times, minimally invasive treatment methods have been developed which are distinctive due to the fact that the intervention can be carried out with a local anaesthetic. This option is based on the use of a self-expanding stent carrying a collapsible heart valve prosthesis which is implanted into the human body by means of an appropriate catheter system. A self-expanding heart valve endoprosthesis of this type can be fed by means of a catheter system through a main artery or vein to the implantation site at the heart. Once the implantation site is reached, the endoprosthesis, such as a stent, is successively unfolded. Once unfolded, the heart valve endoprosthesis can be anchored in the blood vessel, for example, with the assistance of anchoring hooks. The actual heart valve prosthesis is disposed directly in the proximal region of the stent or endoprosthesis.

Patent publication DE 100 10 074 A1 discloses a device for securing and anchoring heart valve prostheses which essentially comprises shaped wire elements connected to one another. Different arches are used as a means of reliably securing and anchoring the heart valve prosthesis. To this end, the device described in this specification has three identical pairs of arches respectively disposed at a distance of 120° apart. These arches are connected to one another by fixed body joints which assume the function of pivot bearings. Arches bent in the opposite direction are also provided, forming lever arms which are of identical length as far as possible, to enable a reliable seating of the arches, even in the event of peristaltic movements of the heart and blood vessel, and afford a reliable seal for an implanted and secured heart valve prosthesis.

With the known solutions there is still a risk of heart valves being incorrectly implanted. In particular, the heart valve prosthesis must be exactly positioned and longitudinally oriented. This requires enormous skill on the part of the surgeon performing the treatment to position a stent carrying a heart valve prosthesis at its proximal end accurately enough in the vicinity of the patient's diseased heart valve to ensure both correct lateral and longitudinal positioning of the heart valve prosthesis.

Amongst other things, incorrect or sub-optimal implantation and positioning of a heart valve prosthesis can lead to inadequate sealing or valve insufficiency which places considerable stress on the ventricle. For example, if a heart valve prosthesis is implanted too far above the actual heart valve plane, this can reduce or even cover and block the outlets of the coronary vessels (coronaries) leading to fatal coronary ischaemia due to heart infarction. Thus, it is absolutely vital that the requirements of both lateral and longitudinal positioning accuracy of a heart valve prosthesis are met.

In the case of conventional minimally invasive implantation techniques where self-expandable heart valve prostheses are introduced to the implantation site at or in the heart through a main artery of the patient, the prosthesis is usually introduced by means of a guide wire and with the aid of catheters. In such a case it is standard practice to use a balloon catheter to expand and open the native heart valves to allow insertion of a catheter. Although it is possible to monitor and control the introduction process during such an intervention, for example with the aid of an X-ray system (heart catheter laboratory=HCL) or with the aid of ultrasound (trans-oesophageal echocardiogram=TEE), the heart valve prosthesis is still of relatively large dimensions in spite of being minimised whilst it is being introduced. It is often not possible to obtain the required positioning accuracy due to restricted ability to manoeuvre, and in particular to ensure correct longitudinal positioning, of the heart valve prosthesis to be implanted with the fixing elements attached to it. If there is a risk that the coronary vessels might close, implanting the heart valve prosthesis in a position angularly offset from the optimum implantation site represents a particular risk for the patient.

When designing a heart valve prosthesis, allowance must specifically be made for the considerable forces which act on the prosthesis, including during the filling phase of the heart cycle (diastole). Reliable anchoring is necessary to prevent the implanted heart valve prosthesis from becoming detached or moving in any direction.

Accordingly, it must be possible to manoeuvre the heart valve prosthesis in the relevant access vessel as efficiently as possible during the implantation process to ensure optimum positioning accuracy on the one hand and, on the other hand, the implanted heart valve prosthesis must be firmly anchored at the implantation site effectively to prevent the prosthesis from subsequently shifting.

Known devices used for the transvascular implantation of heart valve prostheses are often not suitable for easy implantation of a heart valve prosthesis due to the required degree of positioning accuracy. Furthermore, until now it has only been possible to correct an incorrectly positioned heart valve prosthesis that has already been partially implanted with great difficulty—if at all.

These problems have been overcome by means of the medical device of the present invention which has an integral structure cut from a metal tube to provide features that allow accurate positioning and firm anchoring.

SUMMARY OF THE INVENTION

In a first embodiment of the invention, a self expandable endoprosthesis for treating a heart valve insufficiency is provided, wherein the endoprosthesis comprises at least one retaining means for maneuvering the endoprosthesis into and out of position within the patient.

In a particular aspect of the first embodiment the self-expandable endoprosthesis has a plurality of positioning arches for positioning the endoprosthesis in position within a patient and an anchoring segment with retaining arches for accommodating a prosthetic heart valve, wherein the positioning arches and retaining arches have a co-operative shape to hold the flaps of an incumbent heart valve between the positioning and retaining arches when the endoprosthesis is in situ within a patient.

The present invention resides in a medical device which comprises a self-expandable endoprosthesis (hereafter referred to simply as stent) which includes a valve-supporting anchoring segment for the accommodation of a heart valve prosthesis. The stent has a minimised configuration in a first mode that allows the stent to be introduced into the heart by way of a catheter. The stent is 'programmed' to respond to a stimulus that allows the stent to expand to a second mode having an open or expanded configuration. The stent design is distinctive due to the fact that the stent is provided with at least three positioning arches that project radially outwards from the plane of the stent. The positioning arches take up an open position when the endoprosthesis assumes its second pre-definable mode and, when in situ within the body, sit in the pockets of the native heart valve. Correct positioning of the stent is thus determined by the siting of the positioning arches in the valve pockets which the surgeon should be able to feel.

In co-operation with the anchoring segment, the positioning arches engage the original (old) flaps of the heart valve that are to be replaced, resulting in an automatic fixing and positioning of the medical device regarding axial rotation on one hand and the horizontal position on the other hand. Thus, the stent is anchored by means of both a radial force imparted by the design and functional properties of the stent, and a clipping action in a manner similar to a paper clip, with the positioning arches on one side for the heart flaps and the anchoring segment on the other. The native heart valve flaps act as a seal and substantially minimise undesirable leakage of blood around the stent. While the device is referred to herein as a stent, it may also be thought of and referred to as a valve clip, within the frame of which a replacement valve is located.

It will be appreciated that while the device of the present invention may be used to replace native heart valves, the device may also be used to replace a failing biological prosthesis. Because the device of the present invention clips onto the valve flaps already in place, the device can be inserted within an existing stent without modification or removal of the existing stent.

Since the endoprosthesis (stent) of the medical device has a continuous structure cut from a metal tube incorporating the positioning arches on the one hand and the anchoring segment with retaining arches on the other hand, the endoprosthesis can be made particularly inexpensively and in large numbers. Specifically, it would be conceivable to cut the stent structure from a metal tube by means of a laser, after which the structure is subjected to an appropriate shaping and heat treatment process so that the endoprosthesis can be transferred from a minimised state during implantation to an expanded state at the implantation site. This shaping and heat treatment process is advantageously operated in a series of steps to prevent damage to the stent structure.

Since the endoprosthesis of the medical device has a continuous structure cut from a metal tube each retaining arch is associated with a positioning arch, and every end portion of the positioning arch at the distal end of the endoprosthesis is joined to the terminal portion of an associated retaining arch. Thus, there is no need to provide fixed body joints or similar connecting devices and the complexity of the endoprosthesis is much reduced. Expressed in another way, the endoprosthesis of the medical device proposed by the invention is a stent or clip which, on the one hand, offers a positioning function due to positioning arches having a minimal longitudinal extension and, on the other hand, provides the function of retaining a heart valve prosthesis due to the retaining arches.

As will be seen, when transferring the endoprosthesis from the first pre-definable mode to the second pre-definable mode by widening the cross-section of the entire stent, the retaining arches on the one hand and the positioning arches on the other hand are opened out in a radial direction. The second mode of the endoprosthesis is advantageously selected so that as the retaining and positioning arches open up, they press against the vessel wall of the aorta and form a positive connection with it, thereby anchoring the medical device firmly at the implantation site.

The structure of the endoprosthesis imparts a particularly short shape to the medical device and so the medical device is particularly easy to manoeuvre in its minimised state. This is of particular advantage if the implantation route to the heart is via the aortic arch. The minimum length of the medical device is made possible because every end portion of the positioning arch at the distal end is joined to the end portion of an associated retaining arch and both the positioning arch and the retaining arch extend to the proximal retaining region of the medical device or endoprosthesis. The anchoring segment that accommodates the heart valve prosthesis therefore lies at the proximal retaining region of the endoprosthesis.

Advantageous and preferred embodiments of the medical device are specified in the dependent claims.

In one particular embodiment every positioning arch and its associated retaining arch has an essentially U-shaped or V-shaped structure which is closed towards the proximal end of the endoprosthesis.

In a preferred embodiment of the anchoring region or segment, it would be conceivable for the anchoring segment to be of an essentially U-shaped or V-shaped structure which is closed at the distal end of the endoprosthesis. In such a case, the distal region of the anchoring segment constitutes the tip of the anchoring segment and the respective arms of the anchoring segment are joined to the respective arms of two adjacent retaining arches at the proximal end of the anchoring segment.

Alternatively and in another embodiment, the respective arms of the retaining arches have continuous slots or elongate holes extending in the longitudinal direction of the retaining arches. The purpose of such a feature is to enable and assist the expansion of the endoprosthesis from the minimised state into the expanded state because these slots or elongate holes are preferably designed to permit a particularly easy cross-sectional expansion of the stent (endoprosthesis) whilst simultaneously reducing the length of the stent. Such slots or elongate holes have the additional advantage of saving on material.

In the case of the latter embodiment it would be conceivable for the respective retaining arches to be additionally provided with reinforcing portions which interrupt the slots extending in the longitudinal direction of the retaining arches. These reinforcing portions essentially prevent components of the retaining arches from projecting outwards from the circumferential plane of the endoprosthesis when the endoprosthesis is in an expanded state.

Each positioning arch is cut from the material blank of the metal tube which is accommodated by the essentially U-shaped or V-shaped structure of the associated retaining arch. In this preferred embodiment of the stent structure, therefore, the respective retaining arches of the retaining segment form the proximal anchoring region of the endoprosthesis similarly, the respective positioning arches are of a design symmetrical with the retaining arches but lie slightly in front of the distal retaining region of the medical device. The respective distal ends of the positioning arches are joined to the respective distal ends of the co-operating retaining arches in the distal retaining region of the endoprosthesis. When the endoprosthesis is in an expanded state, not only the proximal anchoring region with the heart valve prosthesis fitted to it, the positioning arches disposed between the proximal anchoring and the distal retaining regions of the medical device open out, but also the joining points between the respective positioning arches and retaining arches at the distal end of the medical device. This provides a radially acting force which is applied to the vessel wall via the distal retaining region of the medical device which further assists anchoring of the medical device at the implantation site.

Since the medical device is in a (an expanded) state in which the distal retaining and proximal anchoring regions as well as the positioning arches are opened out radially when the endoprosthesis assumes the second mode, the expanded medical device has a shorter length than it does in its minimised state. To enable the length of the medical device in its expanded state to be set beforehand, it would be conceivable to connect the respective distal end portions of the positioning arches to the distal end portions of the associated retaining arches using a connecting web extending essentially in the longitudinal direction of the endoprosthesis rather than directly. The length of the medical device in the expanded state can therefore be adapted by selecting the length of this connecting web accordingly. However, it is preferable, especially with a view to ensuring good maneuverability of the medical device during the implantation process, i.e. when the endoprosthesis is in its first (minimised) mode, if the connecting web between the respective end portions of the positioning arches and retaining arches is selected so that it is as short as possible.

According to a second embodiment of the invention a catheter tip is provided, which can be disposed at the proximal end of the catheter system, and in which the endoprosthesis of the first aspect can be accommodated, said catheter tip having a retaining mechanism for releasably securing at least the distal end of the endoprosthesis in the catheter tip.

In particular aspects of the second embodiment the catheter tip has a retaining mechanism shaped to co-operate with the retaining means on the endoprosthesis. In another particular aspect of the second embodiment the catheter tip the retaining mechanism has a crown with at least one pocket, the at least one pocket having a shape complementary to that of the endoprosthesis retaining means.

In one particularly preferred embodiment of the medical device, the endoprosthesis has retaining means at its distal end which can be engaged with corresponding retaining means on an introduction catheter system, particularly a catheter tip or cartridge. In one embodiment of the retaining means, the means may be in the form of an anchoring eye disposed between two adjacent positioning arches. In which case, the arms of the adjacent positioning arches on the one hand and the arms of the retaining arches associated with the adjacent positioning arches on the other hand are connected to the anchoring eye. It would likewise be conceivable for the arms of the adjacent positioning arches to be directly and the respective arms of the retaining arches associated with the adjacent positioning arches to be indirectly connected via a connecting web extending essentially in the longitudinal direction of the endoprosthesis. Generally speaking, the purpose of the retaining means provided on the distal end of the endoprosthesis is to accommodate appropriate mechanisms on the introduction catheter system which complement that of the retaining means of the endoprosthesis. The engagement between the catheter system on the one hand and the retaining means on the distal end of the endoprosthesis on the other hand can be released by means of an external manipulation to release the medical device at the implantation site, thereby ensuring that the medical device expands and is thus reliably anchored. It will be appreciated that the retaining means may be of any suitable shape or configuration such as eyes, loops, fingers or imperforate heads.

The use of such retaining means enables the stent to remain in contact with the catheter prior to full release of the stent. By maintaining contact with the stent prior to its full release, location and implantation position of the stent can be controlled more accurately by a physician. The functioning of the stent and heart valve prosthesis may also be checked and, if one or neither is functioning correctly, the physician can withdraw and remove the stent by virtue of the retaining means remaining in contact with the catheter.

Problems or complications with a stent may occur post implantation. For example, failure of the stent to deploy properly, misalignment, dislodgement, or damage of the stent after it has been deployed may lead to valve leakage or other problems. In these cases, removal of the stent is desirable. This may be accomplished up to four weeks after implantation and before the stent has become integrated with the implantation site by a covering or over-growth of cells. Therefore, in another embodiment, the retaining means preferably have a shape or configuration which also allows them to engage with parts of a tool that enables removal of the stent. Preferably the retaining means are caught by and engage or interact with parts of the tool so that the stent can be pulled into, for example, a catheter where the stent assumes its first compressed mode and can be withdrawn from the body with minimal or no tissue damage.

As an alternative to the embodiment of the medical device outlined above, it would however also be conceivable for the respective arms of the adjacent positioning arches to be joined to the retaining means indirectly via a connecting web extending essentially in the longitudinal direction of the endoprosthesis. In which case, the arms of the retaining arches associated with the adjacent positioning arches are joined to the retaining means indirectly via a connecting web extending in the longitudinal direction of the endoprosthesis. The connecting web of the retaining arches merges into the connecting web of the positioning arches at the end portion of the positioning arches. Providing the respective connecting webs for connecting the arms of the positioning arches to the retaining means and for connecting the arms of the retaining arches to the end portion of the positioning arches offers a particularly simple but effective way of adapting the length of the endoprosthesis to a patient's respective requirements and does so because the respective lengths of the connecting webs can be selected appropriately.

In another embodiment of the solution proposed by the invention, the retaining means may include at least one barb or hook, the tip of which points in the direction of the proximal end of the endoprosthesis. This ensures that the distal retaining region of the endoprosthesis can be retained at the implantation sit in its expanded state particularly reliably. In this preferred embodiment, therefore, the endoprosthesis is secured at the implantation site due to the radial force exerted on the vessel wall by the endoprosthesis, in particular by the distal retaining region of the endoprosthesis, but also due to the barb hooking into the vessel wall. It would naturally also be possible to use other appropriate design options for the barb(s) or hook(s).

As an alternative to or in addition to the barbs or hooks, another conceivable way of securing the endoprosthesis reliably at the implantation site is for the respective arms of the retaining arches of the endoprosthesis to be provided with an anchoring support in the shape of a bow which projects out from the relevant arm of the retaining arch when the endoprosthesis is in the expanded state. The tip of the bow points in the direction of the distal end of the endoprosthesis. This embodiment provides additional fixing means for the endoprosthesis and additionally secures the medical device to prevent it from becoming dislocated after implantation.

As mentioned above, one main aspect of the invention is that the endoprosthesis is provided with retaining means at its distal end which can be moved into engagement with the retaining mechanism on the tip of an introduction catheter or insertion system. In one embodiment these retaining means are in the form of fixing eyes.

In an alternative embodiment, the retaining means comprises at least one retaining element arranged at the distal region of the stent, the at least one retaining element being designed to be movable into a releasable engagement with a retaining mechanism of an insertion system, such as a catheter tip. Preferably the at least one retaining element engages with a pocket or depression formed in a crown of the retaining mechanism of the insertion system. Most preferably, the at least one retaining element of the stent has a retaining head, having a design which complements at least one pocket or depression formed in the crown of the insertion system, thereby being adapted to co-operate with the retaining mechanism of the insertion system by means of an improved releasable engagement.

In this embodiment, there is less risk that the retaining mechanism of the catheter tip can become wedged or jammed with the distal region of the endoprosthesis. This can be achieved because neither the retaining mechanism of the catheter tip nor the retaining means of the endoprosthesis have parts that protrude from the crown of the retaining mechanism when the endoprosthesis is fixed to the catheter tip. As a result, minimal shaking or moving of the catheter tip should be required to release the engagement between the catheter system and the distal region of the endoprosthesis.

Generally speaking, the retaining means provided on the distal end of the endoprosthesis or stent are to be accommodated in an appropriate mechanism on the insertion catheter system. These mechanisms should be of a design complementing the retaining means of the stent. The engagement between the retaining mechanisms of the catheter tip on the one hand and the retaining means at the distal end of the stent on the other hand can be released by means of an external manipulation to release the stent at the implantation site and allow the stent to expand thus ensuring that the heart valve prosthesis is reliably secured. Naturally, it would also be possible to consider other solutions for the retaining means. For example, the retaining means may have different shapes and/or profiles, being convex or concave and forming a spoon or cup shape. Profiling the retaining means in this manner allows the retaining means to remain seated in position without affecting outward movement, for example as the stent expands radially during its final release steps. Alternatively, the retaining means may be of a ball-and-socket configuration in co-operation with the retaining mechanism at the catheter tip.

In a preferred embodiment of the retaining means, it is conceivable for the means to be provided in the form of a retaining head which is disposed between two adjacent positioning arches. In this embodiment, the respective arms of the adjacent positioning arches on the one hand and the respective arms of the retaining arches associated with the adjacent positioning arches on the other hand are joined to the retaining head. It will be apparent to one skilled in the art that the use of such fixing means is not limited to use with the disclosed stent design. Such retaining means could also be utilised with other stent designs where reliable release of the stent from the implantation means, such as a catheter, is required.

It is important that the stent with the heart valve prosthesis can be easily released from the catheter tip of a catheter system as soon as the heart valve prosthesis is optimally positioned. The mechanism described above has been found greatly to assist in this manoeuvre.

In a third embodiment of the invention there is provided a catheter system for use in treating a heart valve defect, in particular a heart valve insufficiency or narrowing of a heart valve, in a patient, said catheter system comprising a catheter tip, according to the second aspect, and further comprising a self-expandable endoprosthesis, according to the first aspect, accommodated in the catheter tip of the catheter system, and when the endoprosthesis is accommodated in the catheter tip of the catheter system it assumes a first pre-definable mode and outside of the catheter tip and in the implanted state it assumes a second pre-definable mode, and the endoprosthesis is in a folded state in its first mode and in an expanded state in its second mode.

Conventional catheter systems for inserting a self-expandable heart valve stent typically comprise a catheter tip with a retaining mechanism, the retaining mechanism being adapted for releasably securing the distal region of the stent on the catheter tip. The catheter tip typically has a crown with a plurality of projecting elements. The projecting elements of the crown are designed so as to complement retaining eyes provided at the distal region of the stent. In this respect, the retaining mechanism arranged in the catheter tip of the conventional catheter systems co-operates with the distal region of the stent by means of a releasable engagement. The engagement between the retaining mechanism of the catheter system, and the retaining means in the distal region of the stent is normally releasable by means of an external manipulation so that the stent with the heart valve prosthesis attached to it can be released from the catheter at the implantation site.

However, the use of retaining eyes still pose a risk that the engagement between the catheter system and the distal region of the stent can only be released by means of movement of the stent. In particular, the retaining eyes provided in the distal region of the stent may wedge with the projecting elements which protrude from the crown of the retaining mechanism of the catheter tip. As a result, shaking and/or moving of the catheter tip may be required to release the engagement between the catheter system and the distal region of the stent. Such movement is likely to dislodge the stent from its desired position and may damage the prosthesis.

Thus, there is still a risk of heart valve prostheses being incorrectly implanted. The heart valve prosthesis must be exactly positioned and longitudinally oriented which requires enormous skill on the part of the surgeon performing the treatment. On the one hand the stent must be accurately positioned and on the other hand the stent must be released from the catheter tip accurately enough in the vicinity of the patient's existing heart valve to ensure both correct lateral positioning accuracy and a correct longitudinal position of the heart valve prosthesis. Amongst other things, incorrect implantation and/or sub-optimal positioning of a heart valve prosthesis can lead to inadequate sealing or valve insufficiency which places considerable stress on the ventricle. If a heart valve prosthesis is implanted too far above the actual heart valve plane, for example, this can cause the outlets of the coronary vessels (coronaries) to close, leading to fatal coronary ischaemia due to heart infarction. This being the case, it is vital that both the lateral positioning accuracy and longitudinal positioning accuracy of a heart valve prosthesis meet these strict requirements.

When such retaining heads described above are used, the catheter tip of the insertion system ideally includes a retaining mechanism for releasable securing at least the distal region of the stent in the catheter tip. Preferably, the retaining mechanism comprises a crown with at least one pocket or depression formed in the crown. The at least one pocket or depression is of a design which complements the shape of the retaining means provided on the distal region of the stent. Thus, the retaining mechanism is adapted to co-operate with the distal region of the stent by means of a releasable engagement. In particular, this solution provides a reduced risk that the retaining mechanism of the catheter tip can become wedged or jammed with the distal region of the stent. This can be achieved because the retaining mechanism of the catheter insertion system has no parts protruding or projecting from the crown of the retaining mechanism. As a result, there should be no need to shake or move the catheter tip to release the engagement between the catheter system and the distal region of the stent.

In one particular embodiment, the at least one pocket or depression formed in the crown of the retaining mechanism has a shape which is adapted for accommodating the retaining means provided on the distal region of the stent with positive locking, thereby providing for releasable engagement between the distal region of the stent and the catheter tip. The at least one pocket or depression may be integrally formed in the crown of the retaining mechanism of the catheter tip. Preferably, the at least one pocket or depression is formed as a mould or inverse image of the retaining means of the stent even if the retaining means comprises, for example, barbs or hooks formed at a retaining head.

Preferably the crown of the retaining mechanism is generally cylindrical and the at least one pocket or depression formed in the crown has a shape adapted to completely accommodate completely the retaining means provided on the distal region of the stent such that there are no parts of the distal region of the stent protruding from the superficial surface of the cylindrical crown. Hence, this preferred embodiment leads to a catheter tip which has a very compact retaining mechanism with the surprising advantage that the diameter of the catheter tip can be reduced.

In one embodiment, the catheter tip further comprises 'snap-on' means arranged on the at least one pocket or depression formed in the crown for releasable fixing of the retaining means in the at least one pocket or depression. Preferably, this snap-on means comprises a projecting rim or flange arranged on or near the outer edge of the at least one pocket or depression formed in the crown. The projecting rim or flange may be adapted to hold the stent retaining means in the at least one pocket or depression. Such snap-on means, for example in the form of a clip mechanism, serves to fix temporarily the stent retaining means during loading of the catheter tip. Preferably the snap-on means are designed such that the resisting force caused by the snap-on means and acting on the stent retaining means is smaller than the radial forces acting on the distal portion of the stent when the stent during expansion. This has the advantage that the snap-on means should not retard or inhibit the stent during its final release thus ensuring efficient release of the stent.

In another embodiment, the crown of the retaining mechanism further comprises at least one groove formed therein. The at least one groove is assigned to the at least one pocket or depression and extends essentially in the longitudinal direction of the crown from said pocket or depression to one end of the crown. The at least one groove has a shape adapted to accommodate a connecting web of the stent. The connecting web of the stent extends essentially in the direction of the stent and connects the stent retaining means with respective arms of the stent. Preferably, the groove associated to the pocket or depression formed in the crown is formed as a mould or inverse image of the connecting web or other parts of the stent, extends essentially in the direction of the stent and connects the retaining means with respective arms of the stent.

Of course, a catheter tip of the kind as defined above may also comprise snap-on means arranged on the at least one groove formed in the crown of the retaining mechanism for releasable fixing of the stent connecting web which connects the stent retaining means with the respective arms of the stent. Preferably, this snap-on means comprises a projecting rim or flange arranged on or near the outer edge of the at least one groove formed in the crown of the retaining mechanism, said projecting rim or flange being adapted to hold the connecting web of the stent in the at least one groove.

Thus, the catheter tip has an improved retaining mechanism for releasably securing at least the distal region of the stent in the catheter tip. The catheter tip can be connected to a catheter system by means that allow manipulation of the catheter tip. Such catheter systems are known in the art and may, for example, comprise a handle which further comprises operating means which co-operate with the catheter tip so that when the operating means are operated, the stent can be released from the catheter tip in steps in a pre-definable sequence. In addition, the catheter tip may further comprise a housing system for accommodating at least the proximal region of the stent. The housing system preferably comprises a first housing portion for accommodating first functional components of the stent, for example the retaining arches of the stent, and a second housing portion for accommodating second functional components of the stent, for example the positioning arches.

In a yet further embodiment, the endoprosthesis has an external diameter of approximately 5.0 mm and a length of between 33.0 mm and 40.0 mm, preferably between 34.0 and 39.0 mm, even more preferably between 34.37 mm and 38.37 mm, in its first mode. This means that the medical device can be introduced by means of a 21F introduction system, for example, and heart valve prostheses with a diameter of 21 mm to 28 mm may be used. The length specifications given above are currently preferred values based on medical devices suitable for the majority of patients requiring treatment.

In order to obtain a particularly reliable anchoring of the implanted medical device in its expanded state, the endoprosthesis may be subjected to a shaping and heat treatment process during its manufacture so that when the endoprosthesis is in the finished state, it has a slightly concave shape tapering in the direction of the proximal anchoring region of the endoprosthesis in its second mode. In other words, the proximal anchoring region of the endoprosthesis, i.e. the region to which the heart valve prosthesis is attached, has a slightly narrower diameter than the distal anchoring region. It has been found that if the distal anchoring region of the endoprosthesis in the second mode has an approximately 10% to 25% bigger diameter than the proximal anchoring region of the endoprosthesis, radial forces are generated in particular at the distal anchoring region of the endoprosthesis which enables the medical device to be securely anchored in the vessel without causing damage to the vessel wall. Due allowance is also made for the peristaltic movements of the heart and vessel wall. The slightly lower radial force expended by the proximal anchoring region of the endoprosthesis not only serves as a means of anchoring the medical device in the aorta but in particular also opens out the heart valve prosthesis fitted on the proximal anchoring region of the endoprosthesis and imparts to it a reliable seal with respect to the vessel wall. Naturally, however, it would also be conceivable for the concave shape to be more or less pronounced when the endoprosthesis assumes the second, expanded mode.

It is preferable if the anchoring region of the endoprosthesis has a diameter of between 22 mm and 33 mm, and preferably between 25 mm and 31 mm, in the second mode. This being the case, it would be conceivable for the endoprosthesis to be made in two or more differently dimensioned sizes. In which case, an optimum size of endoprosthesis could be selected depending on the patient and the exact dimensions of the endoprosthesis adapted to the patient to be treated—starting from a pre-defined stent size—by an appropriate finishing treatment of the endoprosthesis (stent), in particular by tempering.

In one, particularly preferred embodiment of the medical device, the device comprises an endoprosthesis (stent) and a heart valve prosthesis, preferably a bio-heart valve prosthesis, even more preferably an aortic heart valve prosthesis. The valve is attached to the anchoring segment of the endoprosthesis by means of a thread, suture or similar. Orifices are provided in the retaining arches of the endoprosthesis through which the thread or similar is inserted. It would be conceivable for the heart valve prosthesis to be connected to the anchoring segment of the endoprosthesis immediately prior to the medical intervention. As a result, the medical device can be made in a modular design, which is of particular advantage in terms of transporting and storing the device. A bio-heart valve prosthesis may comprise material from a variety of sources such as from human, bovine, equine or porcine tissue. Bio-heart valves may be naturally occurring valves or they may be artificially derived or manufactured from suitable biological material, cells or tissue. Alternatively a heart valve prosthesis may be manufactured from biologically compatible artificial materials, that is non-biological sources such as, for example, from pyrolytic carbon, titanium, Teflon, polyester, Dacron and the like.

As regards the preferred material used for the endoprosthesis of the medical device, a shape memory material is ideally used which is designed so that the endoprosthesis is transformed from one shape to another shape by means of an external stimulus. Thus, the endoprosthesis assumes a minimised shape in the first mode (when the medical device is in the minimised state) and an open shape in the second mode (when the medical device is in the expanded state). Especially if a shape memory material such as Nitinol is used, i.e. an equal atomic alloy of nickel and titanium, the implantation process will be particularly gentle during the operation of implanting the medical device, minimising the risk of tissue damage on insertion and implantation. Another advantage of using a shape memory metal is that the open shape can be transformed back to the minimised shape simply by reversing the external stimulus.

During production of an endoprosthesis made from a shape memory material, after the stent structure has been cut from the metal tube, it is deformed and fixed in the desired open shape via a process known as "programming". This operation may be performed on the one hand by heating, deforming and then cooling the stent structure. Alternatively, the stent structure may also be deformed at low temperature by an operation known as cold stretching. As a result, the open shape is memorised whilst the minimised shape actually prevails. If the stent structure is then subjected to an external stimulus, the shape memory effect is triggered and the memorised open shape is restored.

In a particularly preferred embodiment, the external stimulus is a settable switching temperature. It is therefore conceivable for the endoprosthesis material to be heated to a temperature higher than the switching temperature in order to trigger the shape memory effect and thus restore the memorised open shape of the endoprosthesis. By selecting an appropriate chemical composition of the shape memory material, a specific switching temperature can be fixed before the endoprosthesis is programmed. This being the case, the switching temperature is set so that it falls within the range of room temperature and the body temperature of the patient. This is of particular advantage in applications where the medical device is to be implanted in a patient's body. Accordingly, when implanting the medical device, it is merely necessary to ensure that the instrument is not heated until it is in the implanted state on the patient's body (36° C.), at which point the shape memory effect of the endoprosthesis material is triggered.

Preferred embodiments of an endoprosthesis of a medical device proposed by the invention will be described in more detail below with reference to the appended drawings:

BRIEF DESCRIPTION OF DRAWINGS

FIG. 16a shows a side view of a first preferred embodiment of the retaining mechanism disposed in the catheter tip of the insertion system proposed by the invention;

FIG. 16b is a view in cross-section of the retaining mechanism illustrated in FIG. 16a, seen along line A-A indicated in FIG. 16a;

FIG. 16c is a plan view of the distal retaining region of a stent, which can be retained by means of the retaining mechanism illustrated in FIG. 16a;

FIGS. 17a to b illustrate a preferred embodiment of the medical device proposed by the invention with an insertion system of a transapical design, for example illustrated in FIG. 14 or FIG. 15, and a self-expandable heart valve stent in the four different functional modes of the insertion system;

DETAILED DESCRIPTION

Figure 1A:
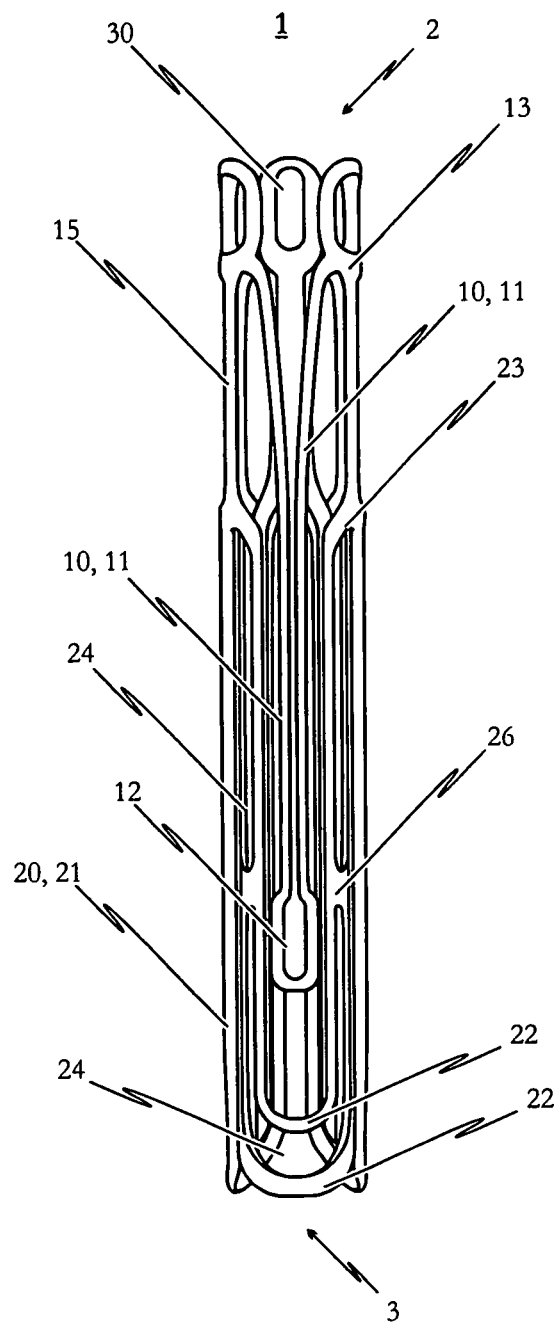
FIG. 1a illustrates a first, preferred embodiment of a self-expandable endoprosthesis for the medical device proposed by the invention in its first predefined mode in which the medical device is in its minimised state.
Figure 1B:
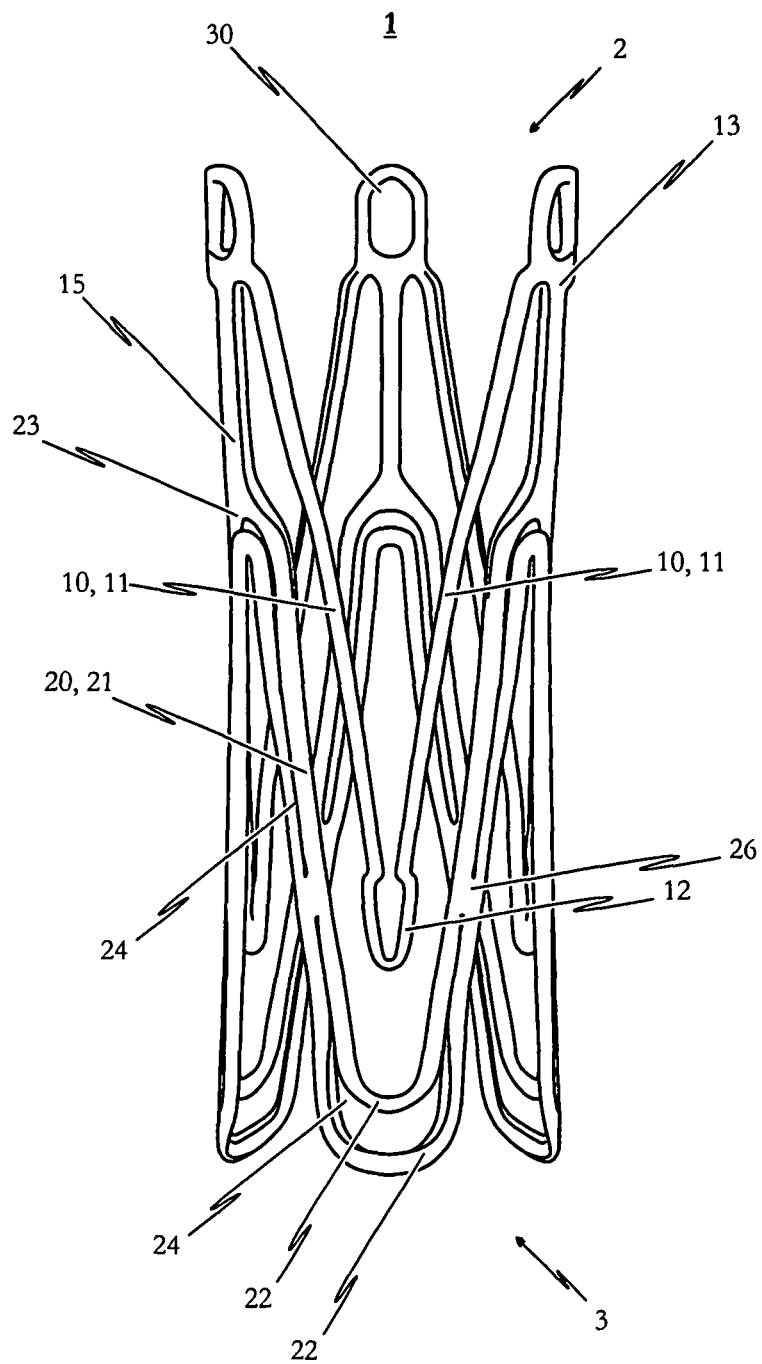
FIG. 1b shows the endoprosthesis illustrated in FIG. 1a but in a state between its first pre-definable mode and its second mode in which the medical device is in its expanded state.
Figure 1C:
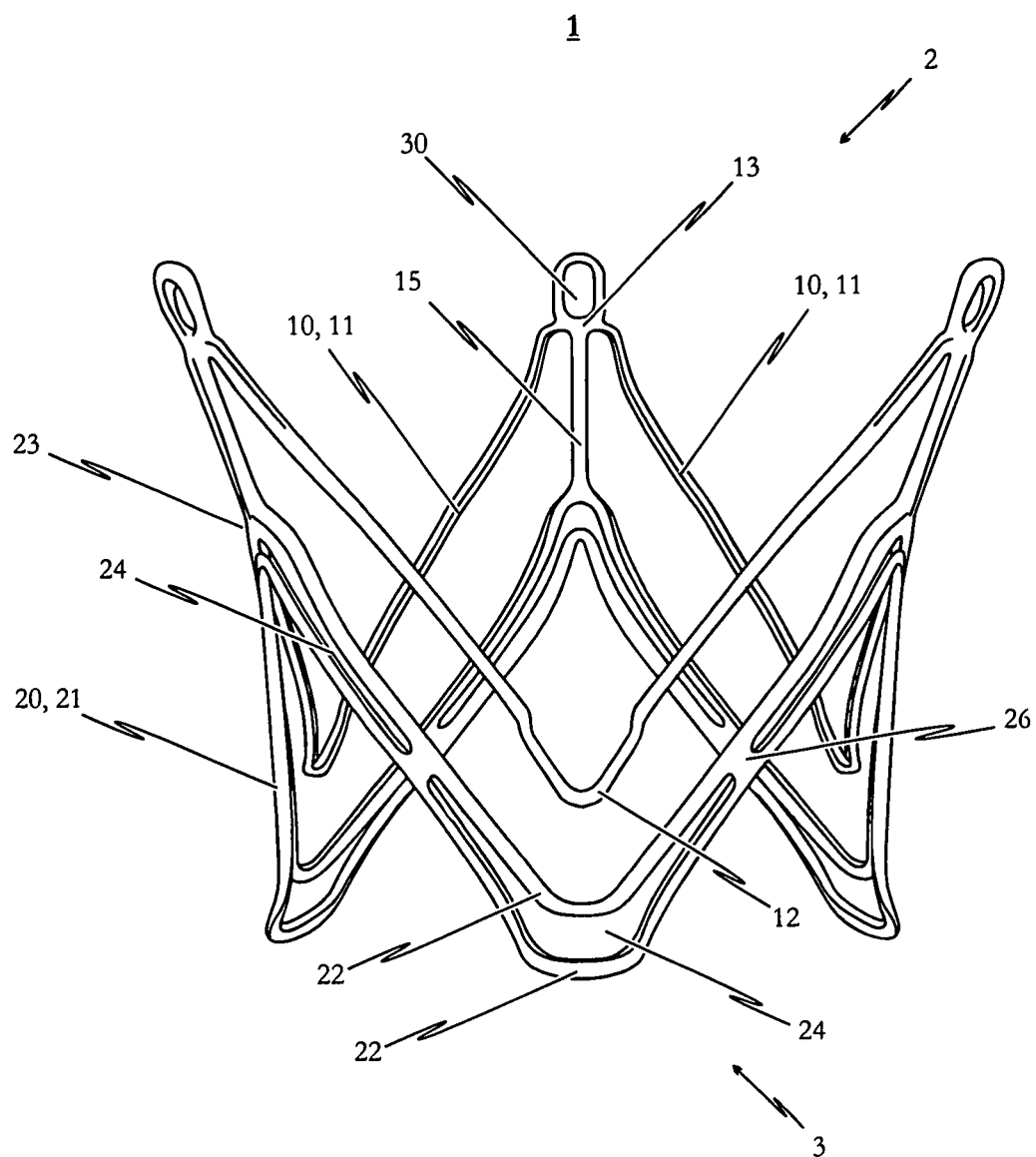
FIG. 1c shows the endoprosthesis illustrated in FIG. 1a but in its second mode in which the medical device is in its expanded state.
Figure 1D:
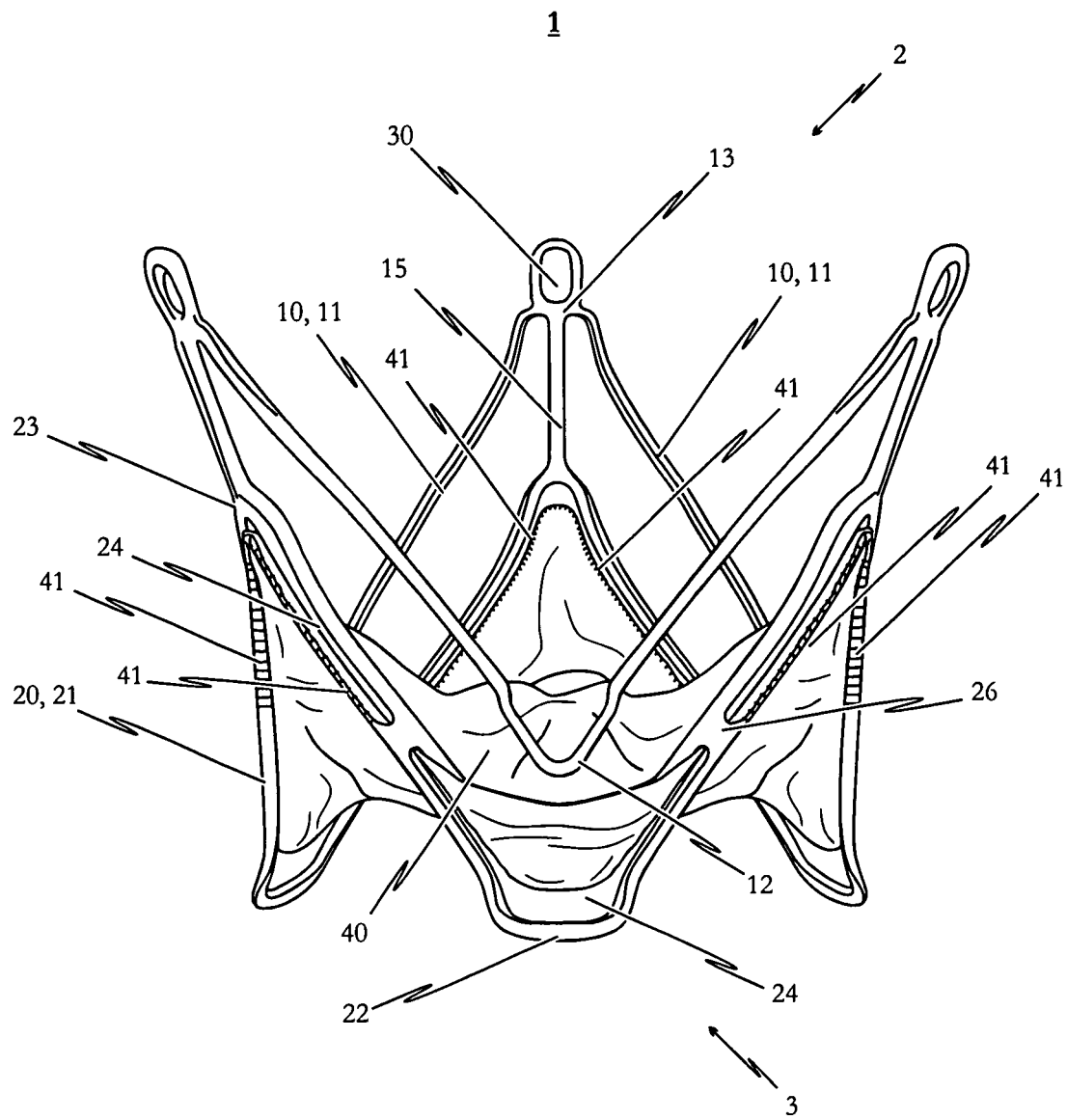
FIG. 1d shows a first, preferred embodiment of the medical device proposed by the invention in its expanded state with an endoprosthesis of the type illustrated in FIG. 1c and a heart valve prosthesis attached to it and opened out.
Figure 1E:
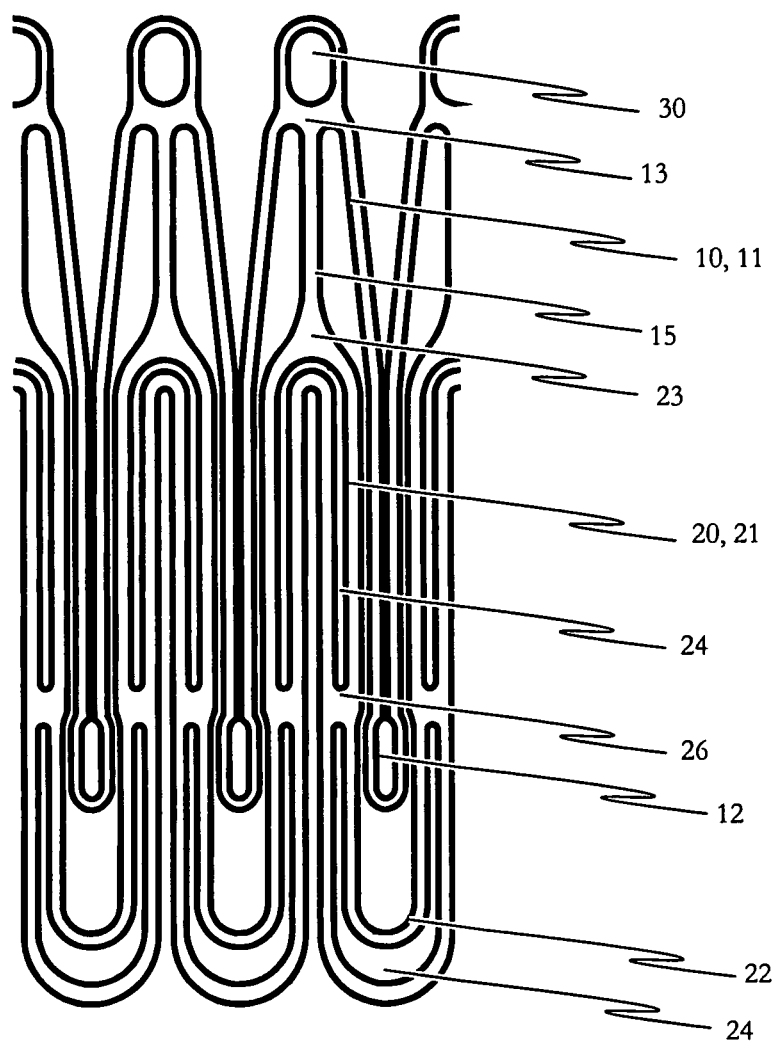
FIG. 1e is a flat projection of a cutting pattern which can be used for the production of the first, preferred, self-expandable endoprosthesis to cut the endoprosthesis illustrated in FIG. 1a integrally from a metal tube.

A first preferred embodiment of the self-expandable endoprosthesis 1 for the medical device proposed by the invention will be described first of all with reference to FIG. 1a to 1e. FIG. 1a illustrates the endoprosthesis 1 in its first pre-definable mode in which the endoprosthesis is in a minimised state and can therefore be introduced into a patient's body with minimal invasion by means of a catheter system. FIG. 1c illustrates the endoprosthesis 1 in its second mode in which the endoprosthesis is in its expanded state. FIG. 1b illustrates the endoprosthesis 1 in a state between the first mode (see FIG. 1a) and the second mode (see FIG. 1c). FIG. 1d illustrates the expanded endoprosthesis of FIG. 1c with a heart valve prosthesis attached to it. The endoprosthesis 1 of this embodiment is distinctive due to the fact that it has a structure which is cut integrally from a metal tube. The cutting pattern used to produce the stent design is illustrated in a flat projection in FIG. 1e.

Specifically, the endoprosthesis 1 comprises a total of three positioning arches 10 which assume the function of automatically positioning the medical device in the patient's aorta. The positioning arches 10 have a rounded head portion 12 which engages in the pockets of the insufficient heart valve to be replaced by the medical device when the medical device is positioned at the implantation site. Providing three positioning arches 10 in total ensures that the requisite positioning accuracy can be obtained in the direction of rotation.

The head portions 12 of the positioning arches 10 pointing respectively towards the proximal end 3 of the endoprosthesis 1 are appropriately rounded so that the vessel wall is not damaged when the positioning arches 10 engage in the pockets of the heart valve to be replaced. Extending from the head portion 12 of the positioning arch 10 to the distal end 2 of the endoprosthesis 1 are two positioning webs or arms 11 in total for each positioning arch 10 which merge into an eye-shaped element 30 at the distal end 2 of the endoprosthesis 1. This eye-shaped element 30 serves as a retaining means for attaching the endoprosthesis 1 and hence the medical device to an introduction catheter system.

Specifically, the respective retaining eyes 30 are disposed between the two arms 11 of two mutually adjacent positioning arches 10. Opening into the transition portion 13 between the two arms 11 of two mutually adjacent positioning arches 10 incorporating the retaining eye 30 is a connecting web 15 extending essentially in the longitudinal direction of the endoprosthesis 1. At the proximal end, the connecting web 15 merges into the respective retaining arms 21 of two mutually adjacent retaining arches 20.

As a result of this stent design, an axially symmetrical structure is obtained whereby a retaining arch 20 is associated with each positioning arch 10. The endoprosthesis 1 in the preferred embodiment illustrated in FIGS. 1a to 1c therefore has a total of three retaining arches 20 which form the base for an anchoring segment of the endoprosthesis 1 for accommodating a heart valve prosthesis 40 (illustrated in FIG. 1d, for example). Providing the respective connecting webs 15 between the distally lying transition portions 23 of two mutually adjacent retaining arches 20 and the transition portions 13 of two mutually adjacent positioning arches 10 results in a stent structure whereby the respective arms 11 of a positioning arch 10 extend essentially parallel with the respective arms 21 of a retaining arch 21 associated with the positioning arch 10.

When the endoprosthesis 1 is in the state illustrated in FIG. 1a, in which it assumes its first mode, the respective arms 11 of the positioning arches 10 directly bound the respective arms 21 of the associated retaining arches 20.

Particular attention should be paid to FIG. 1c in which the endoprosthesis 1 is illustrated in its second mode. Particularly worth mentioning in respect of this diagram is the fact that every positioning arch 10 and its associated retaining arch 20 has an essentially U-shaped or V-shaped structure which is closed towards the proximal end 3 of the endoprosthesis 1. Specifically, every positioning arch 10 is cut from the material portion of the metal tube which is accommodated in the essentially U-shaped or V-shaped structure of the associated retaining arch 20, as may be seen from the cutting pattern illustrated in FIG. 1e.

As may be seen by comparing FIGS. 1a and 1c, during the transition from the first mode into the second mode, the endoprosthesis becomes shorter in the longitudinal direction whilst the cross-section simultaneously becomes wider, in particular at the distal and the proximal anchoring circumferential regions 2, 3. When the endoprosthesis 1 is in the expanded state, the respective positioning arches 10 are specifically opened out to a more pronounced degree in a radial direction from the plane of the endoprosthesis than is the case at the distal anchoring region 2 of the stent 1. The positioning arches 10, which assume the function of positioning the medical device in the implanted state by engaging in the pockets of the heart valve to be replaced, can therefore project further out in a radial direction and can be inserted in the heart valve pockets of the heart valve to be replaced in a particularly easy manner.

FIG. 1d illustrates the embodiment in its expanded state with an endoprosthesis 1 of the type illustrated in FIG. 1c and a heart valve prosthesis 40 attached with the aid of a thread 41 and opened out. As illustrated, opening out the proximal anchoring region 3 of the endoprosthesis 1 in which the heart valve prosthesis 40 is disposed causes the heart valve prosthesis 40 to open out. A radial force is simultaneously applied to the vessel wall (not illustrated) by the proximal end portions 22 of the retaining arches 21, thereby affording a reliable seal of the heart valve prosthesis 40 with respect to the vessel wall.

Although the force exerted by the retaining arches 21 in the radial direction onto the vessel wall causes the medical device to be secured at the implantation site to a certain extent, the distal anchoring region 2 is expanded by a further 10% to 25% in the radial direction than the proximal anchoring region 3 of the endoprosthesis 1 when the medical device is in the expanded state. This allows stable implantation of the medical device, especially in view of the unavoidable peristaltic movement of the vessel wall and the relatively high fluid pressures which prevail. As a result, a slightly concave shape is imparted to the endoprosthesis 1 which tapers in the direction of the proximal anchoring region 3 of the endoprosthesis 1, thereby ensuring that the medical device is firmly anchored in the vessel due to the distal anchoring region 2 of the endoprosthesis 1 pressing against the vessel wall.

In the embodiment illustrated, the respective arms 21 of the retaining arches 20 have uninterrupted slots or elongate holes 24, the purpose of which is to enable or assist expansion of the endoprosthesis 1 from the minimised state into the expanded state. These slots or elongate holes 24 make it easy to widen the cross-section of the stent 1 whilst simultaneously reducing its length. Naturally, however, it would also be conceivable for these slots or elongate holes 24 to accommodate a thread 41 or similar used to attach the heart valve prosthesis 40 (illustrated in FIG. 1d) to the proximal region 3 of the endoprosthesis 1.

The medical device of the present invention is of a modular design essentially comprising the two separately manufactured components, endoprosthesis 1 and heart valve prosthesis 40. The endoprosthesis 1 assumes the function of positioning and securing the heart valve prosthesis 40 in the patient's aorta. It may be preferable if the two components (endoprosthesis 1 and heart valve prosthesis 40) are not connected to one another until immediately prior to performing the surgical intervention; this is of advantage in terms of transporting and storing the endoprosthesis 1 as such since the endoprosthesis 1 is a relatively robust component from a mechanical point of view and can be stored for a significant period of time. This applies in particular if the endoprosthesis 1 is stored in its second mode, i.e. in the expanded state, and is not switched to its first (minimised) mode until immediately prior to undertaking the surgical intervention.

FIG. 1a shows the endoprosthesis 1 is in its first mode, in its minimised state which is the so-called "minimised" mode of the endoprosthesis structure made from a memory shape material. When an external stimulus acts on the endoprosthesis body illustrated in FIG. 1a, the shape memory effect is triggered and the fixed open shape memorised during production of the endoprosthesis 1 illustrated in FIG. 1c is restored. This external stimulus is preferably a settable switching temperature and the body must be at a temperature higher than the switching temperature in order to trigger the shape memory effect and thus restore the memorised open shape of the endoprosthesis 1. By selecting the chemical composition of the material used for the endoprosthesis 1, a specific switching temperature can be fixed before the endoprosthesis is programmed. In the case of the preferred embodiment the switching temperature lies in a range of between 20° C. and the body temperature of the patient.

Therefore, it would be conceivable for the medical device to be cooled accordingly during the introduction process. When the medical device has been moved to the desired implantation site, in other words in front of the native heart valve, preferably by means of an appropriate introduction system, cooling can be interrupted so that the endoprosthesis 1 of the medical device is heated to the body temperature (36° C.) of the patient, thereby triggering the shape memory effect of the endoprosthesis material. Having triggered the self-expanding property of the endoprosthesis 1, radial forces are generated which act on the individual components of the endoprosthesis 1, in particular, on the respective positioning arches 10, 11 and retaining arches 20, 21 of the endoprosthesis 1. Since the endoprosthesis 1 of the medical device is still disposed in the introduction catheter system as before, the radial forces which build up once the critical switch temperature is exceeded and act on the individual components of the endoprosthesis 1 are compensated by the introduction port of the introduction catheter system so that—in spite of the shape memory effect having been triggered—the endoprosthesis 1 of the medical device is forcibly retained in its first (minimised) mode.

By releasing the endoprosthesis 1 from the introduction catheter system in appropriate steps, it is then possible to release the positioning arches 10, 11 of the endoprosthesis 1 through the introduction port of the introduction catheter system first, as a result of which it opens up due to the radial forces acting in the radial direction. The opened positioning arches 10, 11 can then be positioned in the pockets of the native heart valve.

The remaining components of the endoprosthesis 1 and the medical device can then be released through the introduction port of the introduction catheter system. As this happens, the retaining arches 20, 21 open in the radial direction and the heart valve prosthesis 40 attached to the retaining arches 20, 21 by means of a thread 41, etc., for example, thus unfolds in the manner of an umbrella. The radial forces acting on the retaining arches 20, 21 and also on the distal anchoring region 2 of the endoprosthesis 1 cause the endoprosthesis 1 to be pressed in the radial direction against the vessel wall. In this way, a reliable anchoring of the medical device is guaranteed at the implantation site on the one hand and a reliable seal of the heart valve prosthesis 40 is ensured at the proximal anchoring region 3 of the endoprosthesis 1 on the other hand.

Figure 2A:
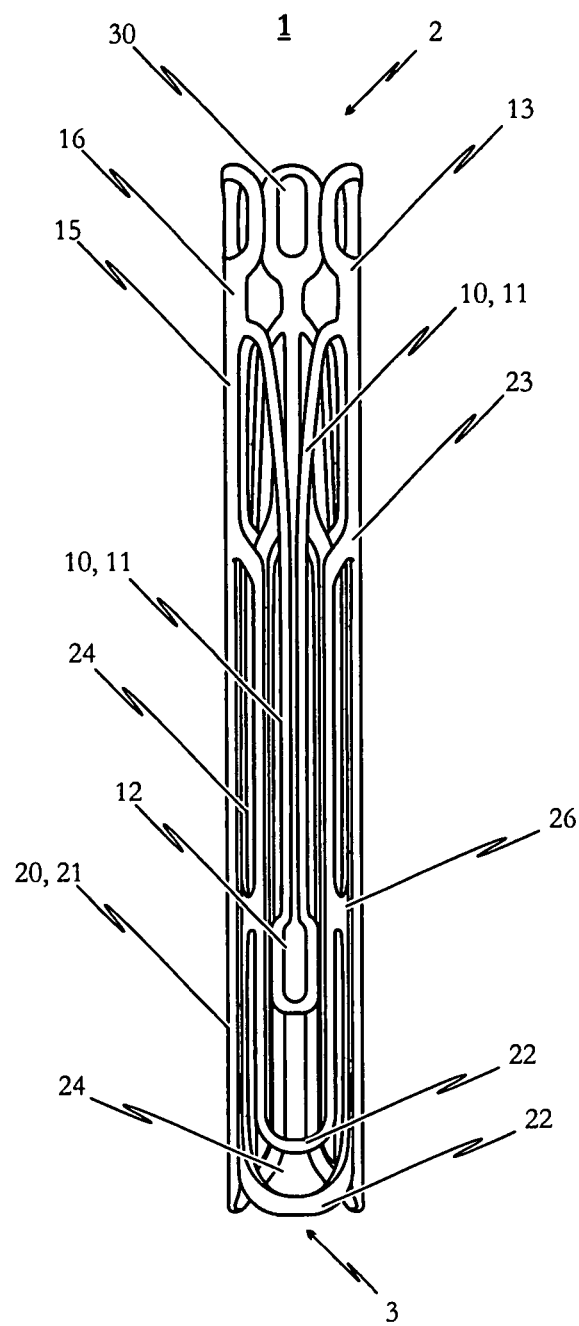
FIG. 2a shows a second, preferred embodiment of a self-expandable endoprosthesis for the medical device proposed by the invention in its first, pre-determined mode in which the medical device is in its minimised state.
Figure 2B:
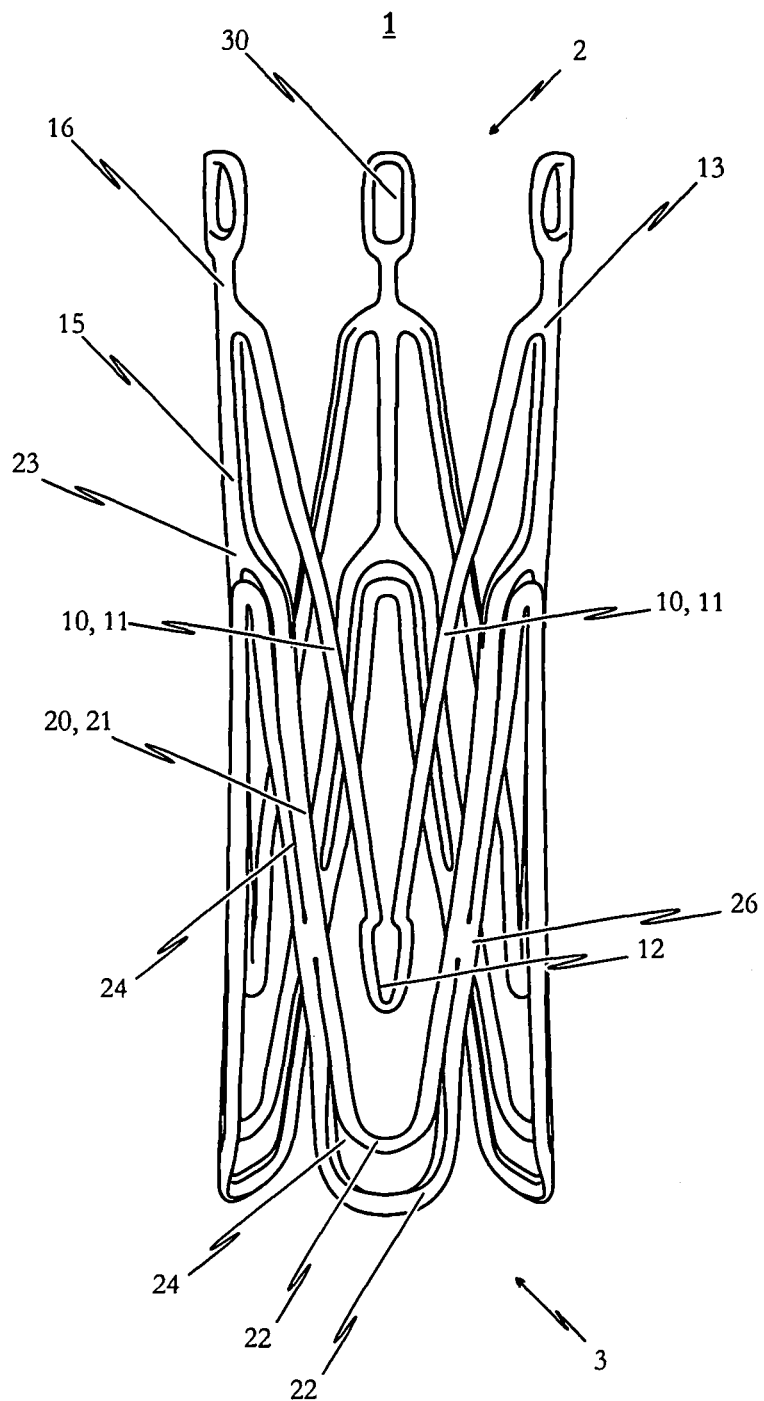
FIG. 2b shows the endoprosthesis illustrated in FIG. 2a in a state between its first, pre-definable mode and its second mode in which the medical device is in its expanded state.
Figure 2C:
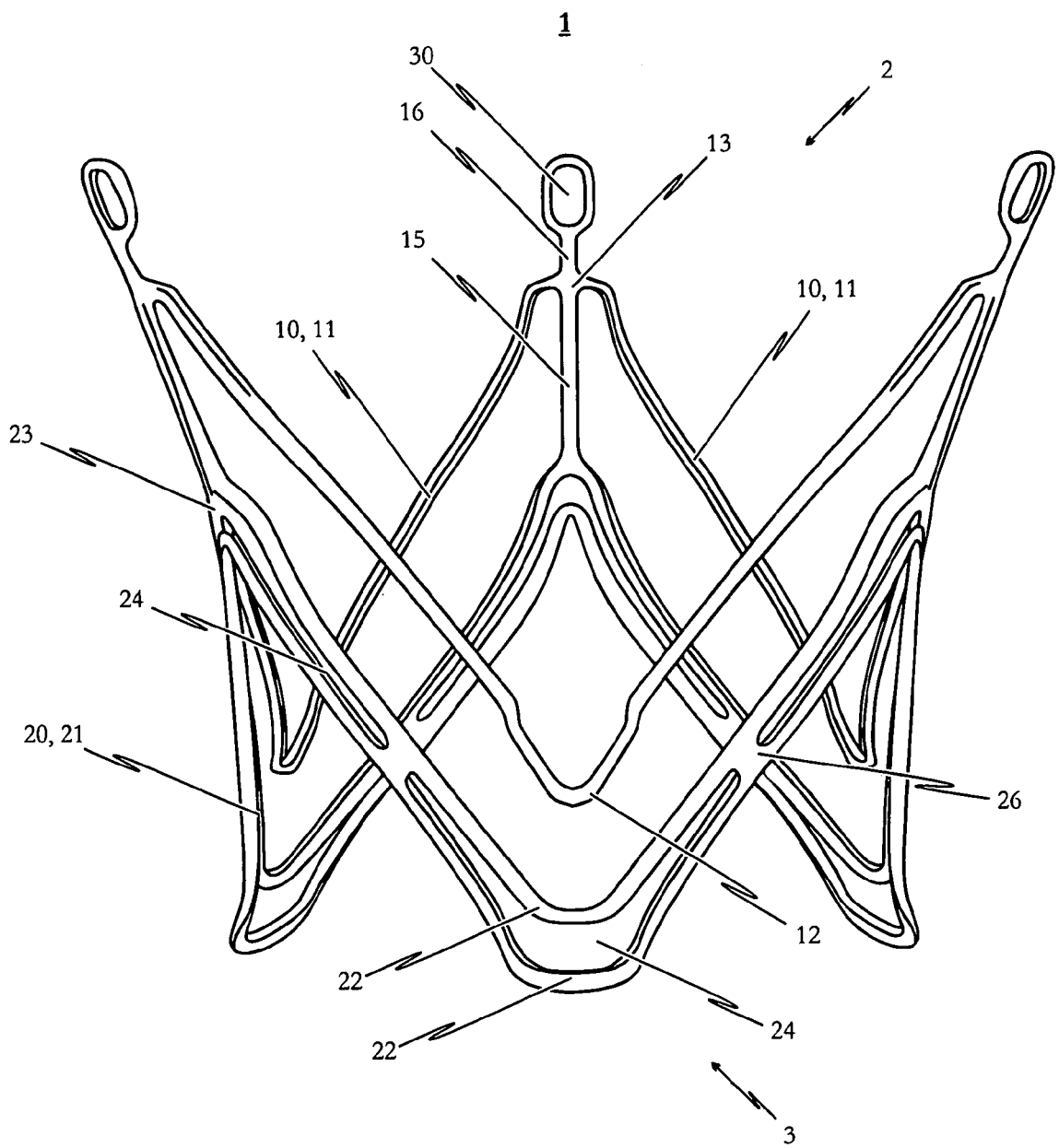
FIG. 2c shows the endoprosthesis illustrated in FIG. 2a in its second mode in which the medical device is in its expanded state.

FIGS. 2a to 2c illustrate a second embodiment of a self-expandable endoprosthesis 1 for the medical device proposed by the invention in its first, pre-definable mode (see FIG. 2a) in its second pre-definable mode (see FIG. 2c) as well as in a state in between (see FIG. 2b).

Figure 2D:
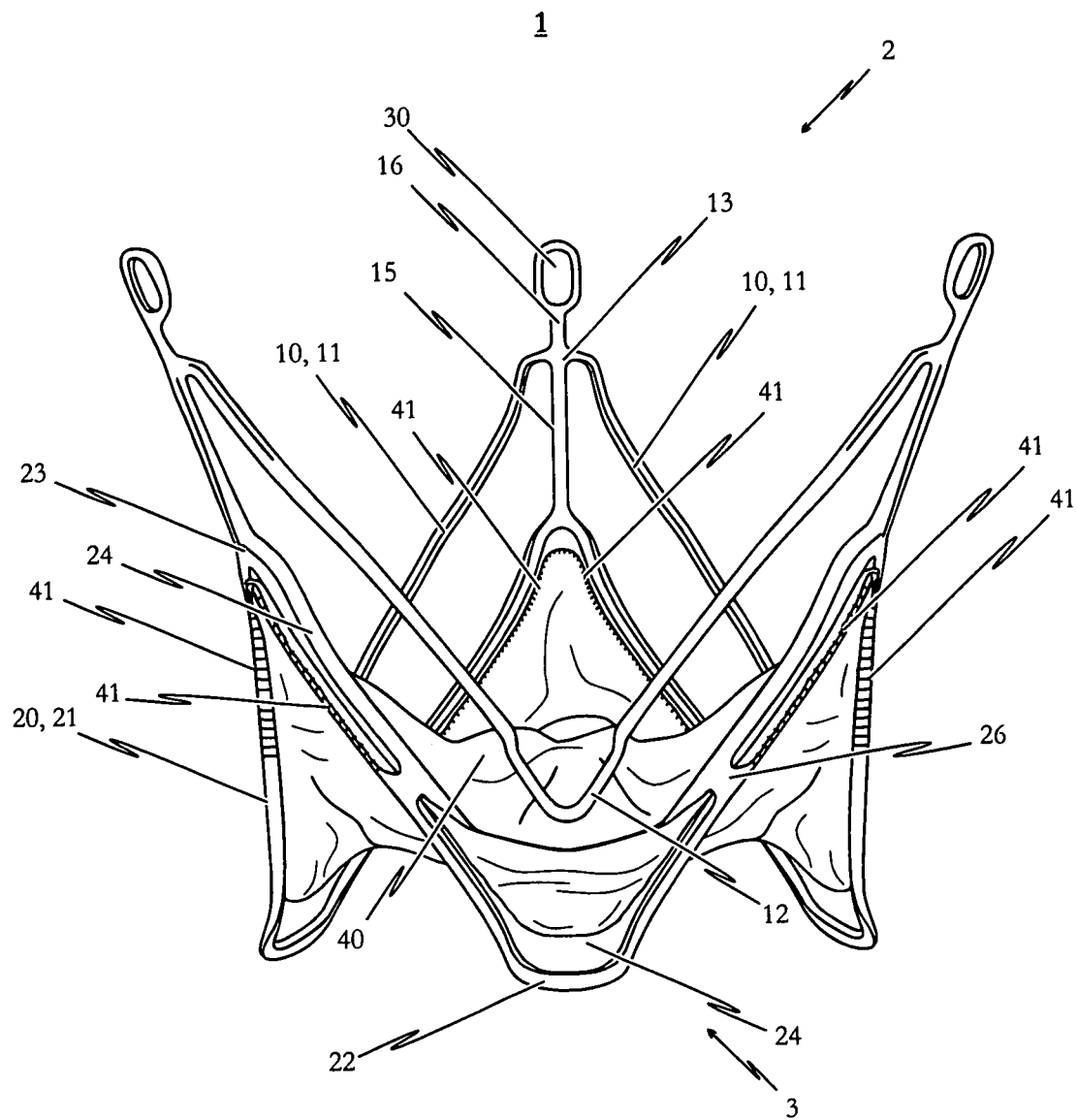
FIG. 2d illustrates a second preferred embodiment of the medical device proposed by the invention in its expanded state, with an endoprosthesis of the type illustrated in FIG. 2c and a heart valve prosthesis attached to it and opened out.
Figure 2E:
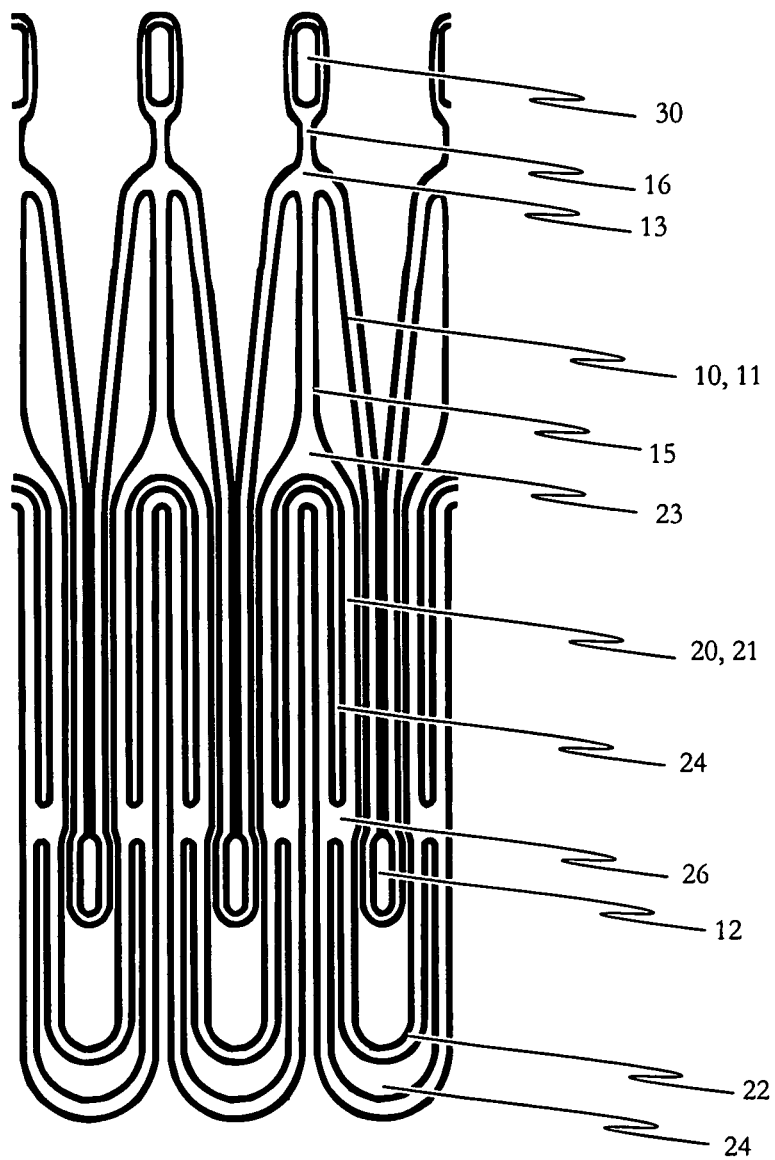
FIG. 2e is a flat projection of a cutting pattern which can be used for the production of the second preferred, self-expandable endoprosthesis to cut the endoprosthesis illustrated in FIG. 2a integrally from a metal tube.

FIG. 2d illustrates a second embodiment of the medical device proposed by the invention in its expanded state with an endoprosthesis of the type illustrated in FIG. 2c and a heart valve prosthesis 40 attached to it and opened out. A flat projection of a cutting pattern which may be used for the production of the second embodiment of the self-expandable endoprosthesis is illustrated in FIG. 2e. This cutting pattern is suitable for cutting the endoprosthesis illustrated in FIG. 2a integrally from a metal tube.

The endoprosthesis 1 of the second embodiment essentially corresponds to the first embodiment described above with reference to FIGS. 1a to 1e. Description of the various components corresponds to that described for FIGS. 1a to 1e and will not be repeated. The second embodiment differs from the first preferred embodiment of the endoprosthesis in that the respective arms 11 of the adjacent positioning arches 10 are joined indirectly via a connecting web 16 extending essentially in the longitudinal direction of the endoprosthesis 1 to the retaining eye 30. The respective arms 21 of the retaining arches 20 are associated with the adjacent positioning arches 10 are indirectly joined via a connecting web 15 extending essentially in the longitudinal direction of the endoprosthesis 1 to the retaining eye 30. Specifically, the connecting web 15 of the retaining arches 20 merges into the connecting web 16 of the positioning arches 10 at the end portion 13 of the positioning arches 10. By selecting the respective lengths of the two connecting webs 15 and 16 accordingly, therefore, the overall length of the stent 1 can be adjusted in an easy manner.

Figure 3A:
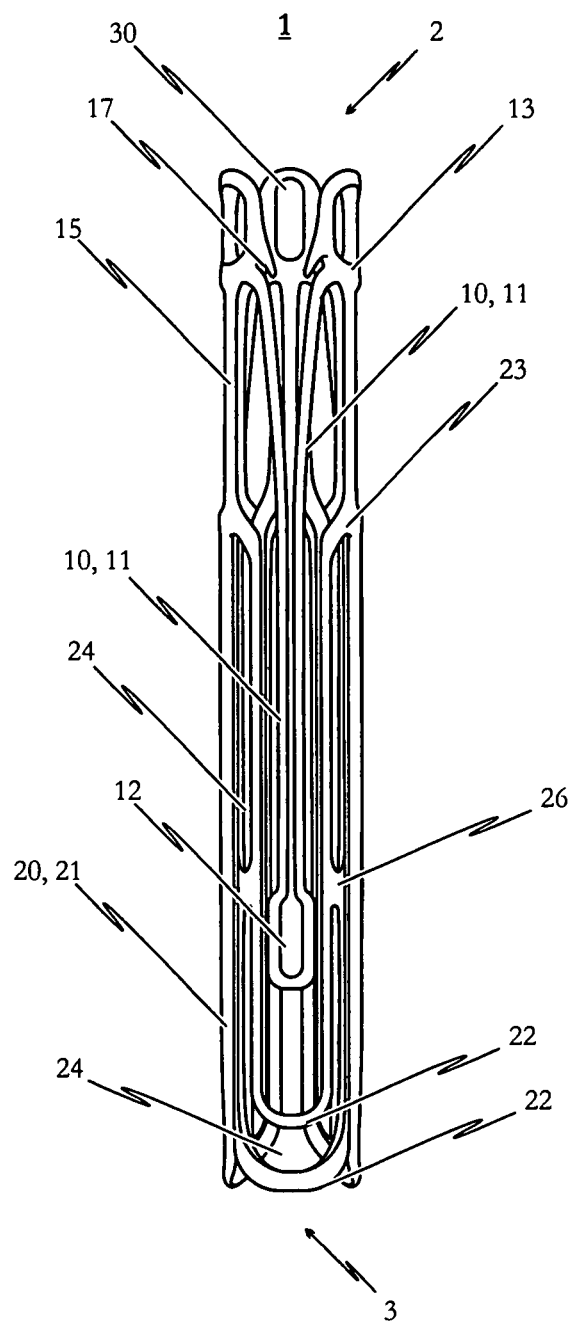
FIG. 3a shows a third, preferred embodiment of a self-expandable endoprosthesis for the medical device proposed by the invention in its first, pre-determined mode in which the medical device is in its minimised state.
Figure 3B:
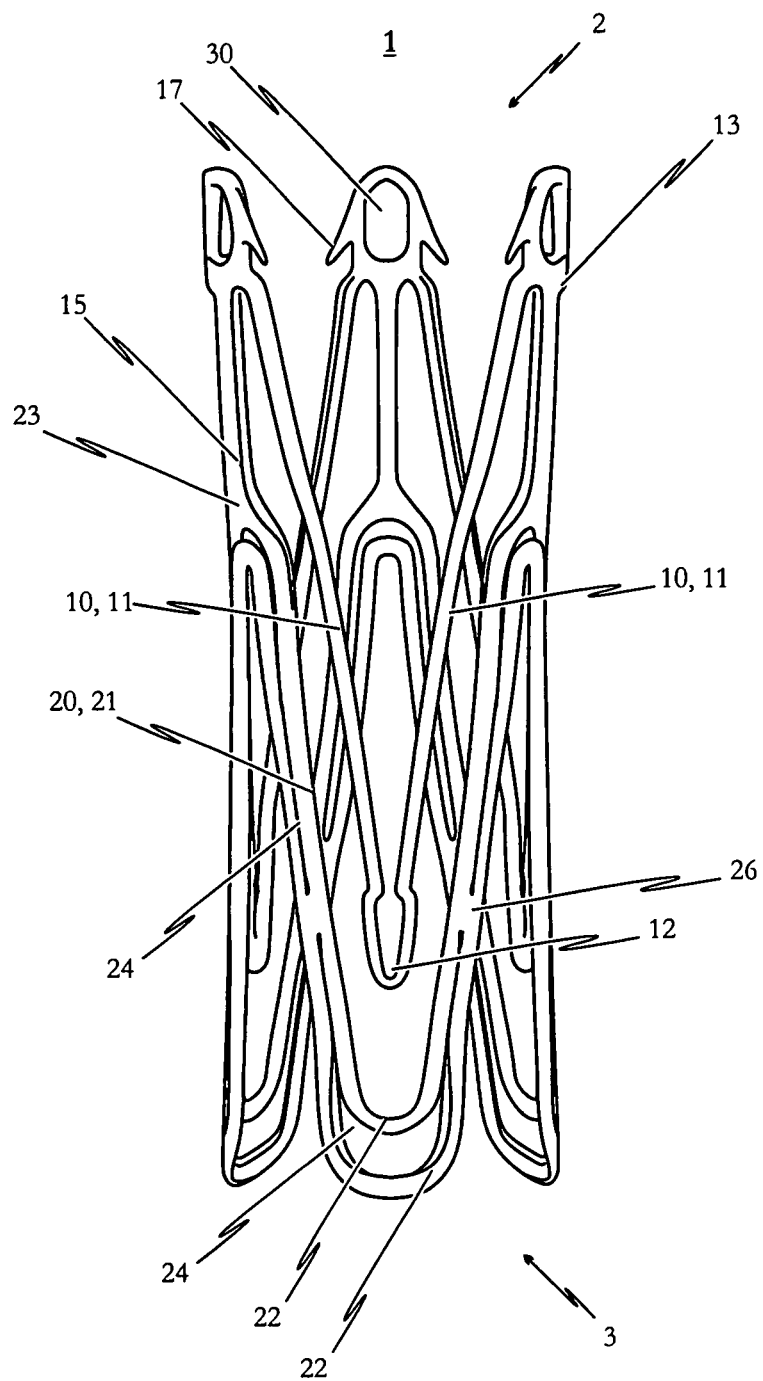
FIG. 3b shows the endoprosthesis illustrated in FIG. 3a in a state between its first, pre-definable mode and its second mode in which the medical device is in its expanded state.
Figure 3C:
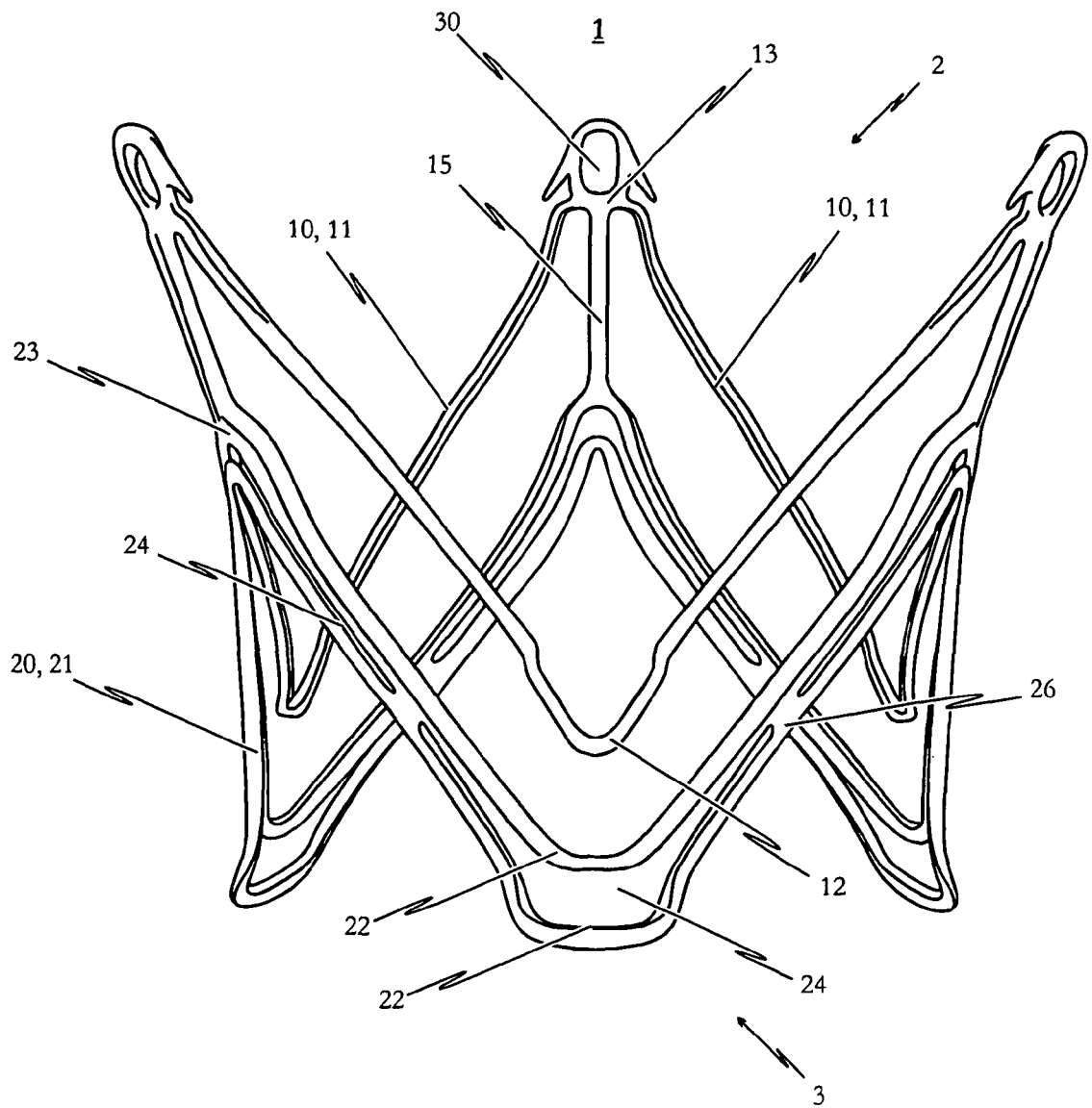
FIG. 3c shows the endoprosthesis illustrated in FIG. 3a in its second mode in which the medical device is in its expanded state.

The third embodiment of a self-expandable endoprosthesis for the medical device proposed by the invention illustrated in FIGS. 3a to 3c essentially corresponds to the first preferred embodiment illustrated in FIGS. 1a to 1c. The difference, however, is that in the third preferred embodiment, the retaining eyes 30 disposed between two adjacent positioning arches 10 are provided with barbs 17, the respective tips of which point in the direction of the proximal end 3 of the endoprosthesis 1. With this modification to the design additional anchoring is provided for the system to prevent the stent 1 from being dislocated in the direction of the left ventricle.

Figure 3D:
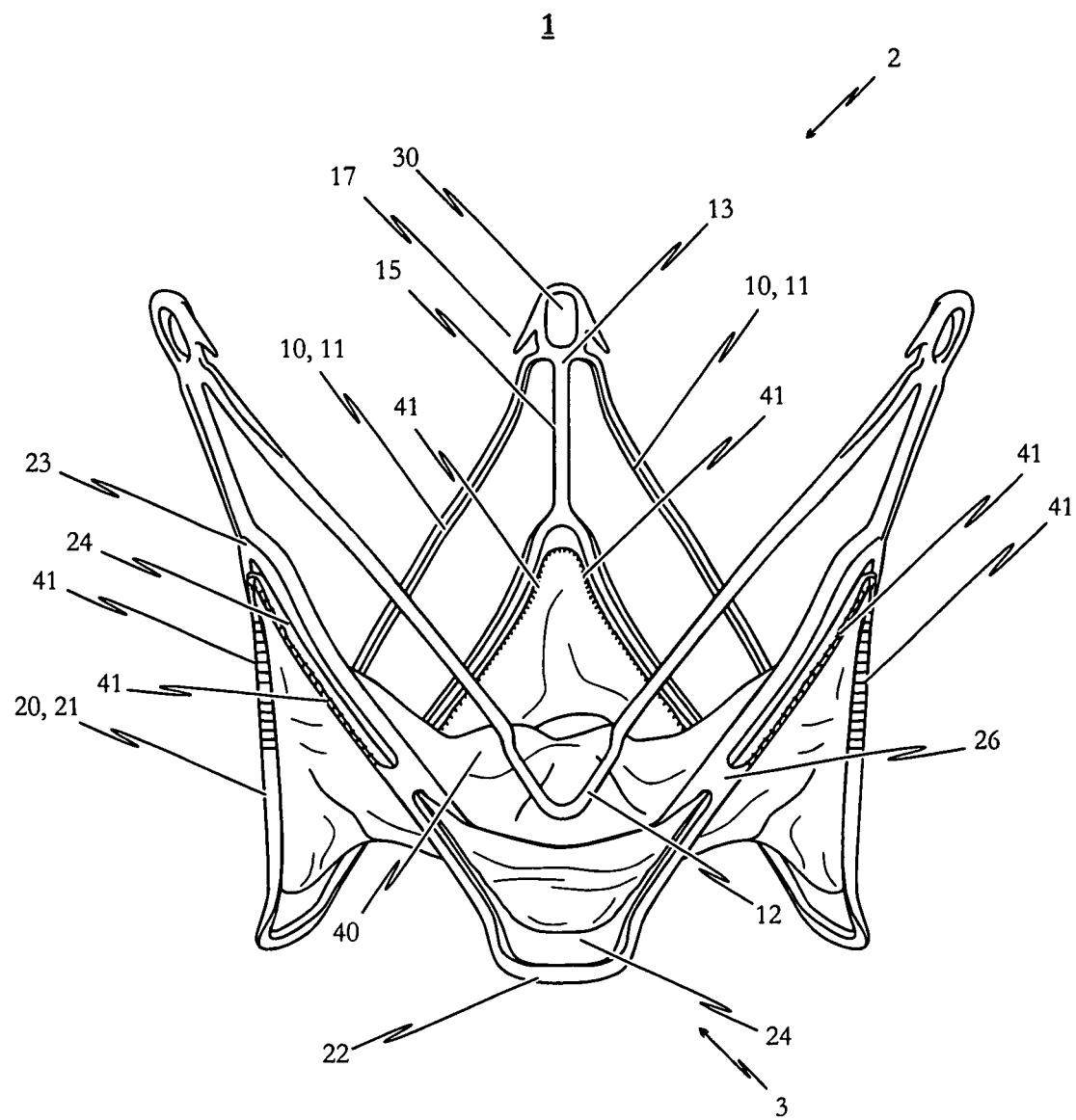
FIG. 3d illustrates a third preferred embodiment of the medical device proposed by the invention in its expanded state with an endoprosthesis of the type illustrated in FIG. 3c and a heart valve prosthesis attached to it and opened out.

FIG. 3d illustrates a third embodiment of the medical device proposed by the invention in its expanded state with an endoprosthesis of the type illustrated in FIG. 3c and a heart valve prosthesis 40 attached to it and opened out. This diagram essentially corresponds to that of FIG. 1d. The difference, however, is that the barb elements 17 described above are provided on the respective retaining eyes 30.

Figure 3E:
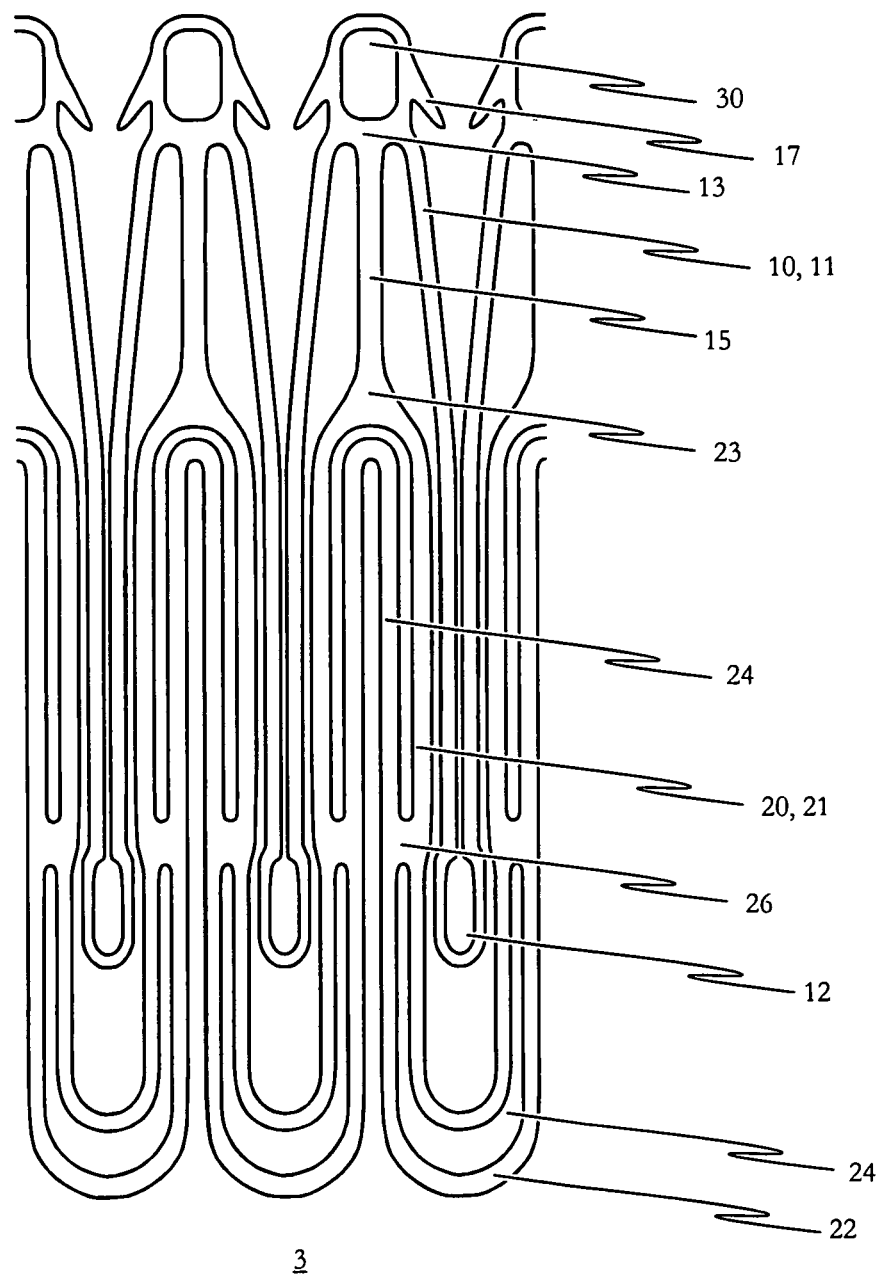
FIG. 3e is a flat projection of a cutting pattern which can be used for the production of the third preferred, self-expandable endoprosthesis to cut the endoprosthesis illustrated in FIG. 3a integrally from a metal tube.

A flat projection of a cutting pattern which may be used for the production of the third embodiment of the self-expandable endoprosthesis 1 is illustrated in FIG. 3e. This cutting pattern is suitable for cutting the endoprosthesis illustrated in FIG. 3a integrally from a metal tube.

Figure 4A:
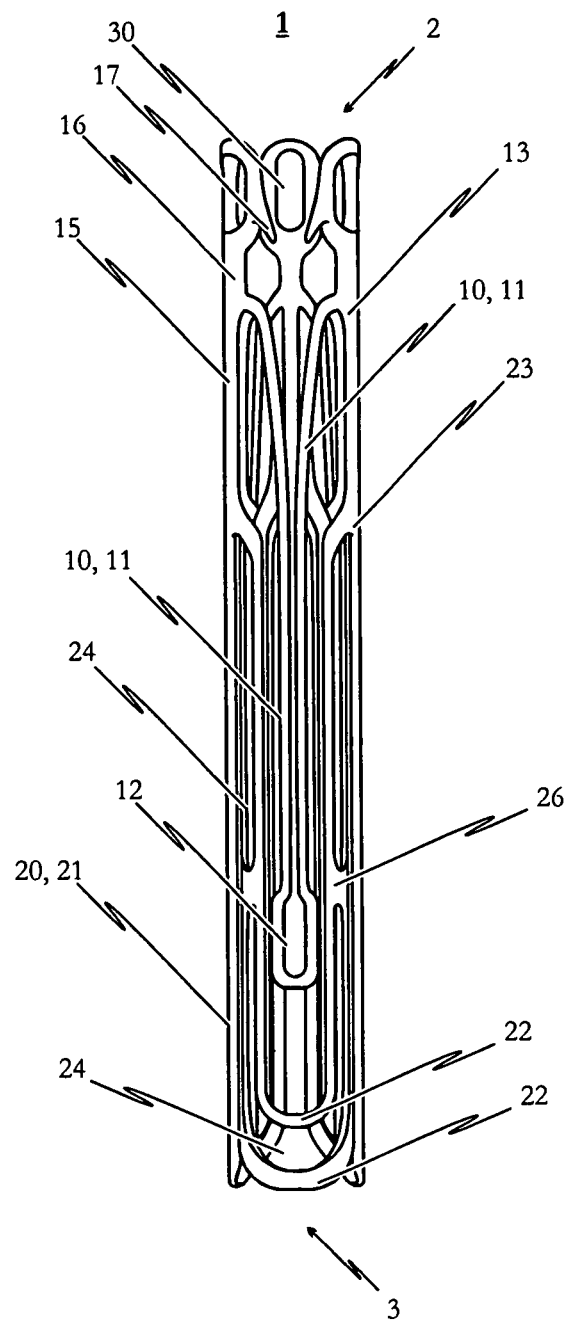
FIG. 4a shows a fourth, preferred embodiment of a self-expandable endoprosthesis for the medical device proposed by the invention in its first, pre-determined mode in which the medical device is in its minimised state.
Figure 4B:
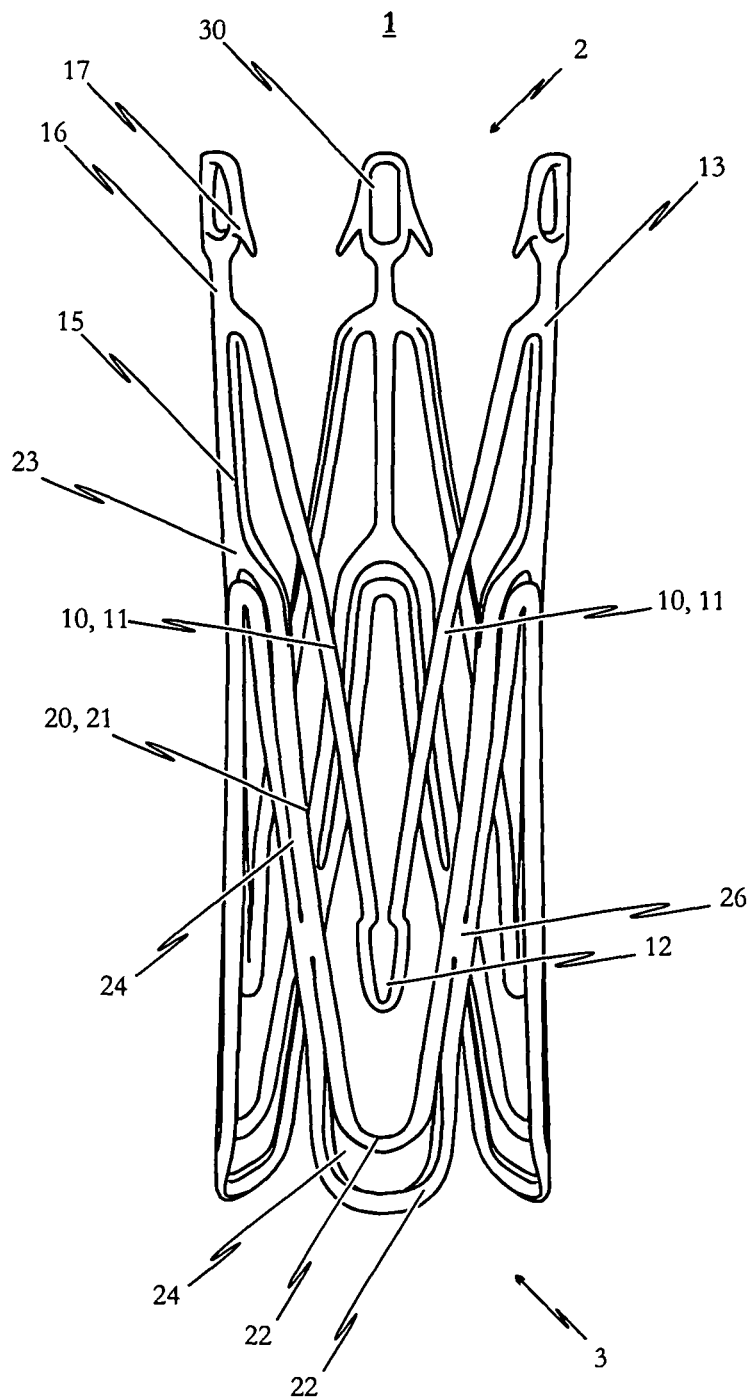
FIG. 4b shows the endoprosthesis illustrated in FIG. 4a in a state between its first, pre-definable mode and its second mode in which the medical device is in its expanded state.
Figure 4C:
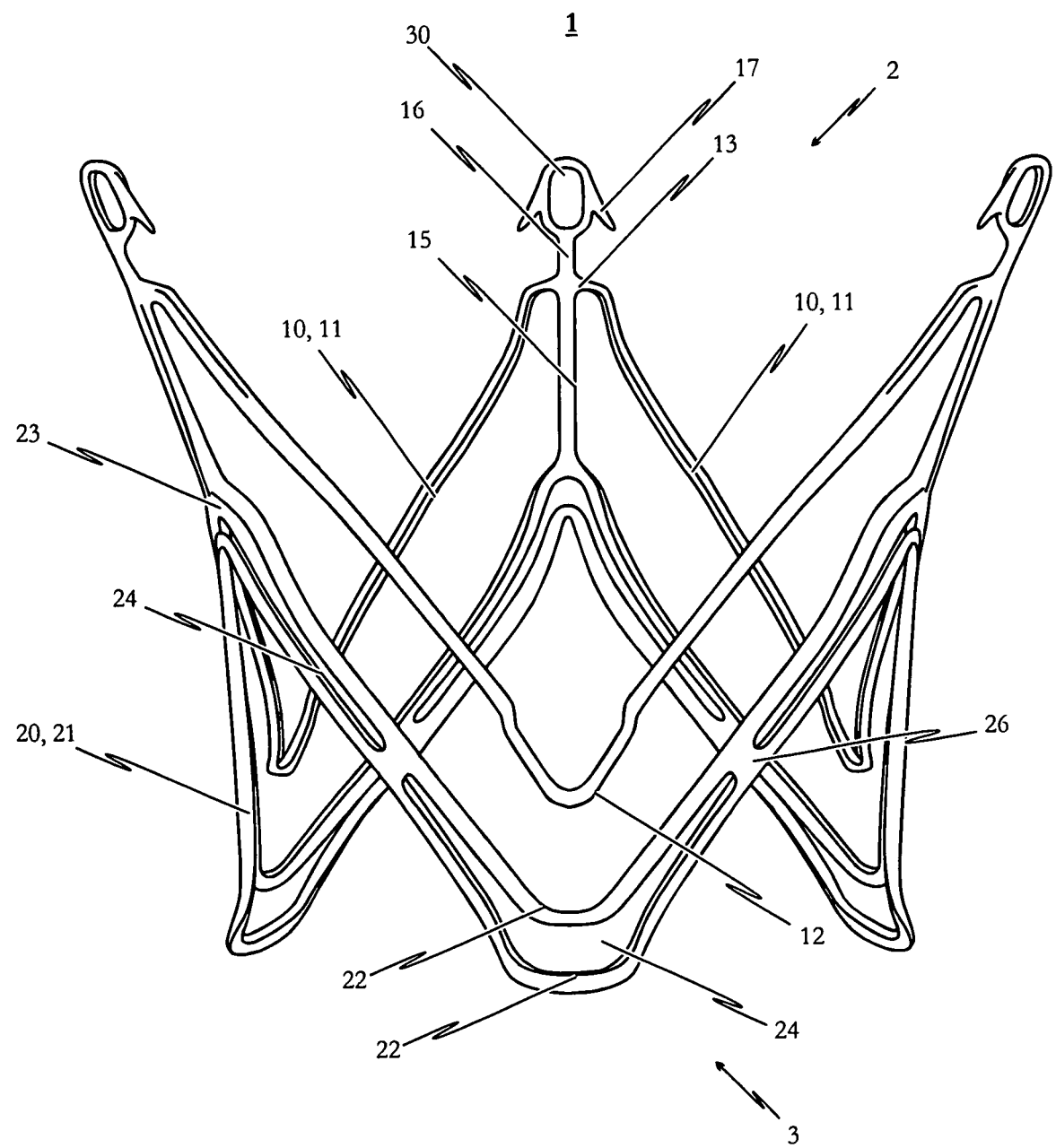
FIG. 4c shows the endoprosthesis illustrated in FIG. 4a in its second mode in which the medical device is in its expanded state.
Figure 4D:
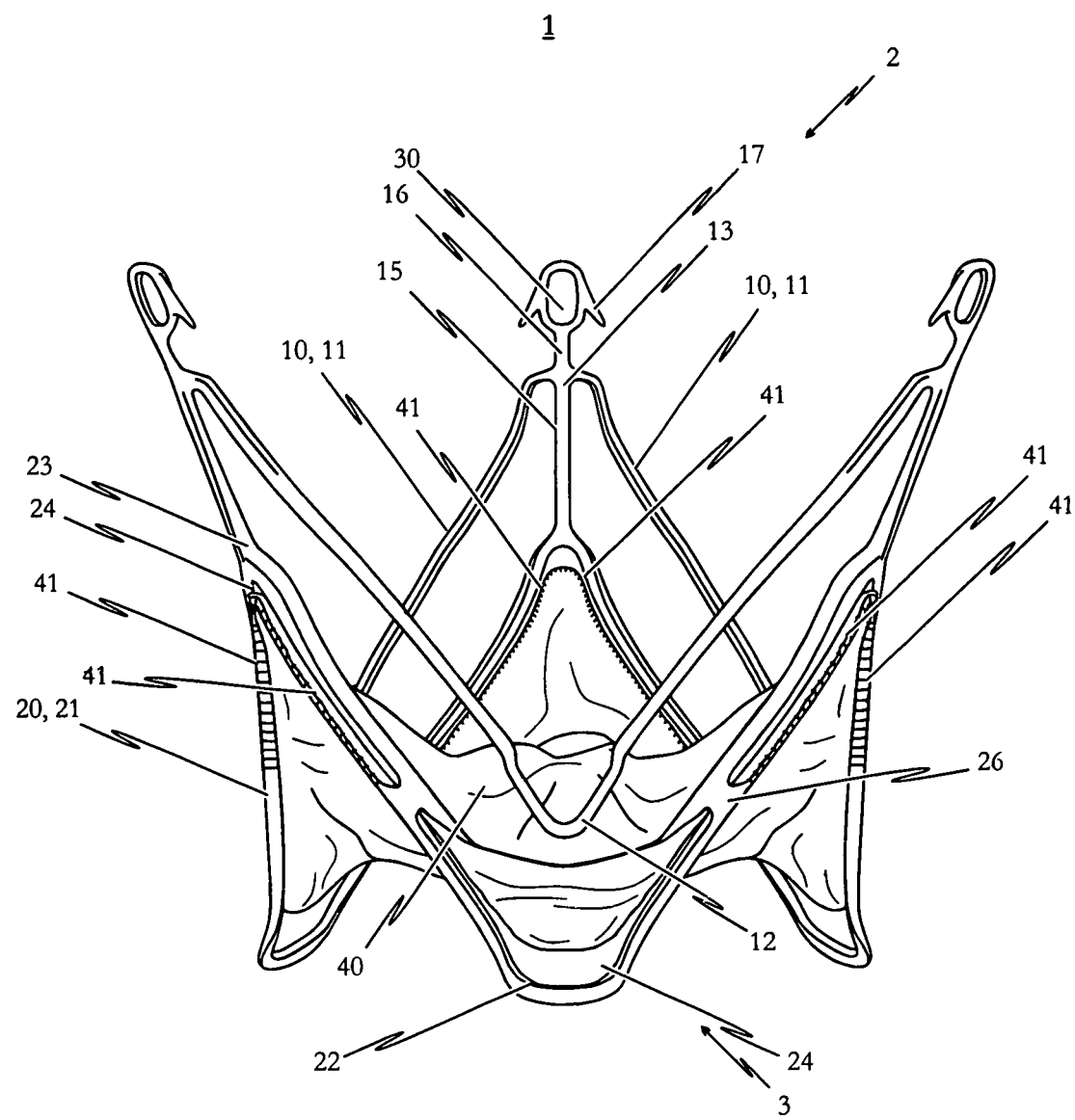
FIG. 4d illustrates a fourth preferred embodiment of the medical device proposed by the invention in its expanded state with an endoprosthesis of the type illustrated in FIG. 4c and a heart valve prosthesis attached to it and opened out.
Figure 4E:
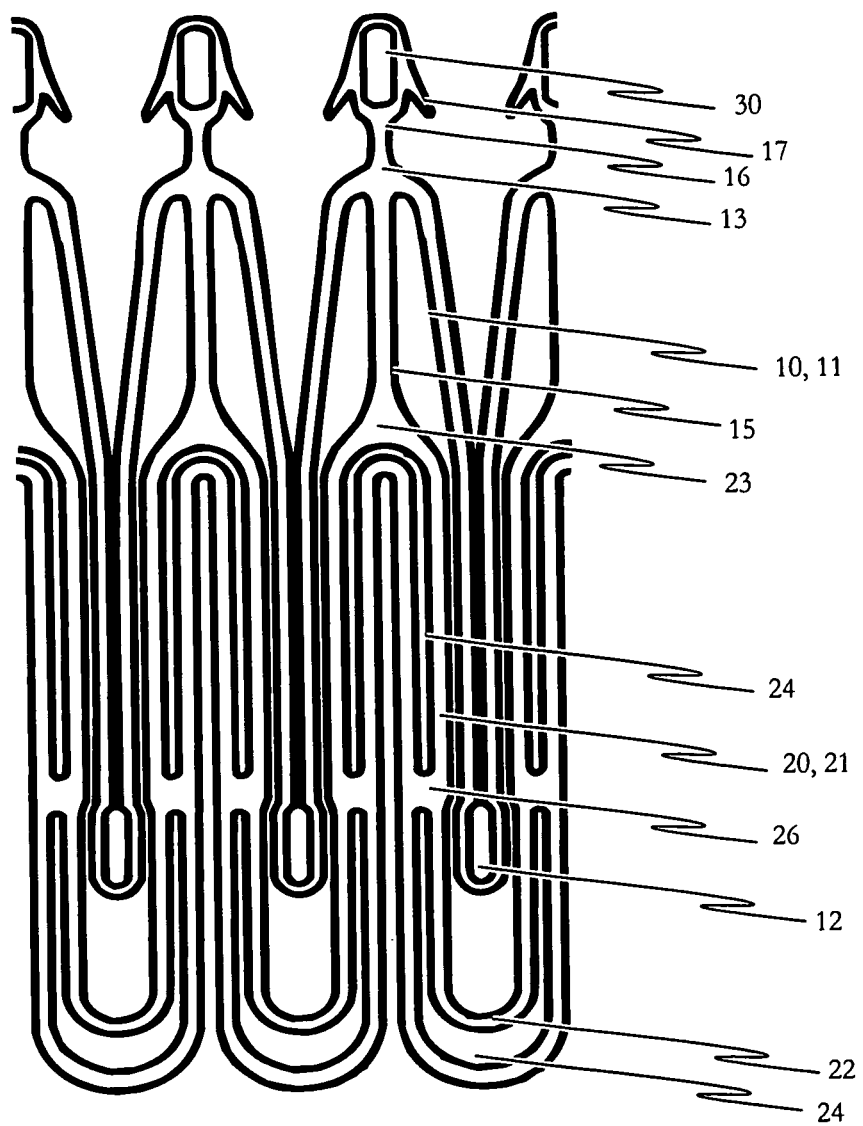
FIG. 4e is a flat projection of a cutting pattern which can be used for the production of the fourth, preferred, self-expandable endoprosthesis to cut the endoprosthesis illustrated in FIG. 4a integrally from a metal tube.

FIGS. 4a to 4c illustrate a fourth embodiment of a self-expandable endoprosthesis 1 for the medical device proposed by the invention. A fourth embodiment of the medical device proposed by the invention is illustrated in its expanded state with an endoprosthesis in FIG. 4c and an opened out heart valve prosthesis 40 attached to it is illustrated in FIG. 4d. FIG. 4e illustrates a flat projection of a cutting pattern which may be used for the production of the fourth embodiment of the self-expandable endoprosthesis 1. The cutting pattern illustrated in FIG. 4e is specifically suitable for cutting the endoprosthesis illustrated in FIG. 4a integrally from a metal tube.

The fourth embodiment of the self-expandable prosthesis 1 corresponds to a combination of the second and third embodiments described above. Specifically, the respective arms 11 of the adjacent positioning arches 10 are indirectly joined via the connecting web 16 extending essentially in the longitudinal direction of the endoprosthesis to the anchoring eye 30. Barbs 17 are provided on the respective anchoring eyes 30, the tips of which point in the direction of the proximal end 3 of the endoprosthesis 1. The advantages which can be achieved as a result of the features provided on the fourth embodiment were described above and will not be reiterated at this stage.

The fifth embodiment of a self-expandable endoprosthesis 1 and a medical device proposed by the invention illustrated in FIG. 5a to FIG. 5e essentially corresponds to the first embodiment described with reference to FIG. 1a to FIG. 1e, except that, in this instance, the respective retaining arches 21 of the endoprosthesis 1 are provided with reinforcing portions 26 which interrupt the slots 24 extending in the longitudinal direction of the retaining arches 21. The purpose of these reinforcing portions 26 is to open out the individual components of the retaining arches 21 and, in particular, to break the anchoring support 25 radially out of the retaining arches 20. Accordingly, a retaining portion for the stent 1 can be obtained with the reinforcing portions 26 which has no components which might explant the medical device when it is in the expanded state.

Figure 5A:
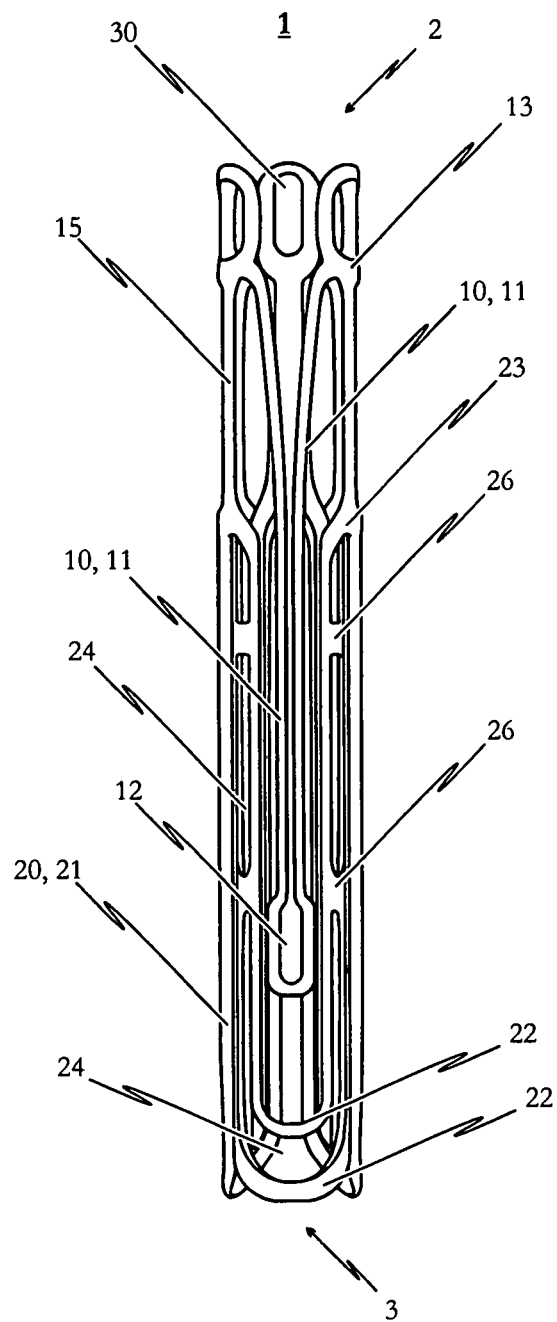
FIG. 5a shows a fifth preferred embodiment of a self-expandable endoprosthesis for the medical device proposed by the invention in its first, pre-determined mode in which the medical device is in its minimised state.
Figure 5B:
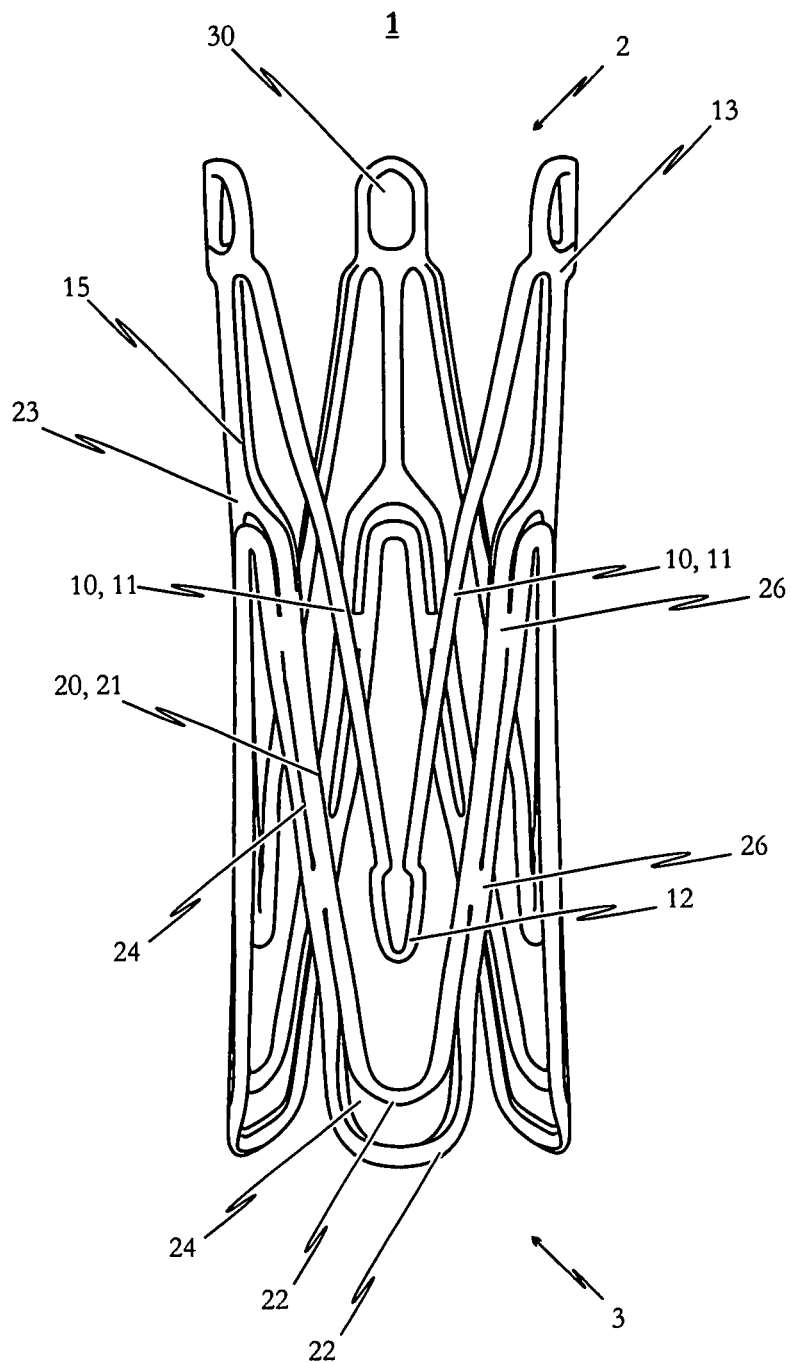
FIG. 5b shows the endoprosthesis illustrated in FIG. 5a in a state between its first, pre-definable mode and its second mode in which the medical device is in its expanded state.
Figure 5C:
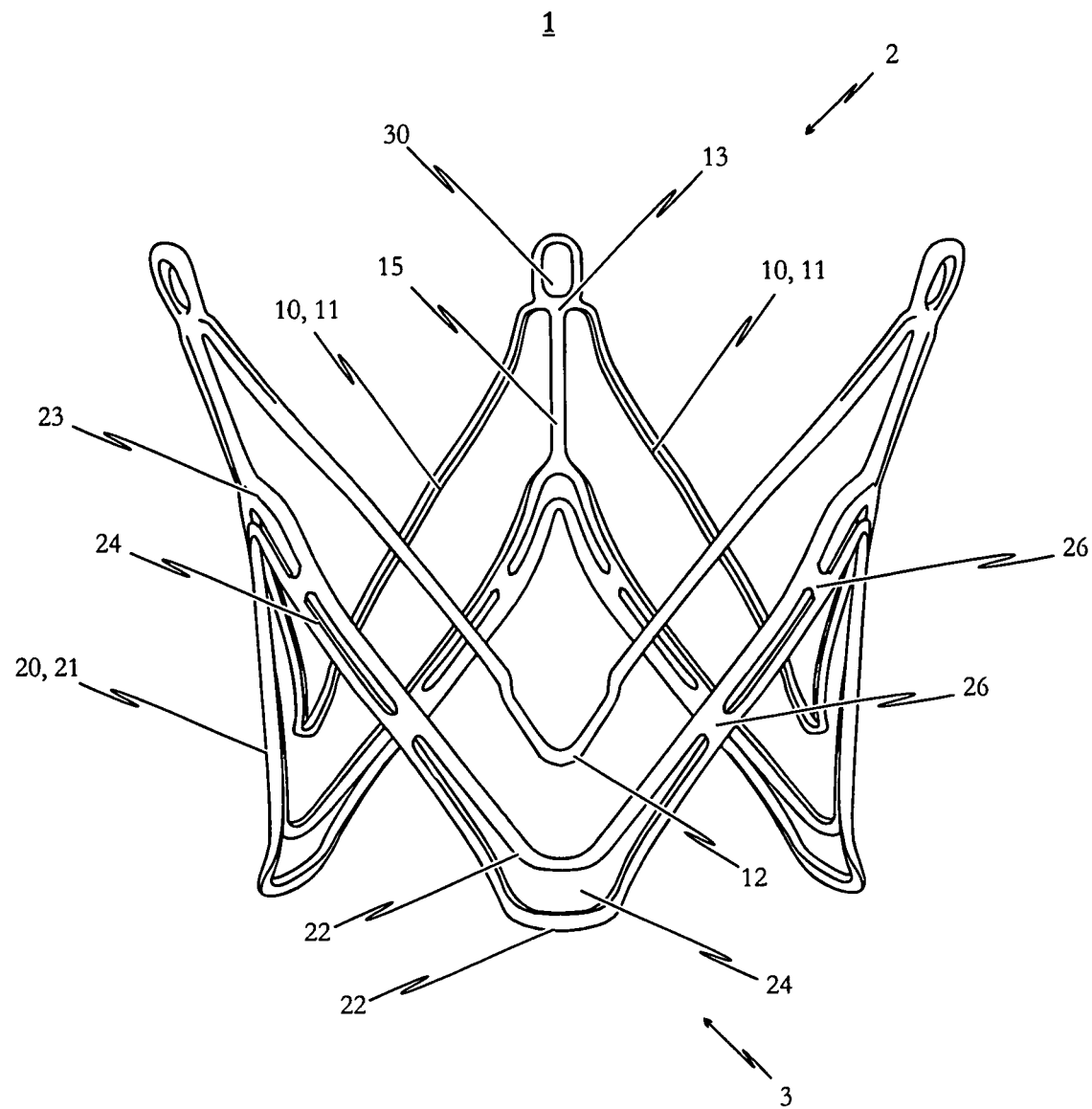
FIG. 5c shows the endoprosthesis illustrated in FIG. 5a in its second mode in which the medical device is in its expanded state.
Figure 5D:
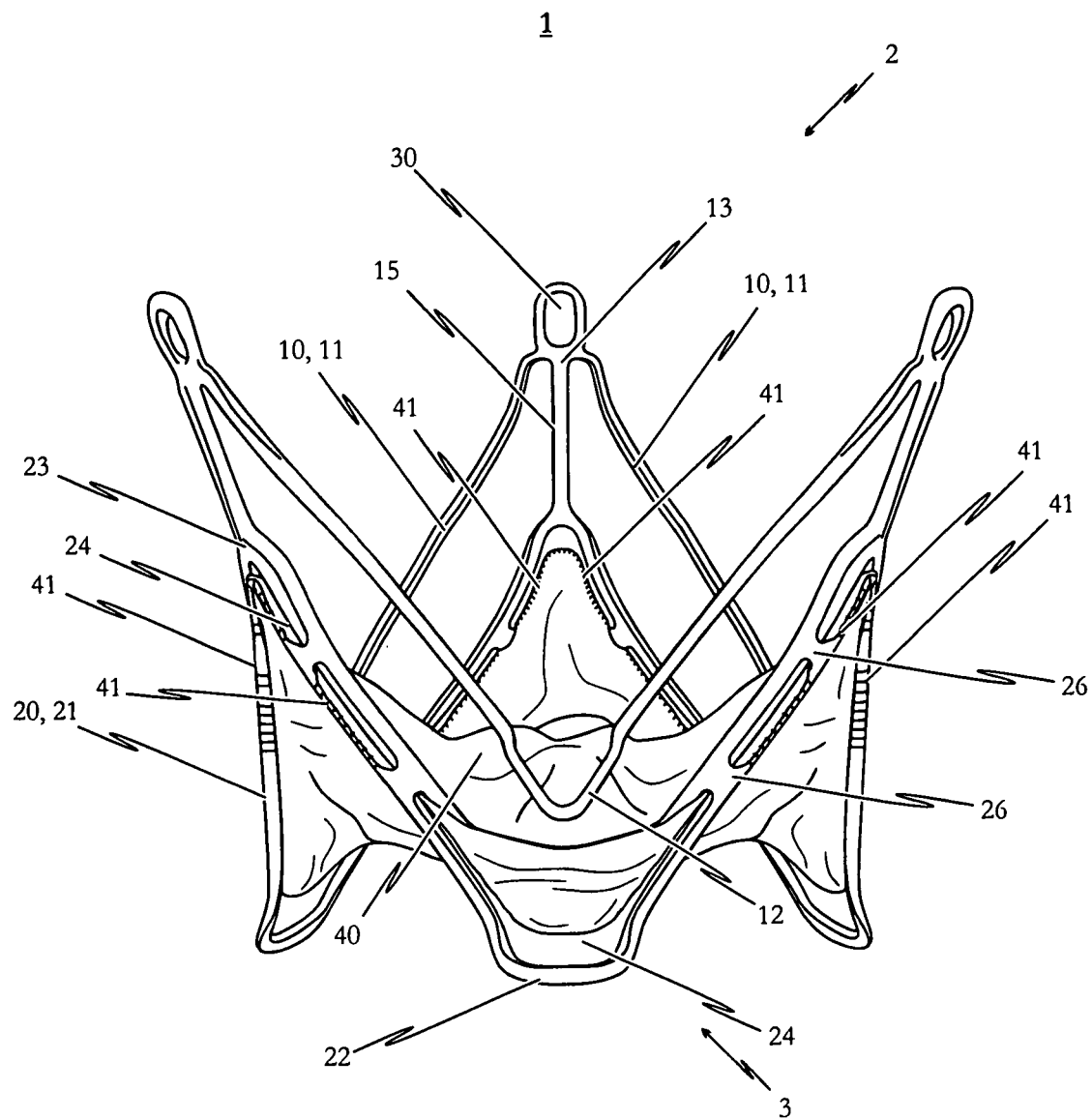
FIG. 5d illustrates a fifth preferred embodiment of the medical device proposed by the invention in its expanded state with an endoprosthesis of the type illustrated in FIG. 5c and a heart valve prosthesis attached to it and opened out.
Figure 5E:
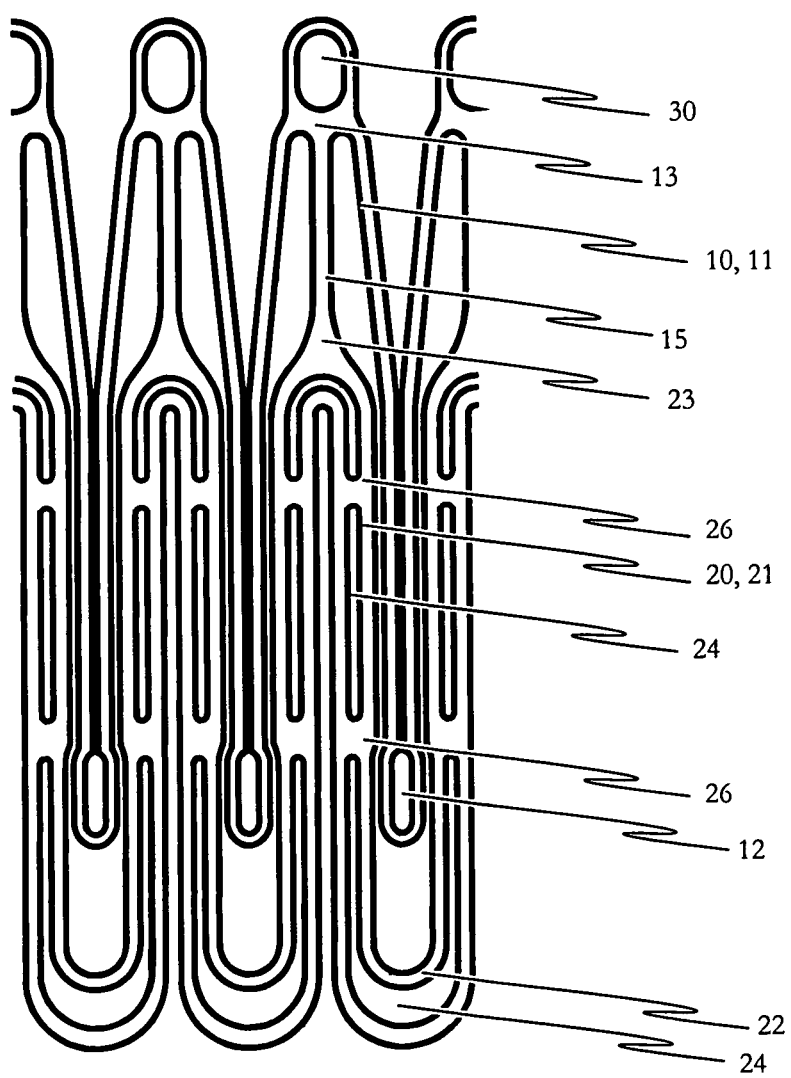
FIG. 5e is a flat projection of a cutting pattern which can be used for the production of the fifth, preferred, self-expandable endoprosthesis to cut the endoprosthesis illustrated in FIG. 5a integrally from a metal tube.
Figure 6A:
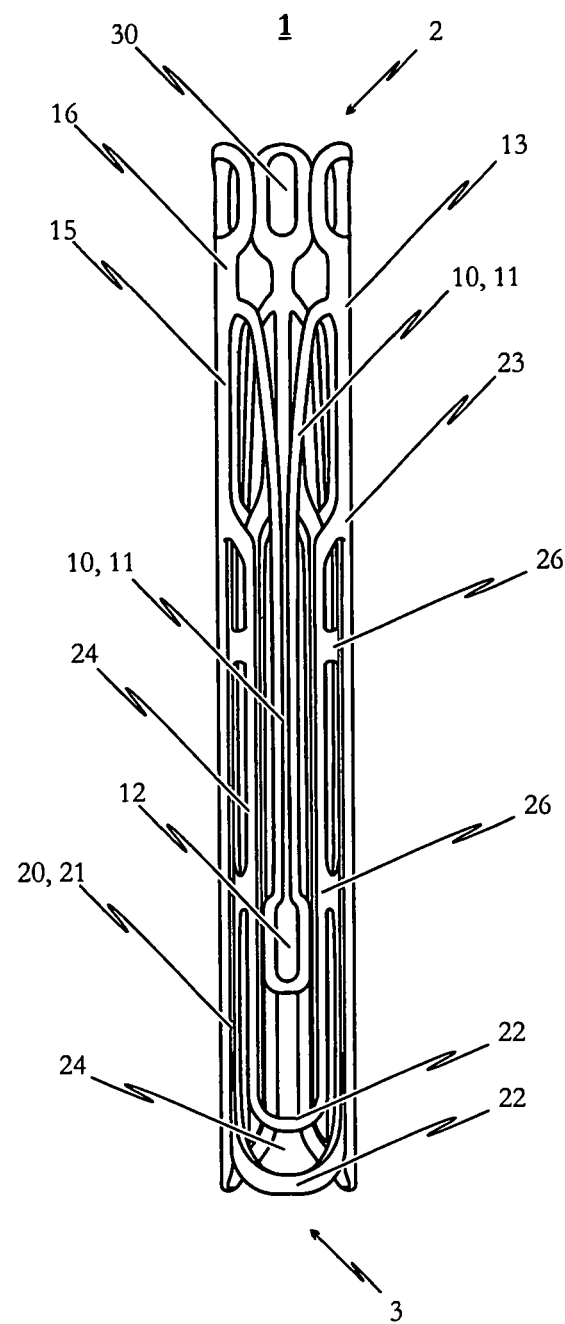
FIG. 6a shows a sixth preferred embodiment of a self-expandable endoprosthesis for the medical device proposed by the invention in its first, pre-determined mode in which the medical device is in its minimised state.
Figure 6B:
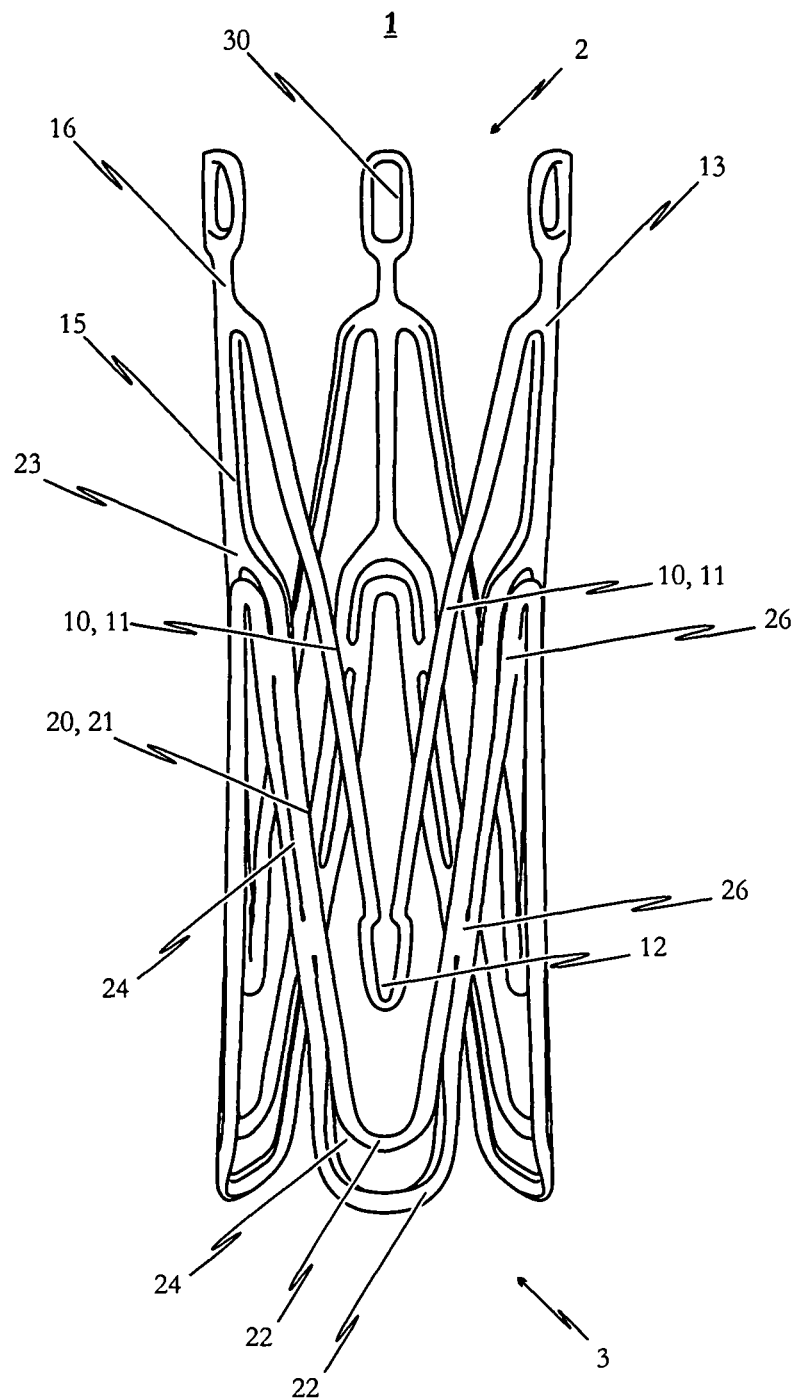
FIG. 6b shows the endoprosthesis illustrated in FIG. 6a in a state between its first, pre-definable mode and its second mode in which the medical device is in its expanded state.
Figure 6C:
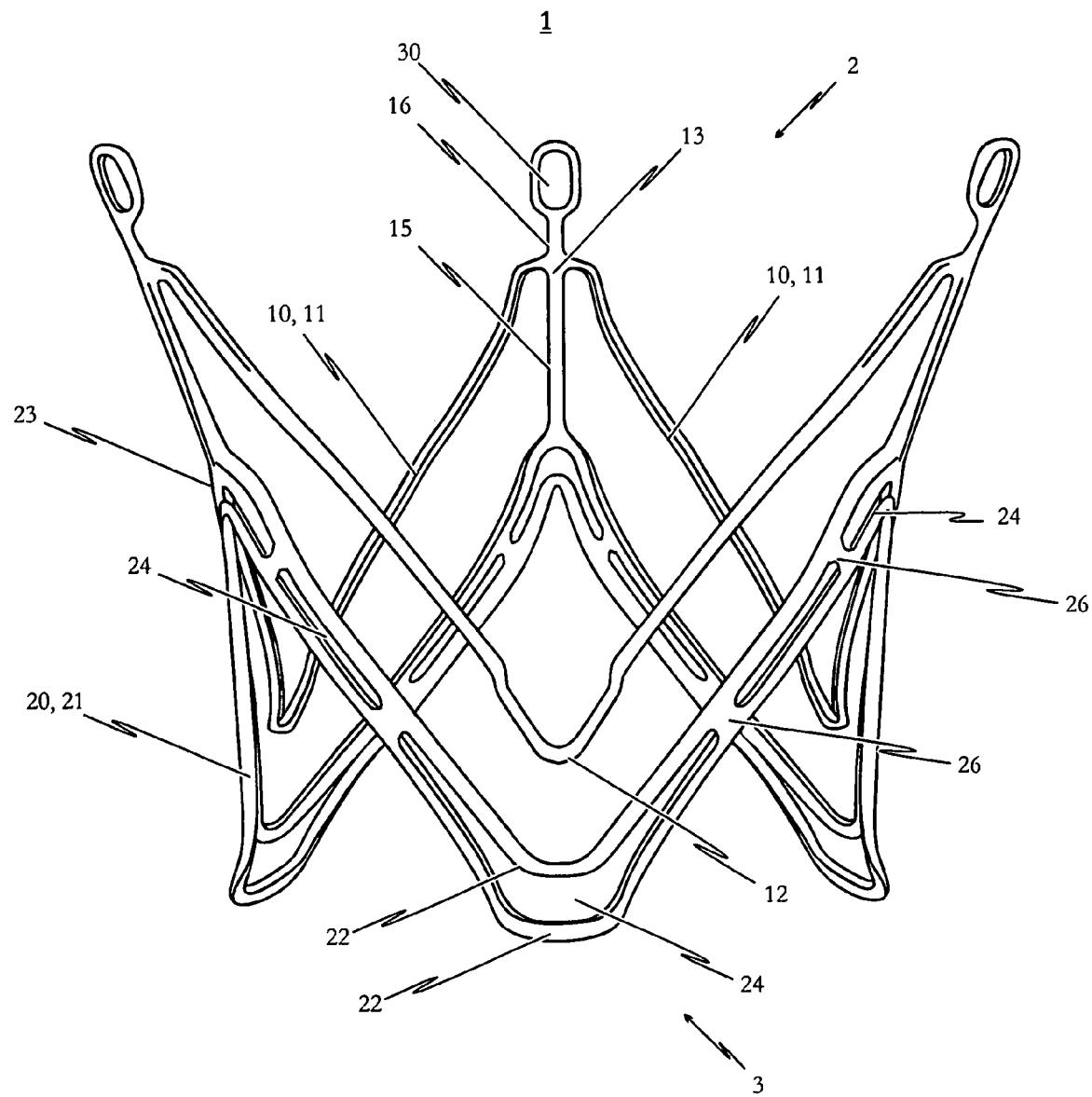
FIG. 6c shows the endoprosthesis illustrated in FIG. 6a in its second mode in which the medical device is in its expanded state.
Figure 6D:
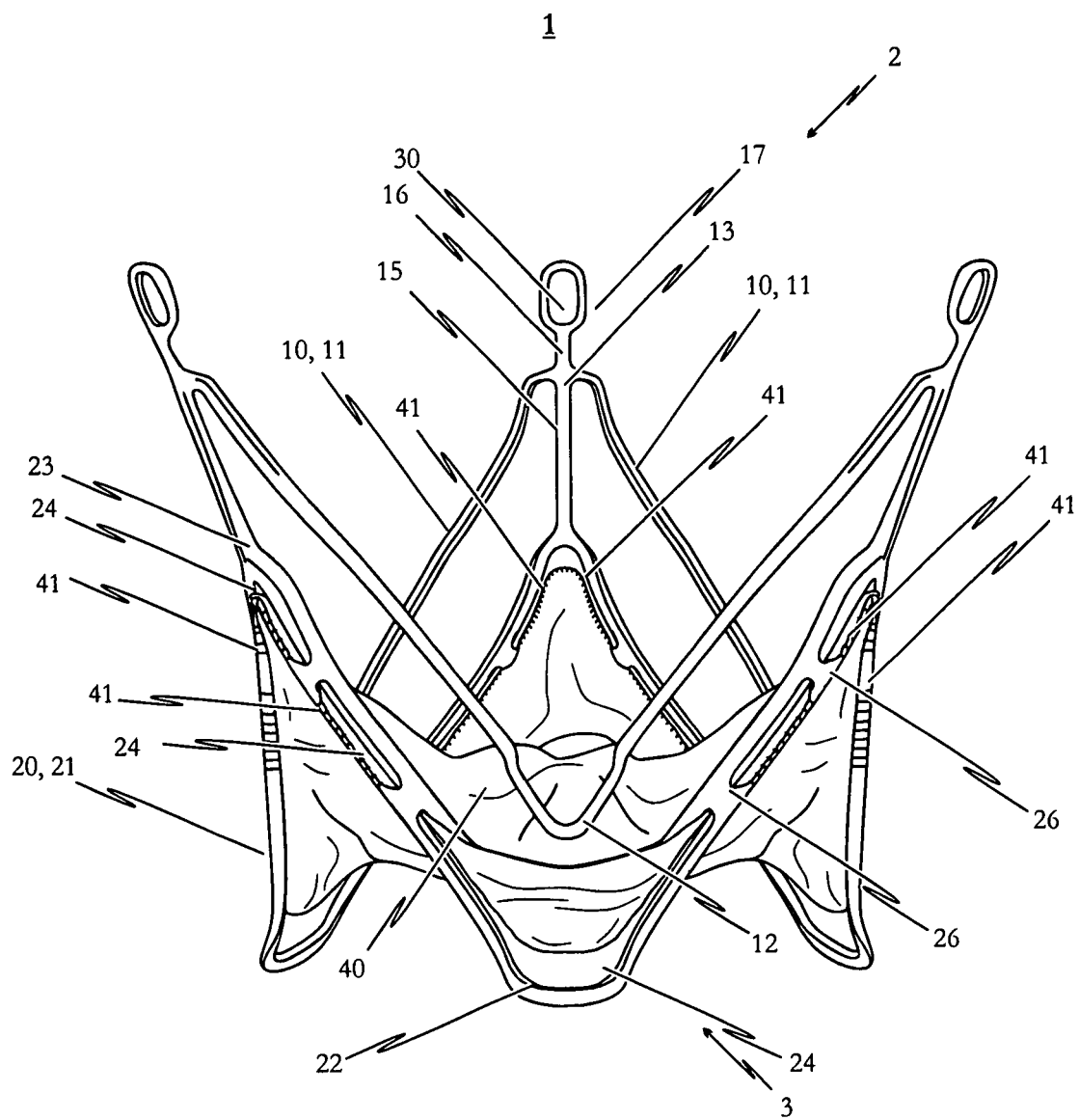
FIG. 6d illustrates a sixth preferred embodiment of the medical device proposed by the invention in its expanded state with an endoprosthesis of the type illustrated in FIG. 6c and a heart valve prosthesis attached to it and opened out.
Figure 6E:
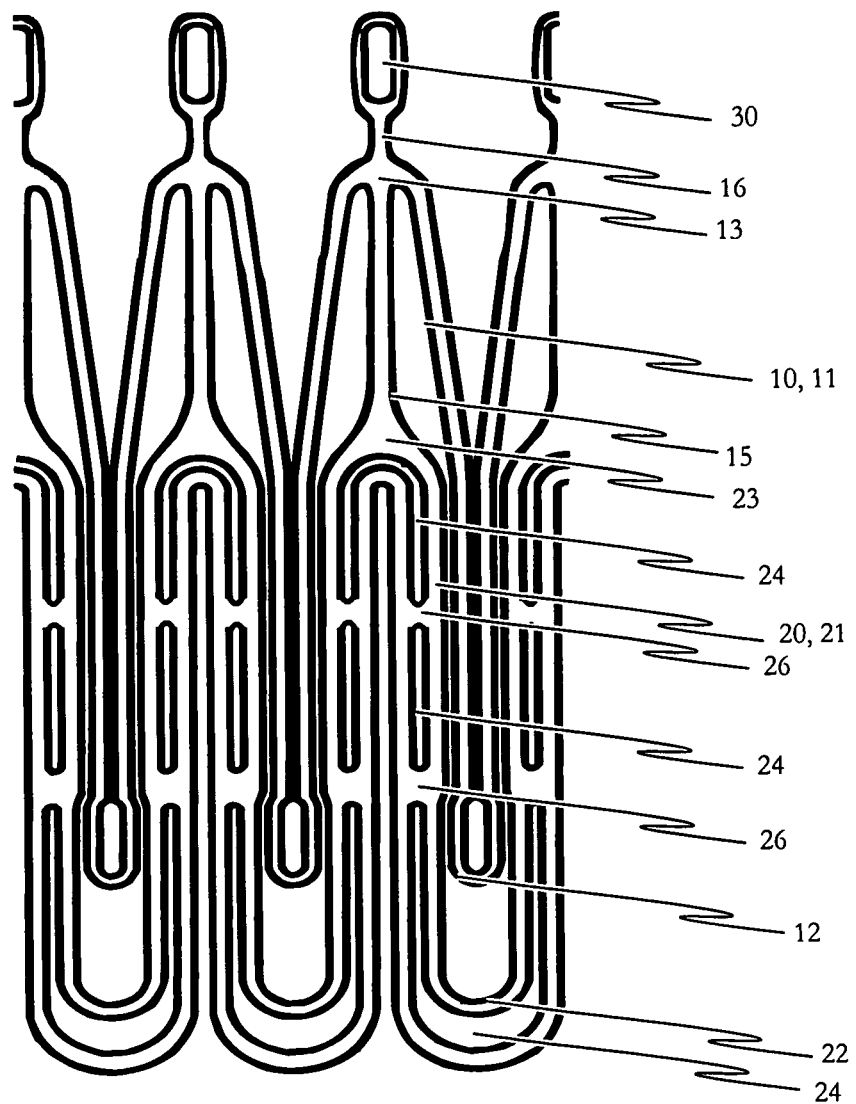
FIG. 6e is a flat projection of a cutting pattern which can be used for the production of the sixth, preferred, self-expandable endoprosthesis to cut the endoprosthesis illustrated in FIG. 6a integrally from a metal tube.
Figure 7A:
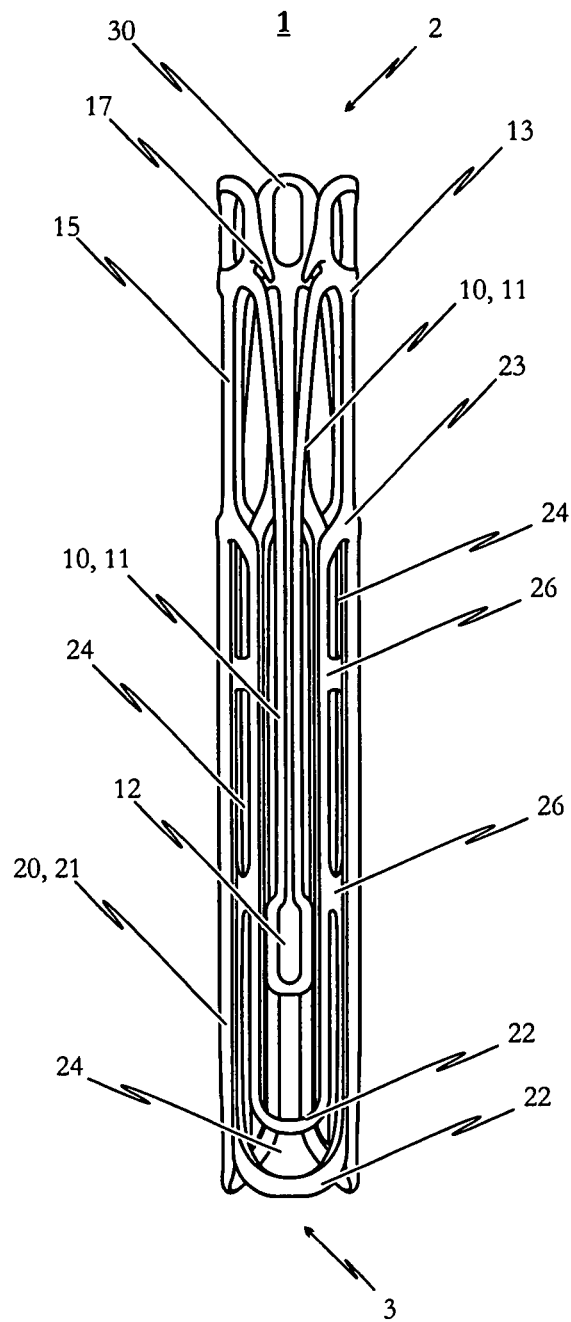
FIG. 7a shows a seventh, preferred embodiment of a self-expandable endoprosthesis for the medical device proposed by the invention in its first, pre-determined mode in which the medical device is in its minimised state.
Figure 7B:
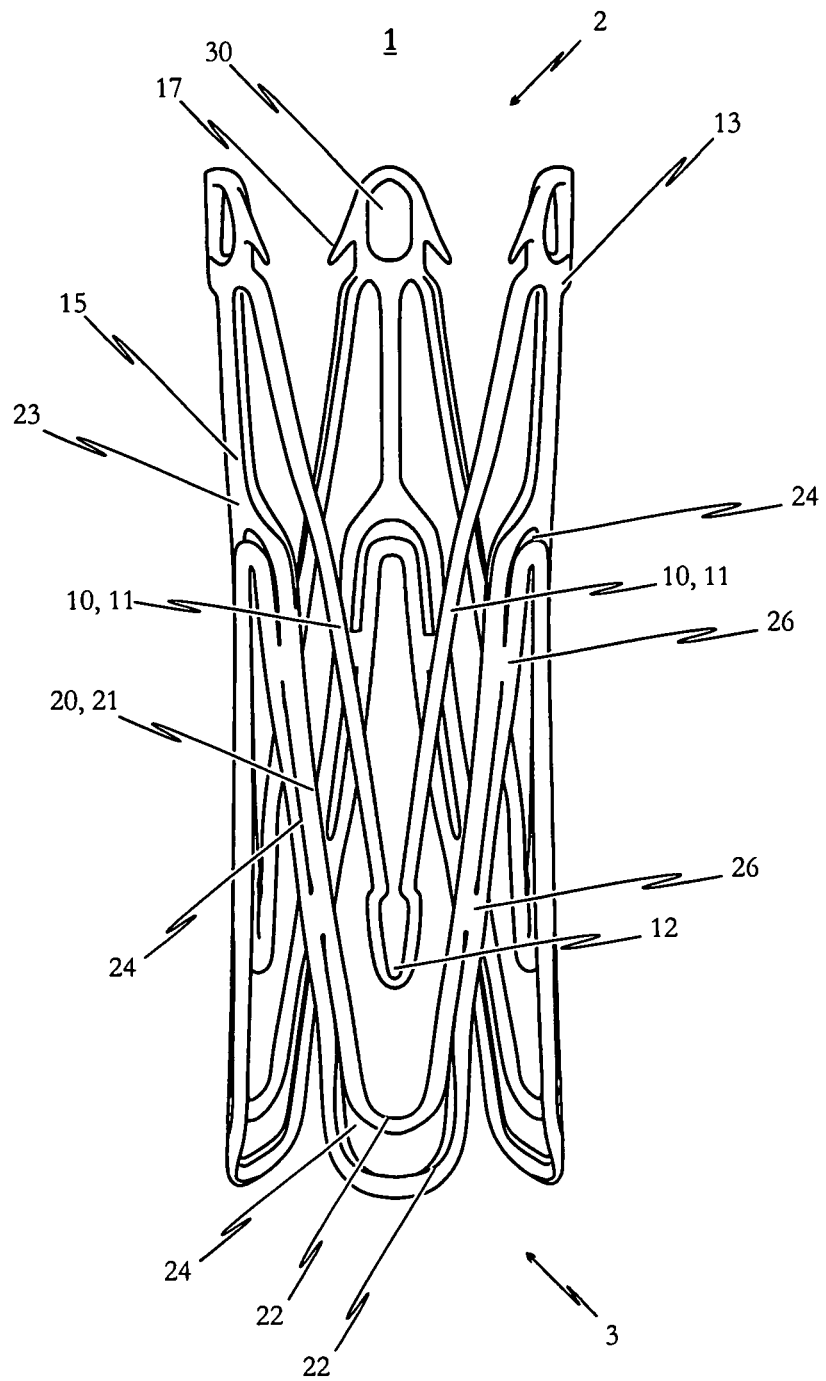
FIG. 7b shows the endoprosthesis illustrated in FIG. 7a in a state between its first, pre-definable mode and its second mode in which the medical device is in its expanded state.
Figure 7C:
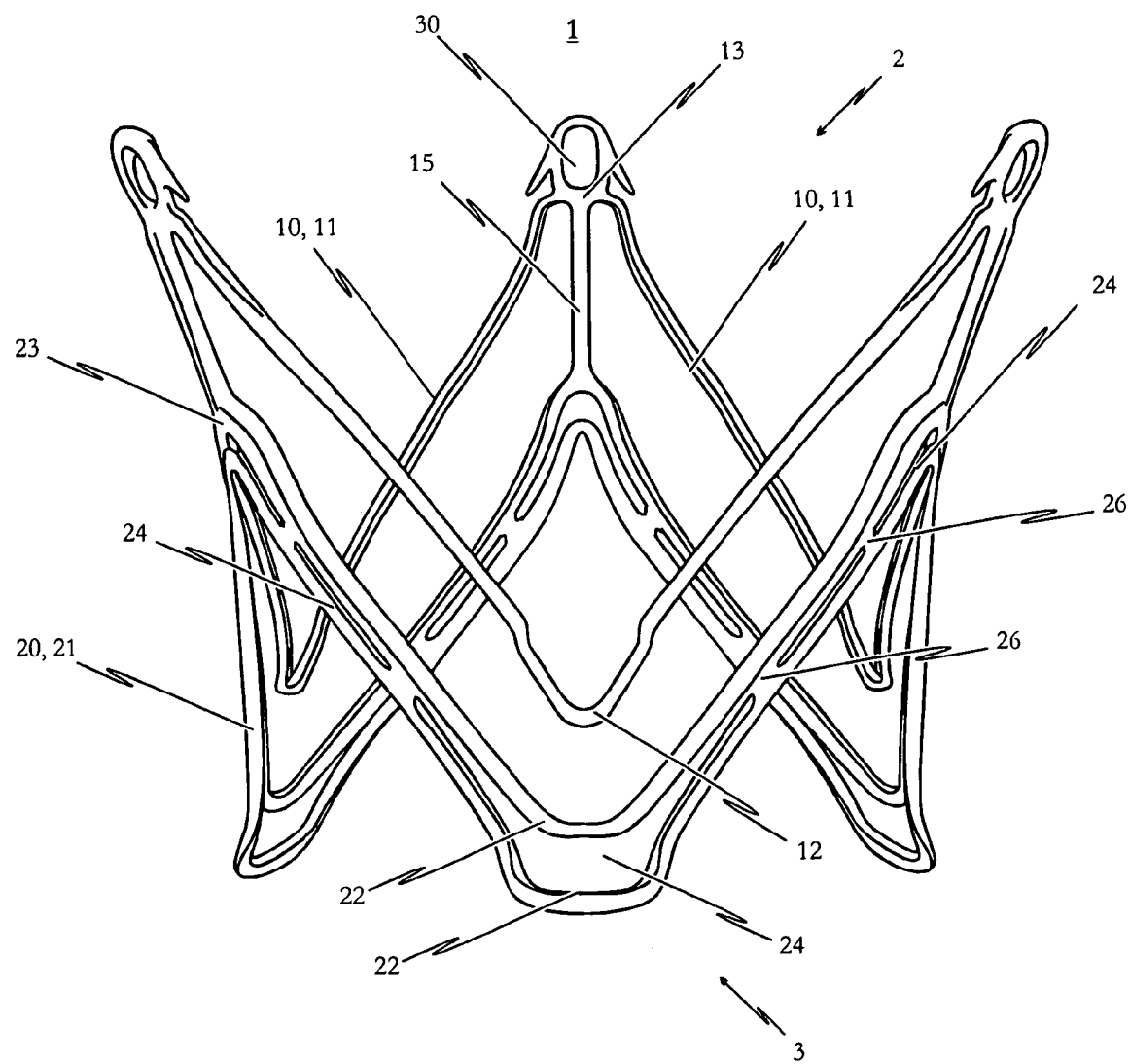
FIG. 7c shows the endoprosthesis illustrated in FIG. 7a in its second mode in which the medical device is in its expanded state.
Figure 7D:
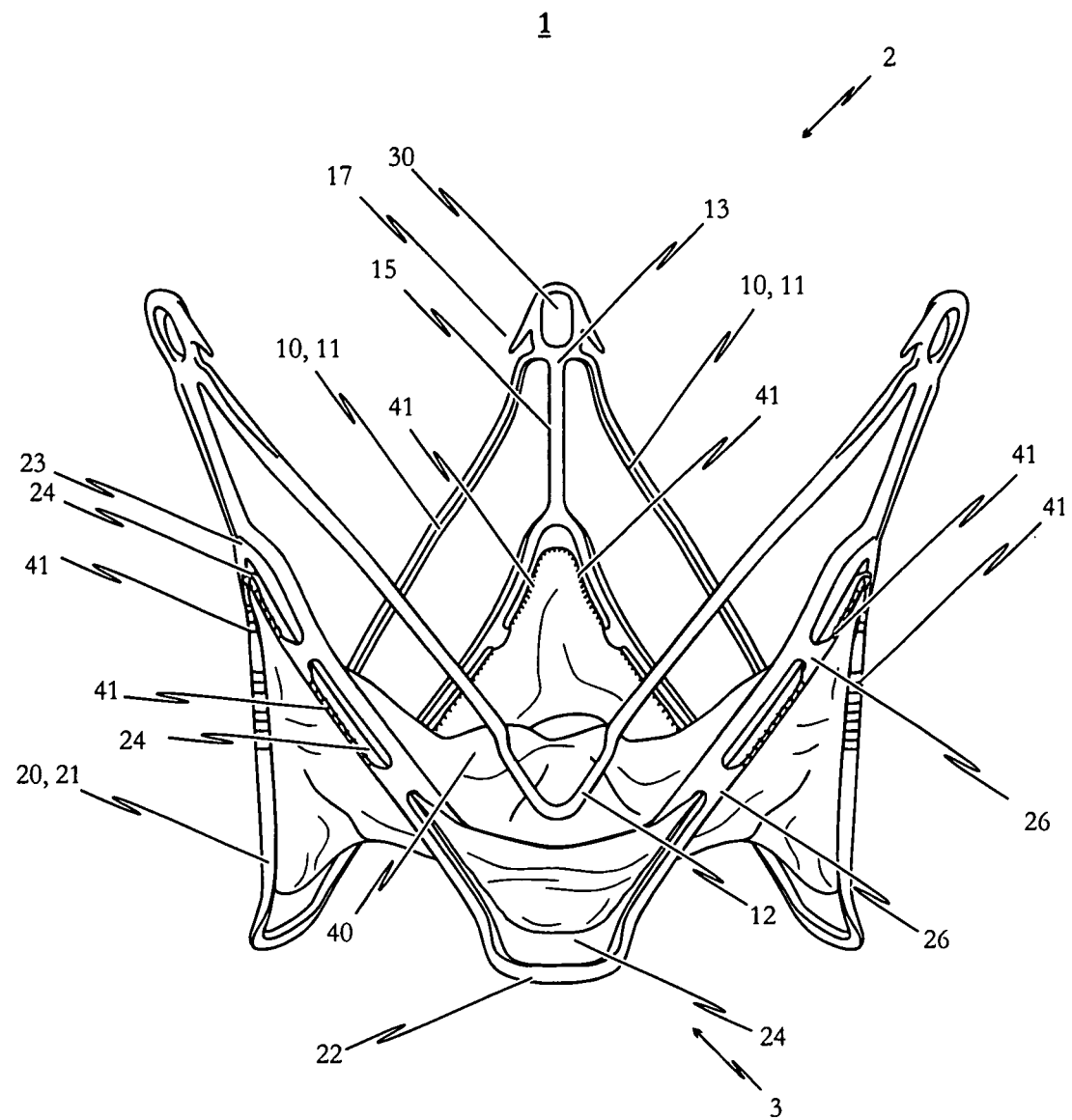
FIG. 7d illustrates a seventh preferred embodiment of the medical device proposed by the invention in its expanded state with an endoprosthesis of the type illustrated in FIG. 7c and a heart valve prosthesis attached to it and opened out.
Figure 7E:
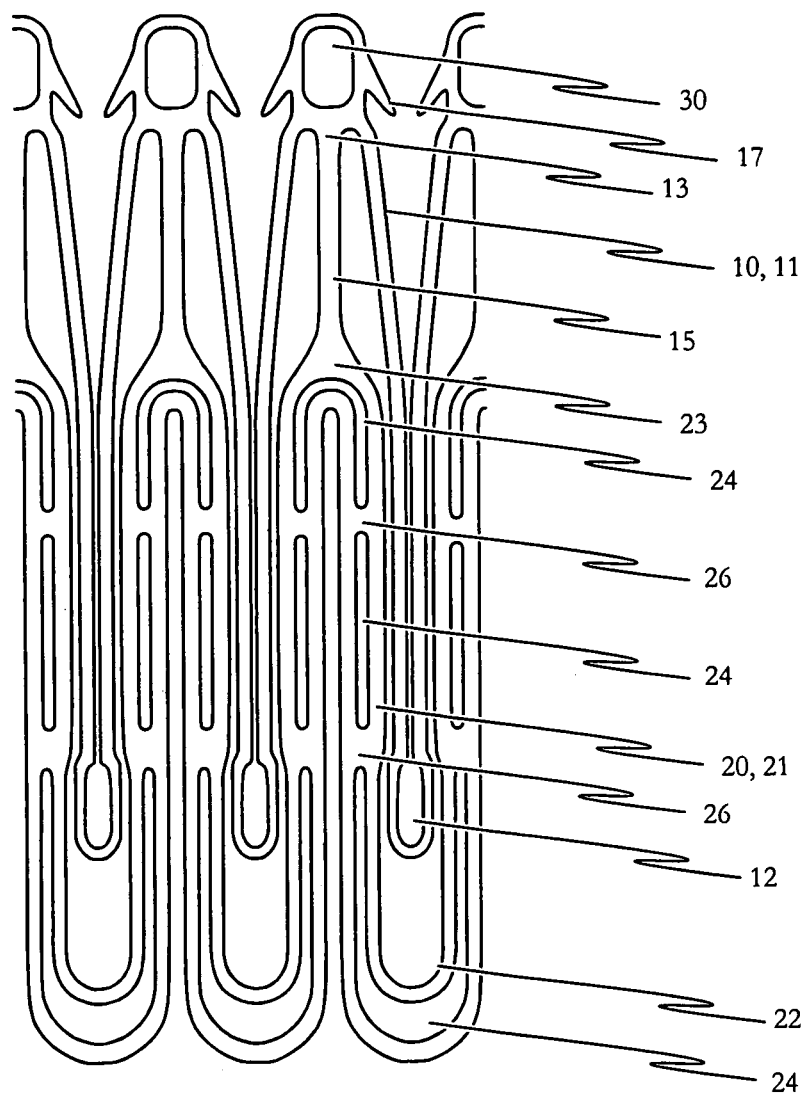
FIG. 7e is a flat projection of a cutting pattern which can be used for the production of the seventh preferred, self-expandable endoprosthesis to cut the endoprosthesis illustrated in FIG. 7a integrally from a metal tube.
Figure 8A:
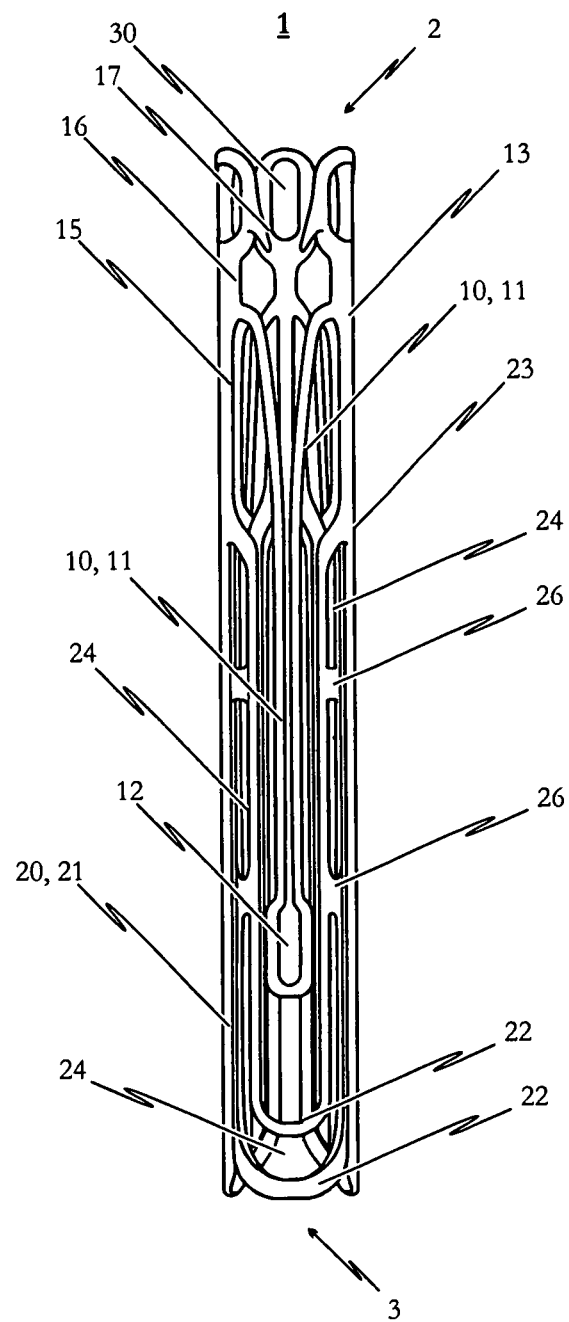
FIG. 8a shows an eighth, preferred embodiment of a self-expandable endoprosthesis for the medical device proposed by the invention in its first, pre-determined mode in which the medical device is in its minimised state.
Figure 8B:
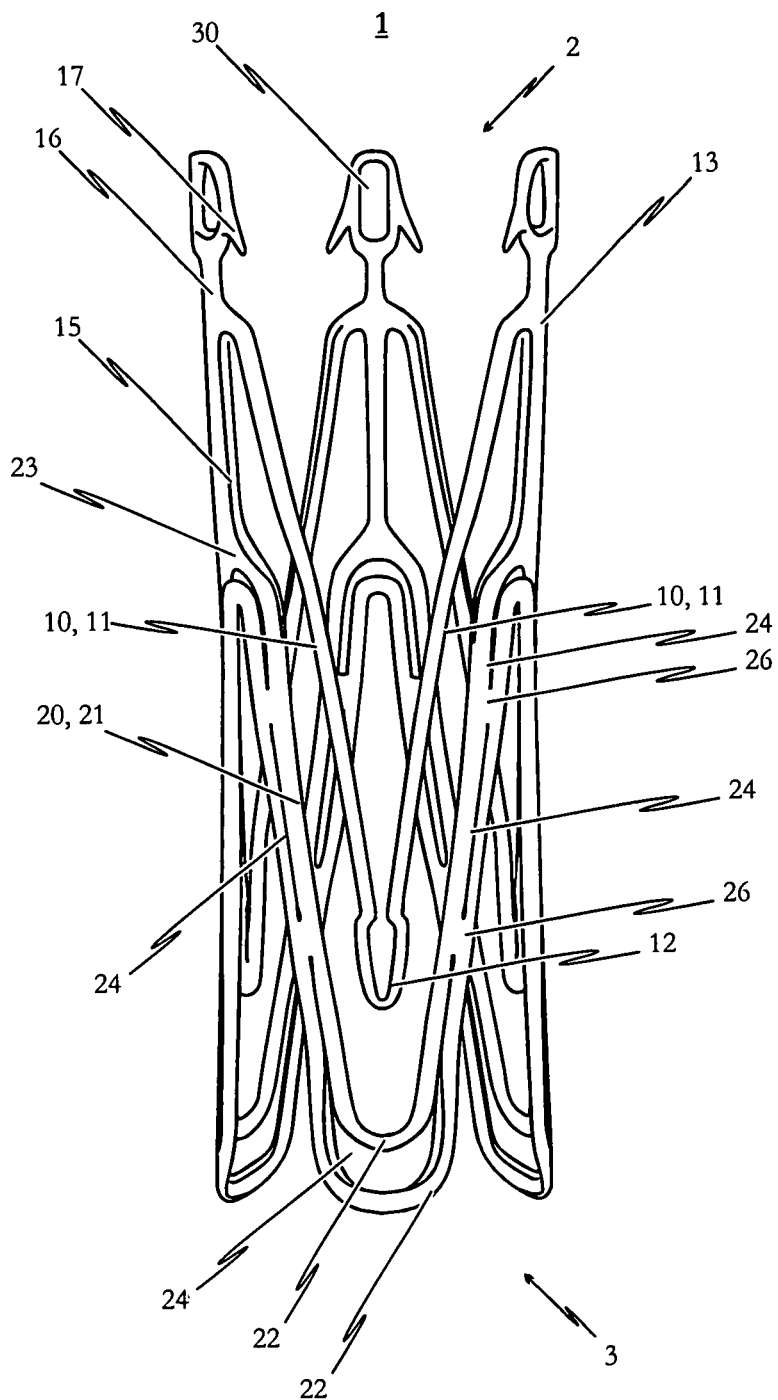
FIG. 8b shows the endoprosthesis illustrated in FIG. 8a in a state between its first, pre-definable mode and its second mode in which the medical device is in its expanded state.
Figure 8C:
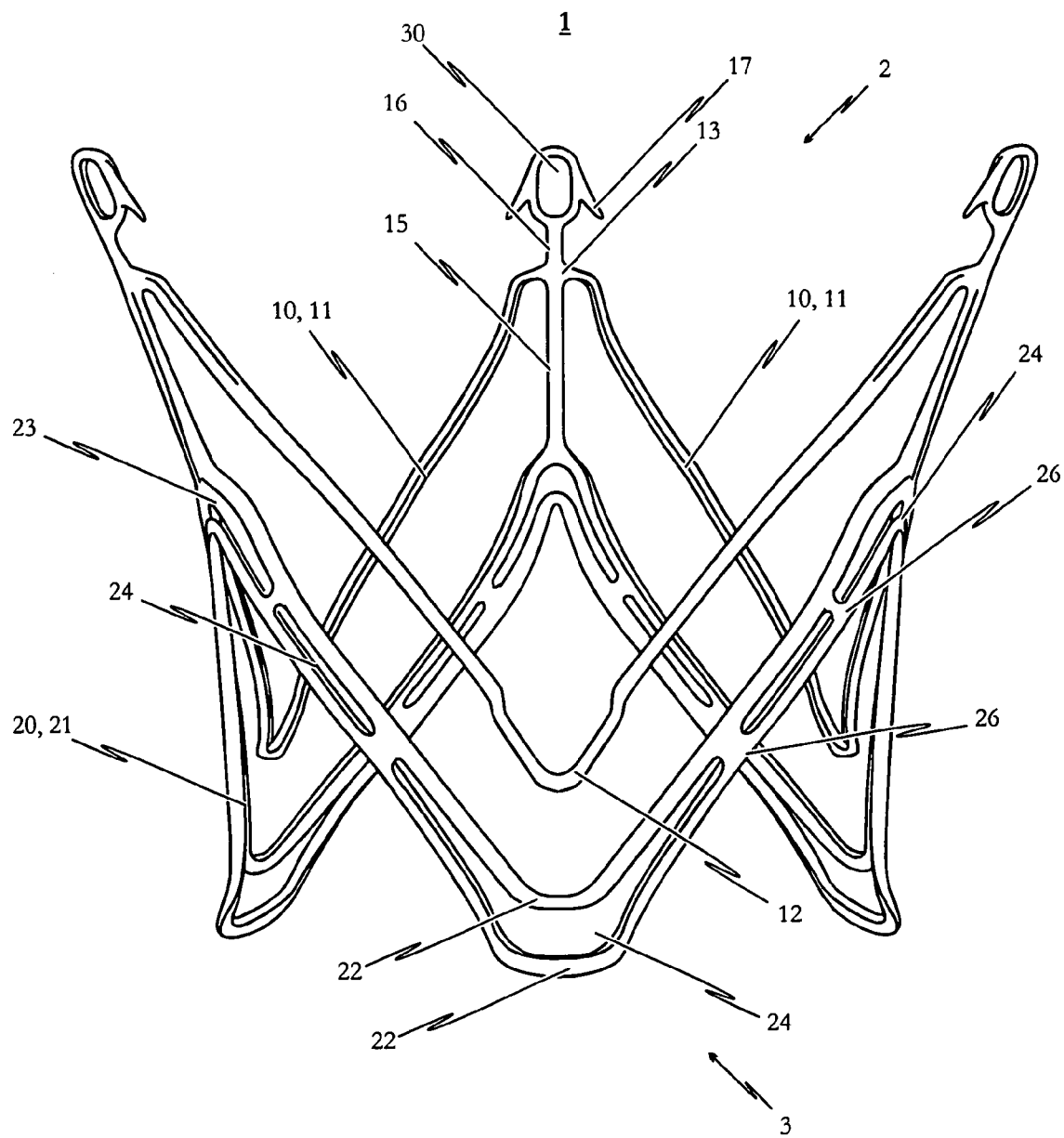
FIG. 8c shows the endoprosthesis illustrated in FIG. 8a in its second mode in which the medical device is in its expanded state.
Figure 8D:
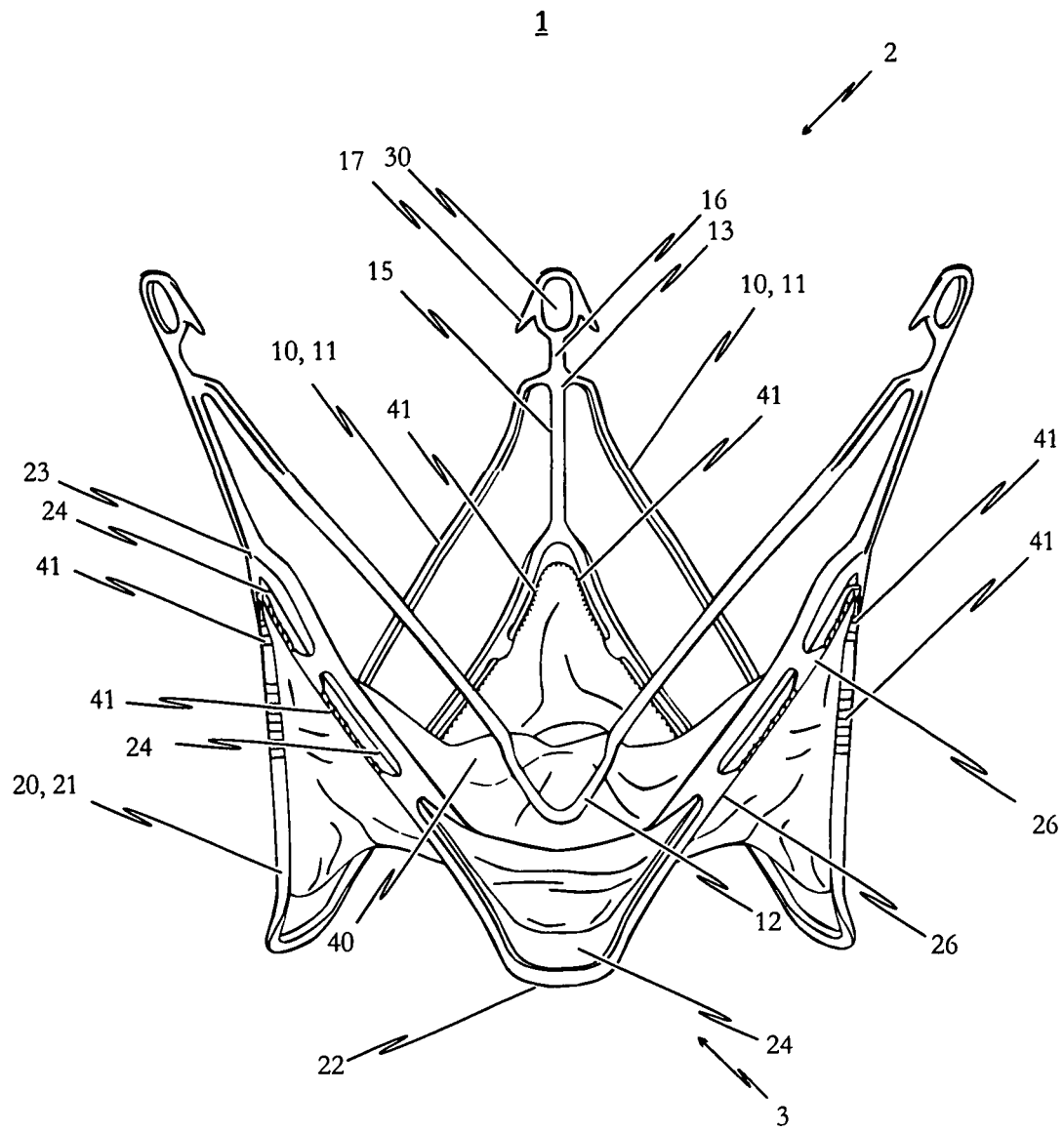
FIG. 8d illustrates an eighth preferred embodiment of the medical device proposed by the invention in its expanded state with an endoprosthesis of the type illustrated in FIG. 8c and a heart valve prosthesis attached to it and opened out.
Figure 8E:
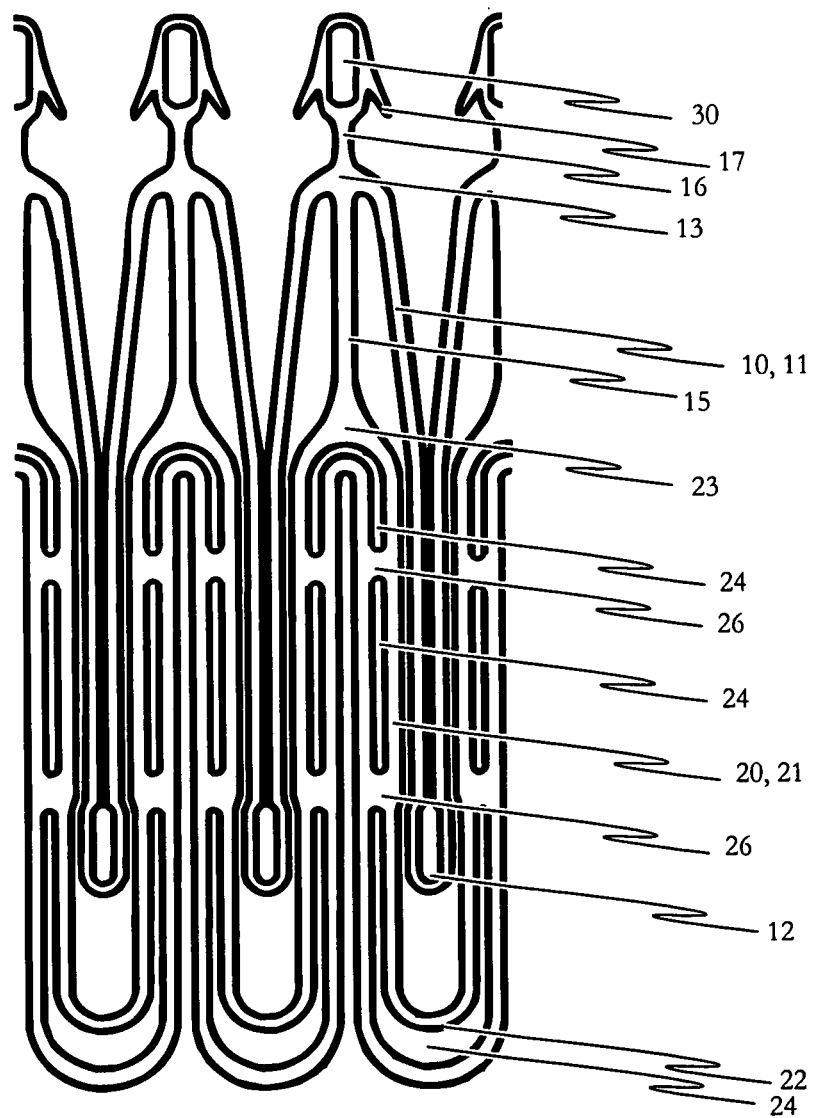
FIG. 8e is a flat projection of a cutting pattern which can be used for the production of the eighth preferred, self-expandable endoprosthesis to cut the endoprosthesis illustrated in FIG. 8a integrally from a metal tube.

FIG. 5e illustrates a flat projection of a cutting pattern which may be used for production of the fifth embodiment of the self-expandable endoprosthesis 1 to cut the endoprosthesis 1 illustrated in FIG. 5a integrally from a metal tube.

The sixth embodiment of the self-expandable endoprosthesis and the medical device proposed by the invention illustrated in FIGS. 6a to 6e corresponds to a combination of the second embodiment illustrated in FIGS. 2a to 2e and the fifth embodiment described above with reference to FIGS. 5a to 5e. Specifically, therefore, the endoprosthesis 1 based on the second embodiment is provided with additional reinforcing portions 26 at the respective retaining arches 21 which interrupt the slots 24 extending in the longitudinal direction of the retaining arches 21.

The seventh embodiment of the endoprosthesis 1 and the medical device proposed by the invention illustrated in FIGS. 7a to 7e corresponds to a combination of the third and fifth embodiments described above. In particular the respective retaining eyes 30 are provided with barbs 17 and the respective retaining arches 21 are provided with reinforcing portions 26.

The eighth embodiment of the self-expandable endoprosthesis and the medical device proposed by the invention illustrated in FIGS. 8a to 8e corresponds to a combination of the fourth and fifth embodiments, in which case the respective retaining arches 21 are provided with reinforcing portions 26. The retaining eyes 30 provided with barbs 17 are connected to the respective arms 11 of the adjacent positioning arches 10 by means of a connecting web 16 extending essentially in the longitudinal direction of the endoprosthesis 1.

Figure 9A:
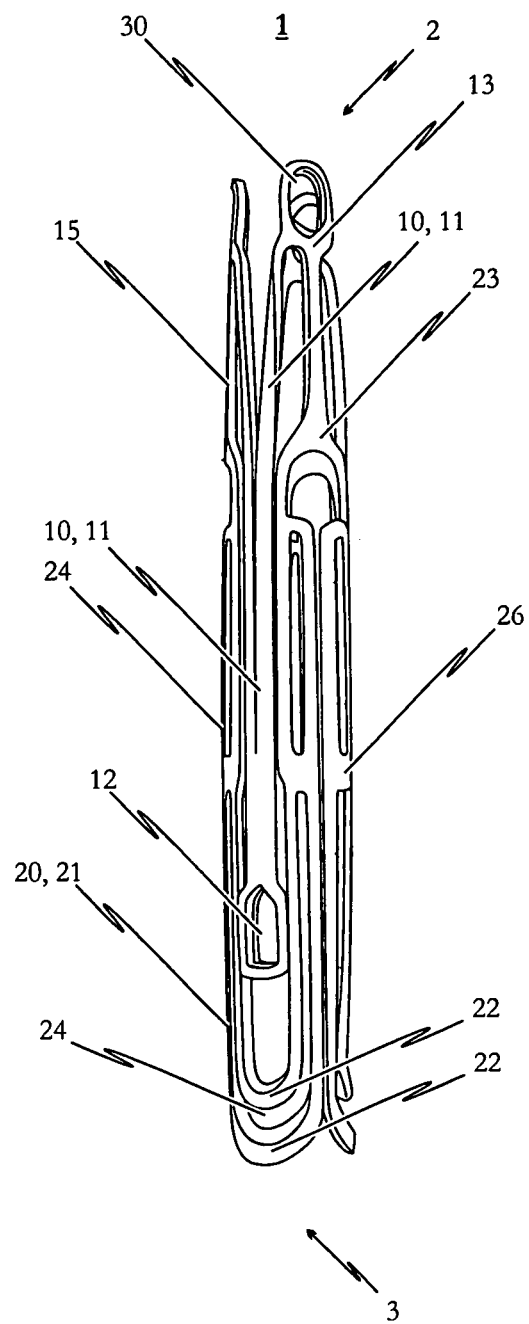
FIG. 9a shows a ninth, preferred embodiment of a self-expandable endoprosthesis for the medical device proposed by the invention in its first, pre-determined mode in which the medical device is in its minimised state.
Figure 9B:
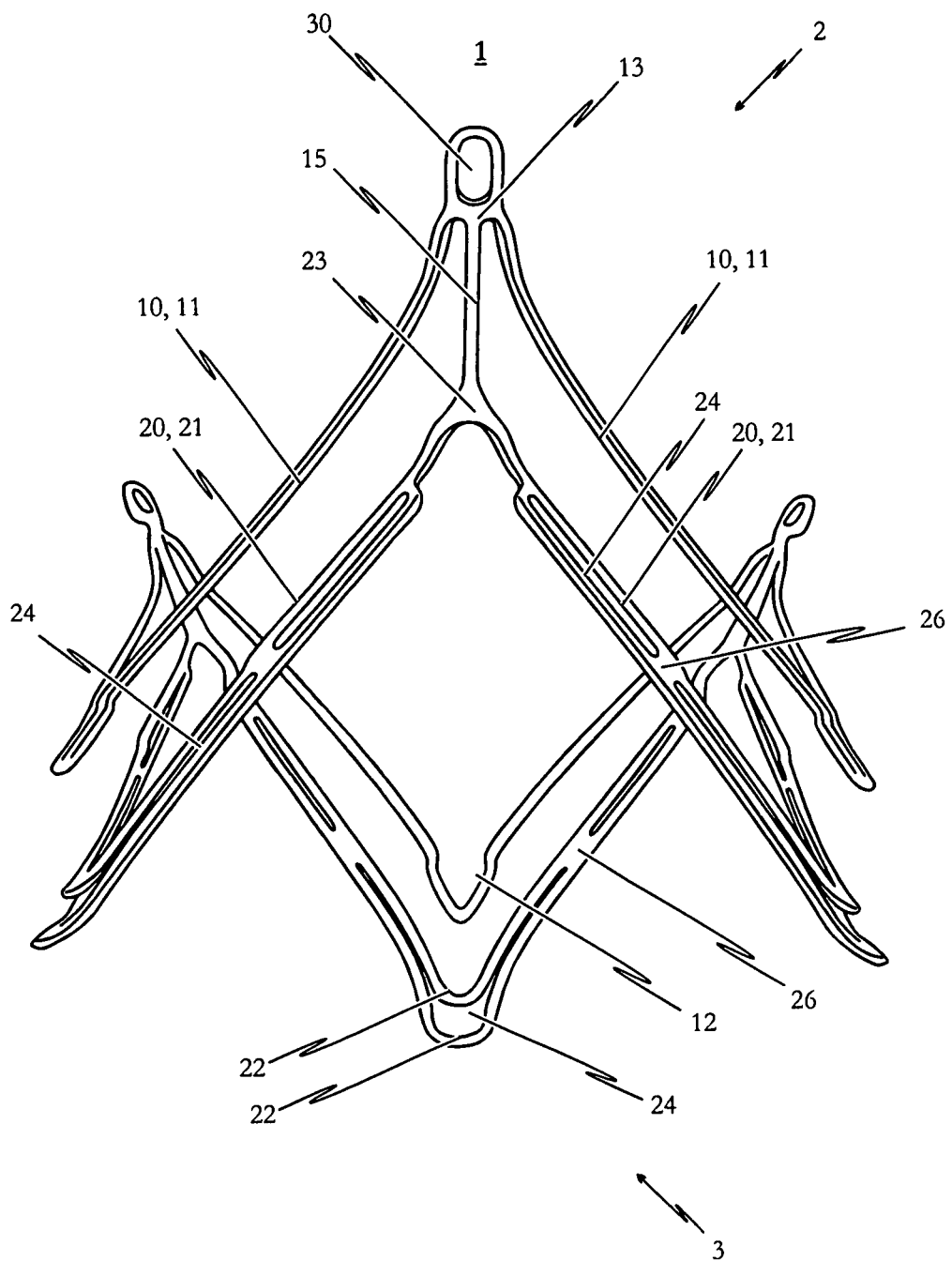
FIG. 9b is a perspective side view of a connecting web between an end portion of a positioning arch and an end portion of an associated retaining arch of the endoprosthesis illustrated in FIG. 9a in its second mode in which the medical device is in its expanded state.
Figure 9C:
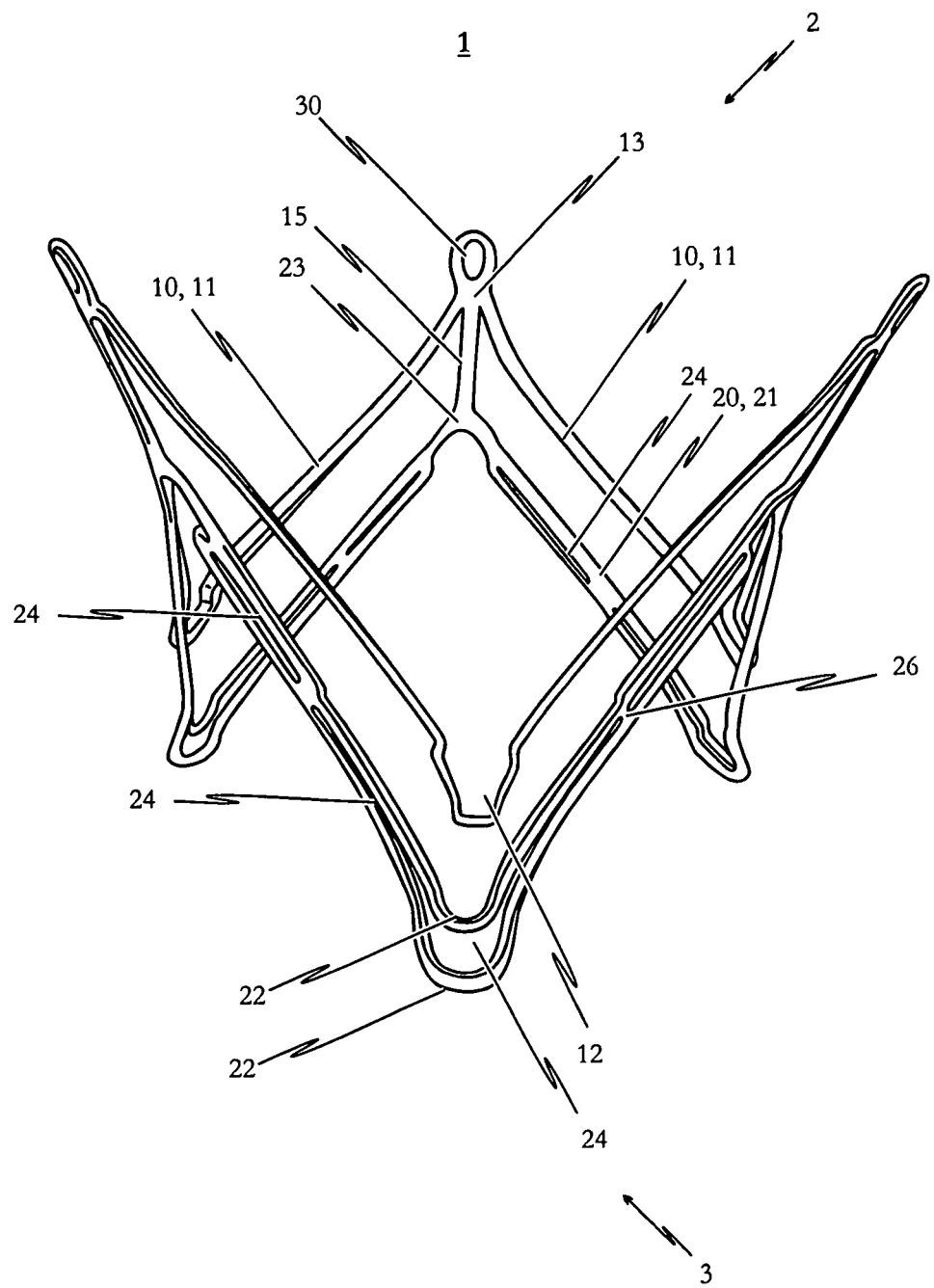
FIG. 9c is a perspective side view of a positioning arch and the associated retaining arch of the endoprosthesis illustrated in FIG. 9a in its second mode in which the medical device is in its expanded state.
Figure 9D:
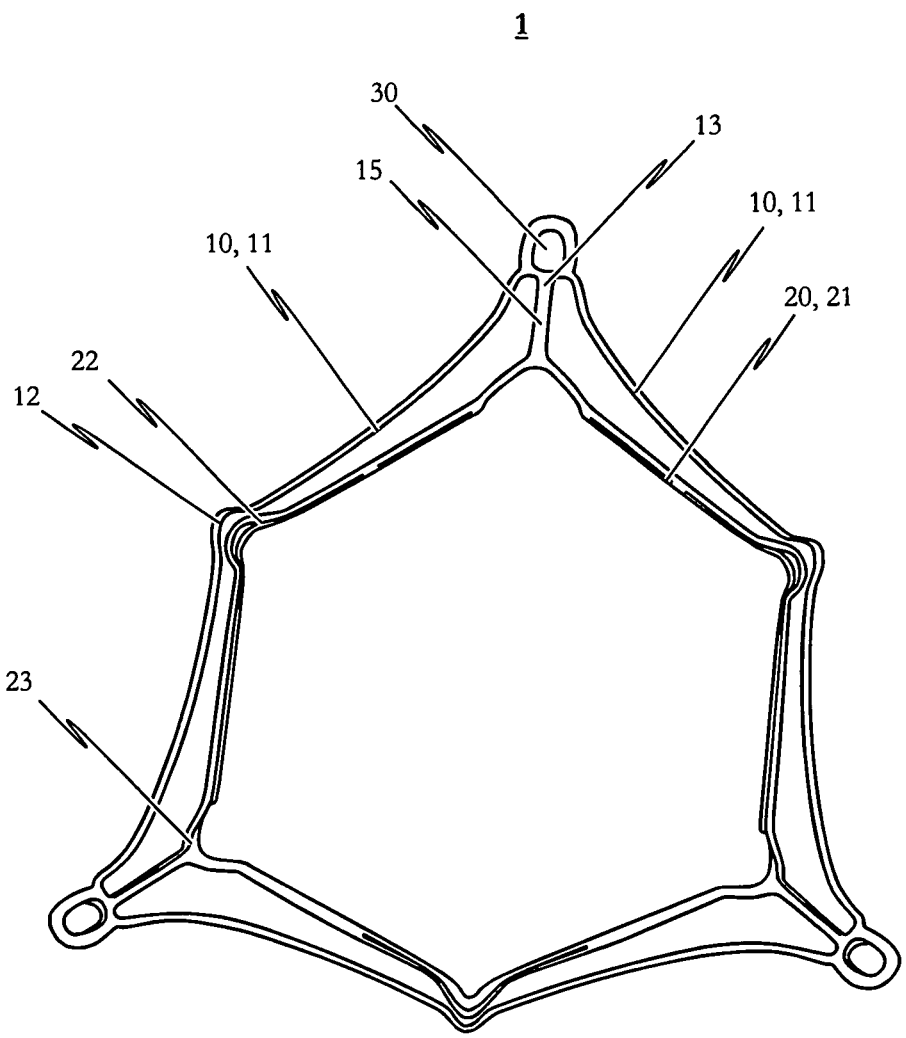
FIG. 9d is a perspective plan view of the distal region of the endoprosthesis illustrated in FIG. 9a in its second mode in which the medical device is in its expanded state.

The ninth embodiment of the self-expandable endoprosthesis for the medical device proposed by the invention illustrated in FIGS. 9a to 9d is of a slightly modified shape compared with the first embodiment (see FIGS. 1a to 1c). The endoprosthesis 1 based on the ninth embodiment is illustrated in its first pre-defined mode in FIG. 9a. FIGS. 9b and 9c respectively show a perspective side view of the endoprosthesis 1 based on the ninth embodiment in its second mode. Specifically, the connecting web 15 between the end portion 13 of a positioning arch 10, 11 and the end portion 23 of an associated retaining arch 20, 21 is illustrated in FIG. 9b. FIG. 9c, on the other hand, illustrates the positioning arches 10, 11 and the associated retaining arches 20, 21 of the endoprosthesis 1 illustrated in FIG. 9a.

Figure 9E:
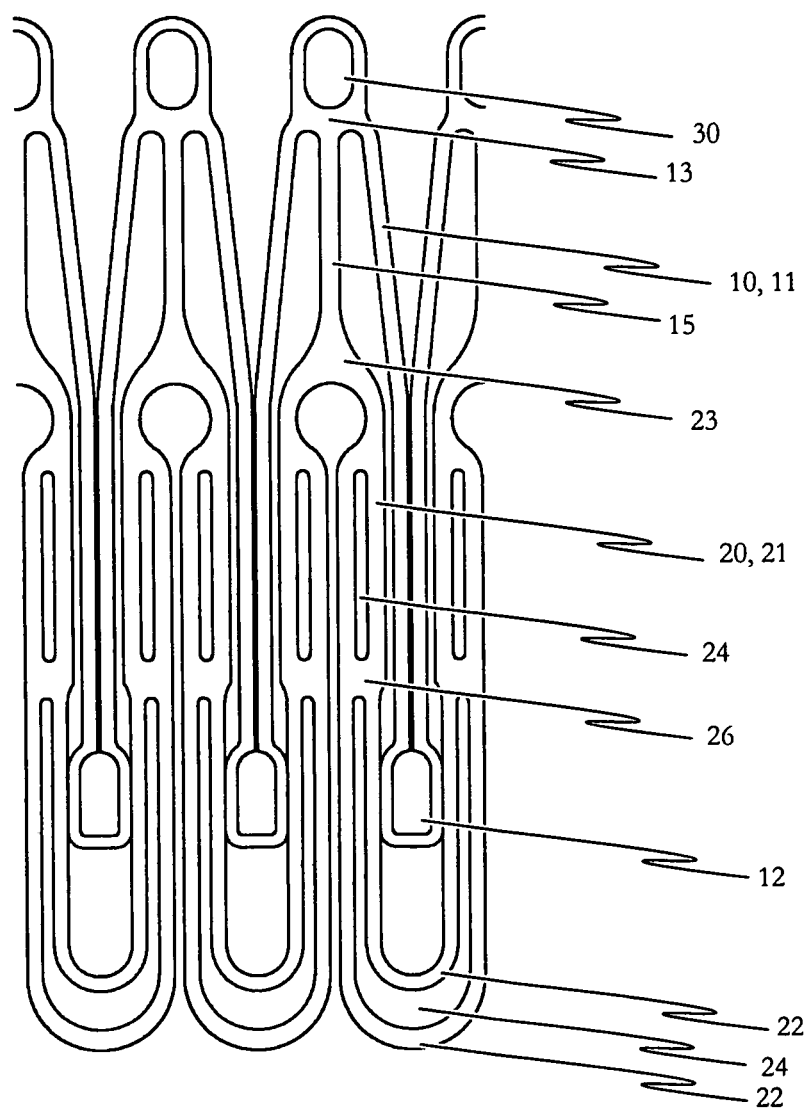
FIG. 9e is a flat projection of a cutting pattern which can be used for the production of the ninth preferred embodiment of the self-expandable endoprosthesis to cut the endoprosthesis illustrated in FIG. 9a integrally from a metal tube.

FIG. 9e illustrates a flat projection of a cutting pattern which may be used to produce the ninth embodiment of the self-expandable endoprosthesis to cut the endoprosthesis illustrated in FIG. 9a integrally from a metal tube.

Unlike the first embodiment, the respective head portions 12 of the positioning arches 10 pointing towards the proximal end 3 of the endoprosthesis are of a slightly wider design at the proximal end in the ninth embodiment of the endoprosthesis 1. Although the head portions 12 of the positioning arches 10 have a slightly rectangular in shape compared with the first embodiment, all the respective corners of the head portions 12 are rounded so that the vessel wall is not damaged when the positioning arches 10 engage in the pockets of the heart valve to be replaced. The advantage of the slightly wider design of the head portions 12 of the positioning arches 10 is that the positioning arches 10 can be placed in the pockets of the native heart valve with the smallest possible clearance during the implantation operation, thereby enabling even more accurate positioning of the medical device at the implantation site.

As with the embodiments described above, a total of two positioning webs or arms 11 extend from the head portion 12 of the positioning arches 10 to the distal end 2 of the endoprosthesis 1 for every positioning arch 10 in the ninth embodiment of the endoprosthesis 1 and which merge at the distal end 2 of the endoprosthesis 1 into an eye-shaped element 30. This eye-shaped element 30 serves as a retaining means for attaching the endoprosthesis 1 and hence the medical device to an introduction catheter system.

Specifically, in the case of the ninth embodiment of the endoprosthesis 1, the retaining eyes 30 are disposed between the two arms 11 of two mutually adjacent positioning arches 10. The connecting web 15 extends essentially in the longitudinal direction of the endoprosthesis 1 and opens into the transition portion 13 between the two arms 11 of two mutually adjacent positioning arches 10 where the retaining eye 30 is formed. At the proximal end of the connecting web 15, the latter merges into the respective retaining arms 21 of two mutually adjacent retaining arches 20. This design is illustrated particularly clearly in FIG. 9d, which shows a perspective plan view of the distal region of the endoprosthesis illustrated in FIG. 9a in its second mode.

In contrast with the embodiments described above, the respective retaining arms 21 of the retaining arches 20 on the transition portion 23 between the two arms 21 of two mutually adjacent retaining arches 20 are not provided with slots or elongate holes 24 in the ninth embodiment of the endoprosthesis 1. Due to the fact that only one arm web 21 actually opens into the transition portion 23 between the two arms 21 of two mutually adjacent retaining arches 20 for each retaining arch, there are advantageously no components belonging to the retaining arches 20 which project out from the respective retaining arches 20 in a radial direction when the endoprosthesis 1 is in the expanded state (see FIG. 9b for example). When the endoprosthesis 1 is in an expanded state, no anchoring support 25 usually extends through the slots 24 projecting out in a radial direction at the transition portions 23 between the two arms 21 of two mutually adjacent retaining arches 20. It has been found that, in this embodiment, the endoprosthesis 1 can be explanted particularly easily and removed from the patient's body.

Although the ninth embodiment of the endoprosthesis 1 does not have slots or elongate holes 24 at the respective transition portions 23 between the two arms 21 of two mutually adjacent retaining arches 20, the respective retaining arms 21 of the endoprosthesis 1 have reinforcing portions 26 which are respectively provided on portions of the retaining arms 21 that are not congruent with the transition portions 23 between the two arms 21 of two mutually adjacent retaining arches 20.

Figure 10:
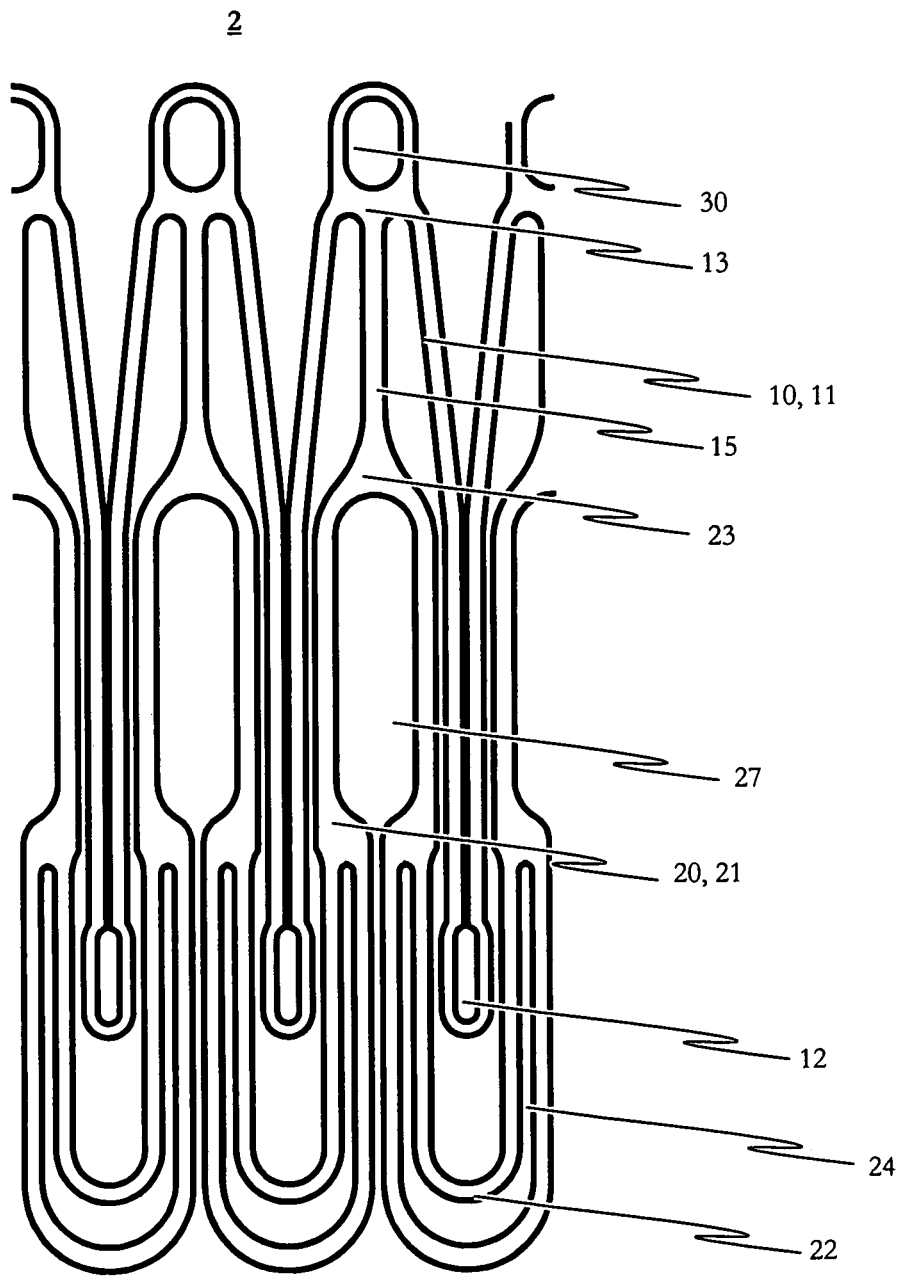
FIG. 10 is a flat projection of a cutting pattern which can be used for the production of another preferred embodiment of the self-expandable endoprosthesis to cut an endoprosthesis integrally from a metal tube.

FIG. 10 illustrates a flat projection of a cutting pattern which may be used for the production of another embodiment of the self-expandable endoprosthesis 1 to cut an endoprosthesis integrally from a metal tube. The cutting pattern illustrated in FIG. 10 differs from the cutting pattern illustrated in FIG. 1e due to the fact that the distally disposed slots 24 extending in the longitudinal direction of the retaining arches 21 have been omitted from the respective retaining arches 21 on the one hand and a bigger space 27 is cut from between the adjacent retaining arches 21 in order to save on material on the other hand.

Figure 11:
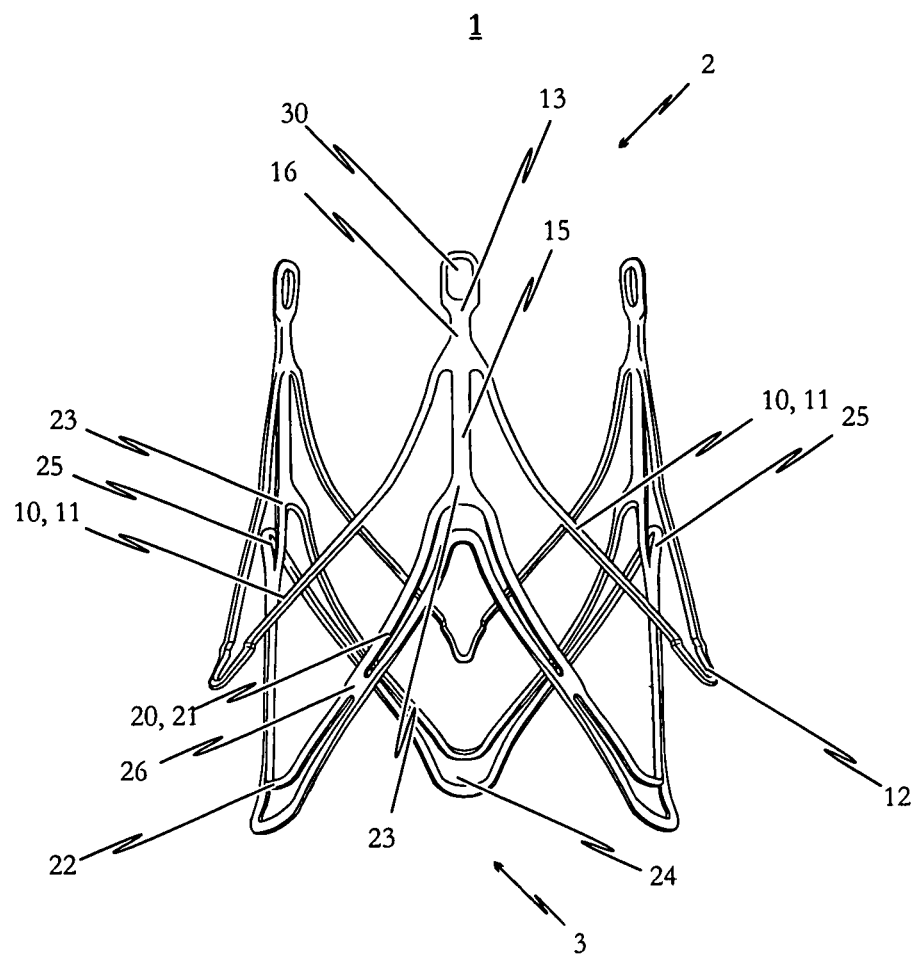
FIG. 11 shows another preferred embodiment of a self-expandable endoprosthesis for the medical device proposed by the invention in its second mode in which the medical device is in its expanded state.

FIG. 11 illustrates another embodiment of a self-expandable endoprosthesis 1 for an alternative design of the medical device proposed by the invention. Specifically, the endoprosthesis 1 of the embodiment illustrated in FIG. 11 has assumed its second mode in which the medical device is in its expanded state. The endoprosthesis 1 illustrated in FIG. 11 differs from the endoprosthesis 1 illustrated in FIG. 1c due to the fact that the stent 1 illustrated in FIG. 11 has an interconnecting web 16 extending essentially in the longitudinal direction of the endoprosthesis 1 between the retaining eyes 30 and the transition portion 13 between the positioning arms 11 of two adjacent positioning arches 10. Thus, the total length of the endoprosthesis 1, and hence the medical device, is made longer. To ensure the optimum ability to manoeuvre the medical device in the minimised state, however, it is an advantage if the endoprosthesis 1 has as short a longitudinal extension as possible, especially if the implantation route to the heart valve leads through the arch of the aorta. It is of advantage if the medical device is as short as possible (and the endoprosthesis 1 is also as short as possible) so that the medical device can be maneuvered easily around the arch.

The endoprosthesis 1 illustrated in FIG. 11 also differs from the endoprosthesis of the embodiments described above due to the fact that when the endoprosthesis 1 is in the expanded state, a barb portion 25 projects through the slots 24 in the radial direction at the respective transition portions 23 between the two arms 21 of two mutually adjacent retaining arches 20. The tip of the barb portion 25 points in the direction of the distal retaining region 2 of the endoprosthesis 1.

A yet further embodiment of the self-expandable endoprosthesis 1 for the medical device proposed by the invention will now be described with reference to FIGS. 17a to 17b.

FIG. 17a illustrates the endoprosthesis 1 (including positioning arches 54 and retaining arches 53) in its first pre-definable mode in which the medical device (not explicitly illustrated) is in a minimized state and can therefore be introduced into a patient's body with minimal invasion by means of a catheter system. The endoprosthesis 1 in its second mode includes the medical device in its expanded state. FIG. 17b illustrates the stent 50 in a state between the first mode (see FIG. 17a) and the second mode. FIG. 17b shows the catheter tip 20 rotated about its longitudinal axis L with respect to FIG. 17a to show expansion of the positioning arches 54. The endoprosthesis 1 in its expanded state includes a heart valve prosthesis 60 attached to it by sutures.

This embodiment of the self expandable prosthesis 1 corresponds essentially to the second embodiment illustrated in FIGS. 2a-2e. The difference with the embodiment illustrated in FIGS. 12a to 12e is that the retaining eyes 30 are imperforate, taking the form of retaining heads. It has been found that an imperforate retaining eye allows the medical device to be released more simply and easily from an insertion catheter system. By way of clarification, it should be noted that it is not the presence or absence of perforations in the retaining means which directly contribute to the ease of release of the retaining means from the catheter. Rather, it is the absence of parts on the catheter on which the retaining means may become lodged, passing through or penetrating the retaining means, for example, such as a peg and hole.

It will be appreciated that the various optional features, including integral or extended anchoring eyes 30, barb elements 17, reinforcing portions 26, perforate or imperforate retaining eyes 30, may be used in any combination with the endoprosthesis structure.

Figure 12A:
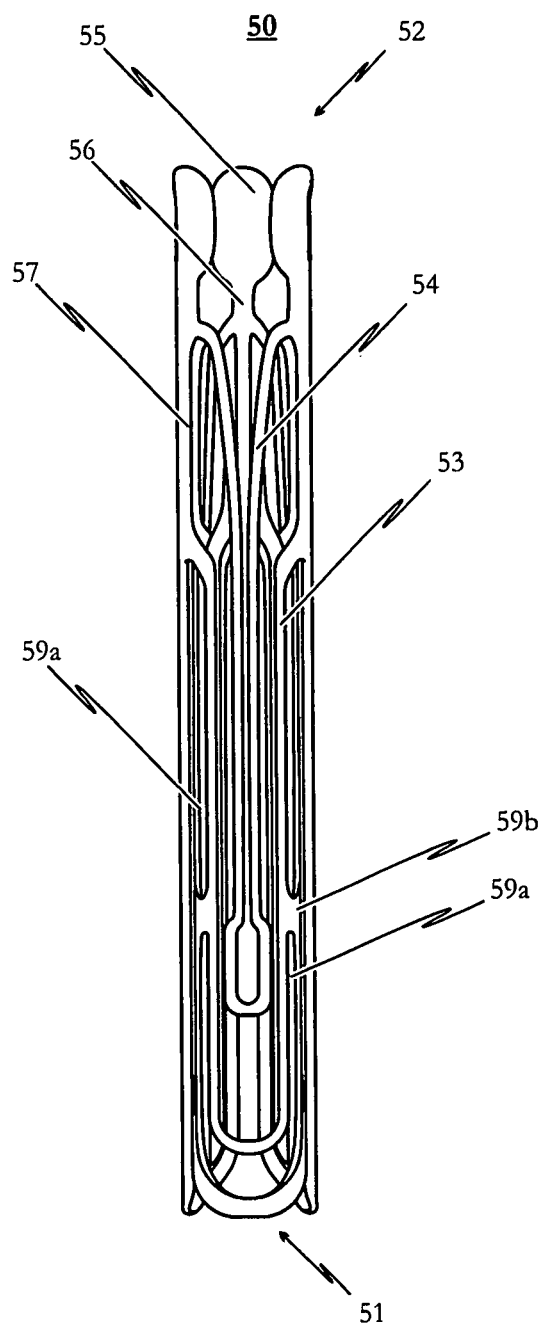
FIG. 12a shows a twelfth preferred embodiment of a self-expandable stent in its first, pre-determined mode in which the stent is in its minimised state.
Figure 12B:
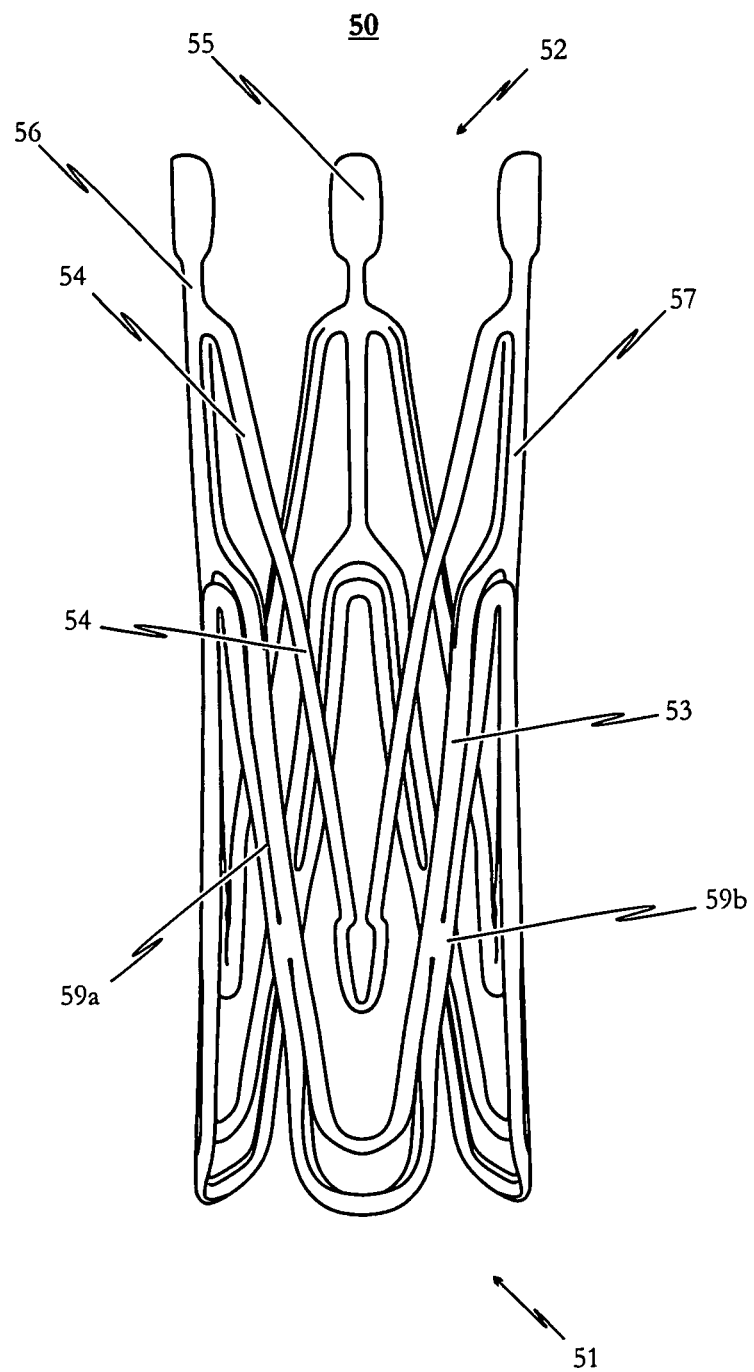
FIG. 12b shows the stent illustrated in FIG. 12a in a state between its first, pre-definable mode and its second mode in which the stent is in its expanded state.
Figure 12C:
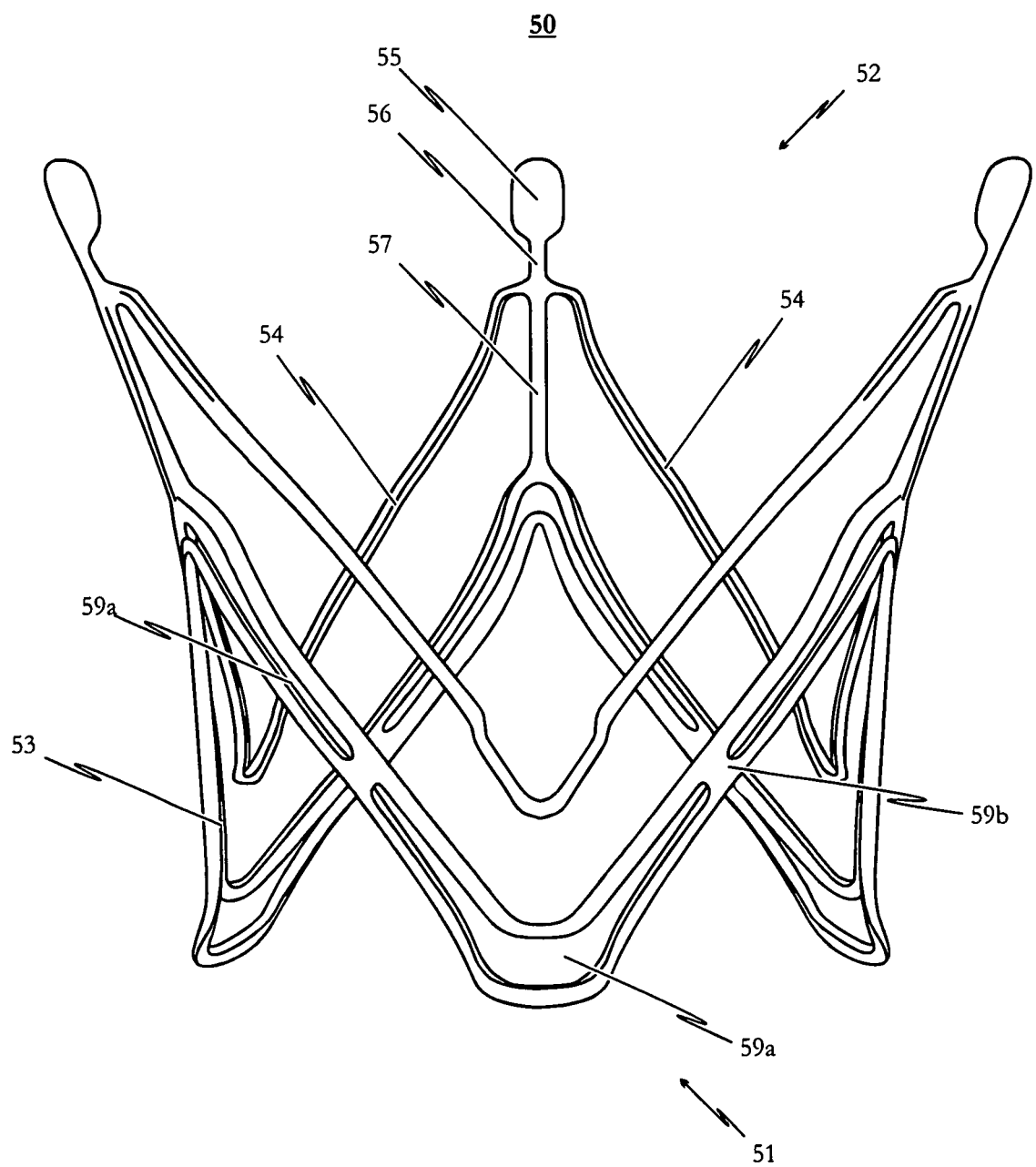
FIG. 12c shows the stent illustrated in FIG. 12a in its second mode in which the stent is in its expanded state.
Figure 12D:
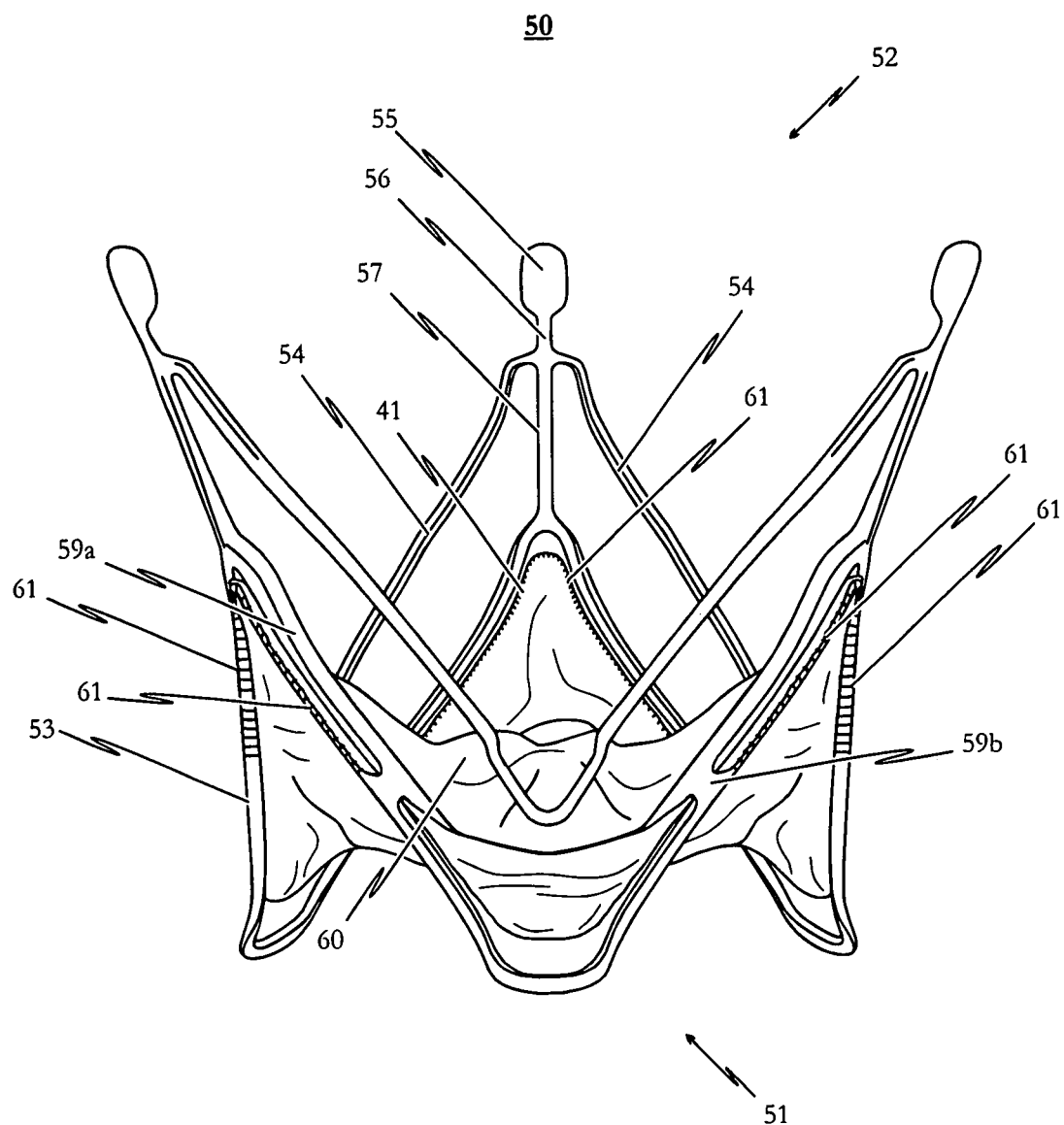
FIG. 12d shows the stent illustrated in FIG. 12c with a heart valve prosthesis attached to it and opened out.
Figure 12E:
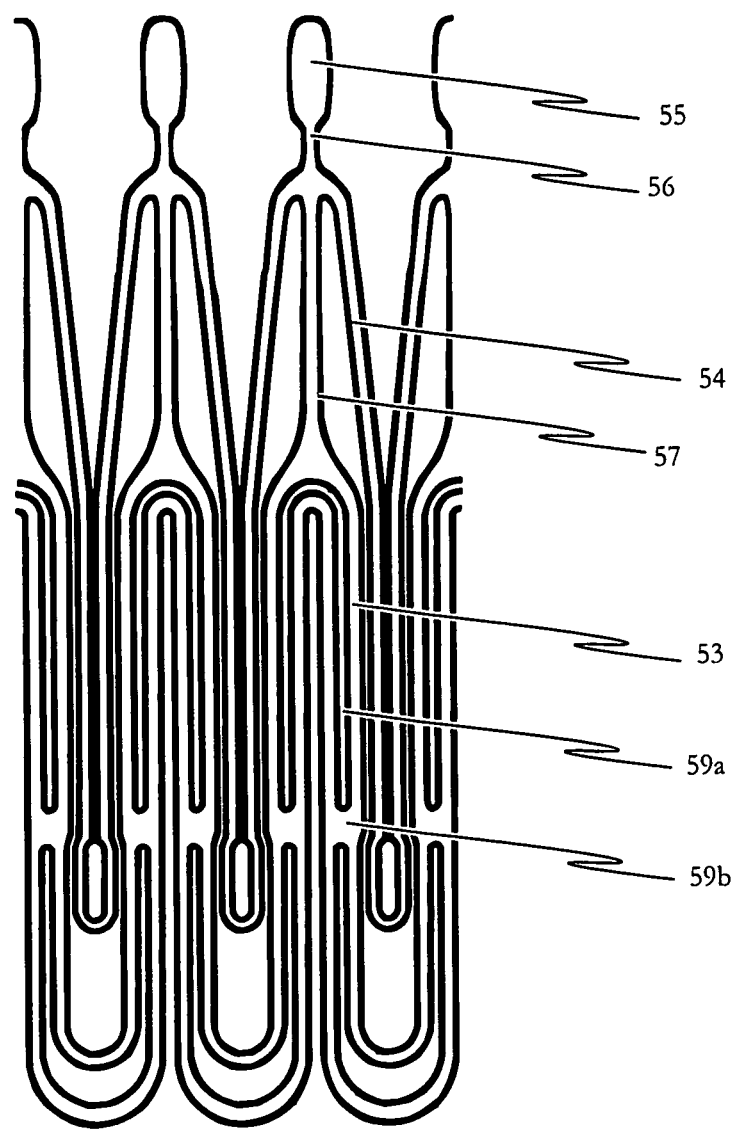
FIG. 12e is a flat projection of a cutting pattern which can be used for the production of the twelfth preferred embodiment of a self-expandable stent to cut the stent illustrated in FIG. 12a integrally from a metal tube.

A more detailed description will be given below with reference to FIGS. 12a and 12b, explaining how the medical device proposed by the invention is used to treat a condition of heart valve insufficiency.

Figure 13A:
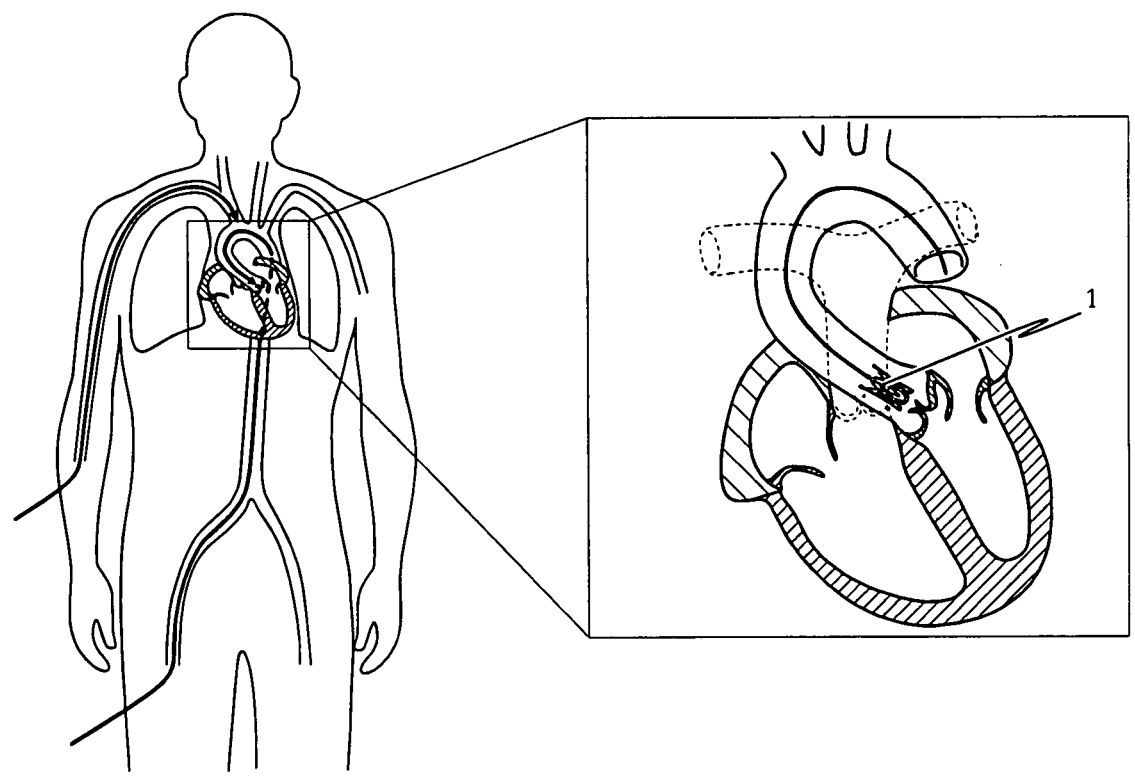
FIG. 13a is a schematic view intended to illustrate one possible implantation operation of the medical device proposed by this invention.
Figure 13B:
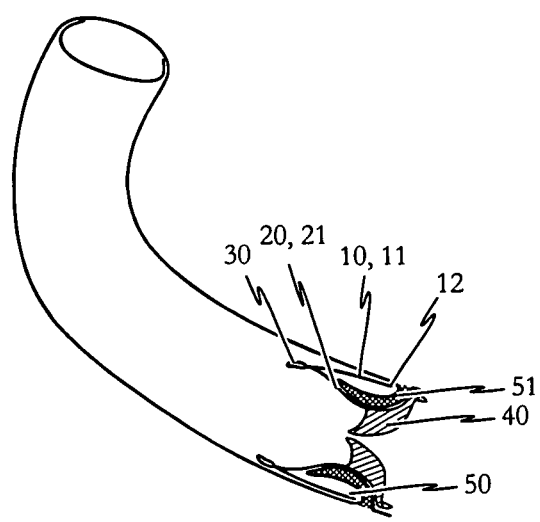
FIG. 13b is a schematic view of the medical device proposed by the invention in the implanted state.

The medical device proposed by the invention, and in particular the endoprosthesis 1 with the heart valve prosthesis 40 contained in it, is designed to be introduced into the patient's body either backwards (retrograde) or transapically, i.e. approaching from the heart apex via a special catheter. The device is positioned percutaneously orthotopically in vivo and assumes the function of an insufficient or narrowed (stenosed) heart valve. FIG. 13a provides a schematic illustration of one possible implantation operation for the medical device proposed by the invention, whereby the medical device in this instance is introduced into the patient's body via a retrograde approach from the femoral artery using a special catheter. FIG. 13b provides a schematic view of the medical device proposed by the invention in the implanted state.

In the case of the implantation route illustrated in FIG. 13a, the catheter system, which is not specifically illustrated, containing the medical device with the heart valve prosthesis 40 and the endoprosthesis 1 serving as an anchoring stent, is introduced by puncturing the A. femoris communis (inguinal artery). This catheter system is preferably moved forward to the aortic valve position assisted by angiographic (vessel display) and echocardiographic (ultrasound) control, where the actual heart valve implantation then takes place.

Alternatively, a catheter system can be pushed transapically from the heart apex through the left ventricle to the aortic valve where a similar implantation of the endoprosthesis 1 with the heart valve prosthesis 40 is possible using a catheter suitably modified accordingly.

As the catheter system is introduced, the medical device is preferably cooled, for example by rinsing the interior of the catheter system with an appropriate coolant such as a cooled salt solution. When the medical device has been moved forward to the desired implantation site, cooling is interrupted, as a result of which the endoprosthesis 1 of the medical device is warmed to the body temperature of the patient (36° C.), thereby triggering the shape memory effect of the endoprosthesis material.

Due to the triggering of the self-expanding property of the endoprosthesis 1, radial forces develop which act on the individual components of the endoprosthesis 1, in particular on the respective positioning arches 10, 11 and retaining arches 20, 21 of the endoprosthesis 1. Since the endoprosthesis 1 of the medical device is still disposed in the introduction catheter system as before, the radial forces which develop once the critical switching temperature is exceeded and act on the individual components of the endoprosthesis 1 so that—in spite of the shape memory effect having been triggered—the endoprosthesis 1 of the medical device is forcibly held in its first (minimised) shape within the closed introduction port of the introduction catheter system.

By releasing the endoprosthesis 1 from the introduction catheter system in appropriate steps, the positioning arches 10, 11 of the endoprosthesis 1 are moved out though the introduction port of the introduction catheter system once opened. The positioning arches 10, 11 open out due to the radial forces within the endoprosthesis. The opened positioning arches 10, 11 are then positioned in the pockets 50 of the native heart valve 51.

The other components of the endoprosthesis 1 and the medical device are then released through the introduction port of the introduction catheter system. As illustrated in FIG. 13b, the retaining arches 20, 21 open together in the radial direction and cause the heart valve prosthesis 40 attached to the retaining arches 20, 21 to open out in the manner of an umbrella. However, the radial forces acting on the retaining arches 20, 21 also act on the distal anchoring region 2 of the endoprosthesis 1, causing the endoprosthesis 1 to be pressed in a radial direction against the vessel wall. This, on the one hand, guarantees a reliable anchoring of the medical device at the implantation site and, on the other hand, ensures a reliable seal of the heart valve prosthesis 40 at the proximal anchoring region 3 of the endoprosthesis 1.

When the medical device is in the implanted state as illustrated in FIG. 13b, the heart valve prosthesis 40 is opened out at the proximal anchoring region 3 of the endoprosthesis 1 whilst the old (insufficient) heart valve 51 is pressed towards the vessel wall due to the self-expanding property of the endoprosthesis 1. The distal anchoring region 2 of the endoprosthesis 1 affords additional mechanical support for the system and reliable anchoring.

As may be seen from FIG. 13b, when the endoprosthesis 1 is in its expanded state, the respective positioning arms 21 of the positioning arches 20 locate in the pockets of the incumbent heart valve and thus essentially guarantee secure and error-free positioning of the medical device. The pocket flaps of the incumbent heart valve are clamped between the positioning arches 10 and the retaining arches 20 due to the expansion of the endoprosthesis 1. This further assists in achieving optimum positioning and a stable anchoring of the heart valve prosthesis 40. Optimum lateral sealing of the implanted valve prosthesis 40 is guaranteed at the same time.

The system is afforded additional mechanical support and reliable anchoring by providing barbs 17 on the retaining eyes 30 disposed at the distal anchoring region 2 of the endoprosthesis 1 and/or by appropriate anchoring supports 25. When the endoprosthesis 1 is in the expanded state, the anchoring supports 25 stand proud of the co-operating arm 21 of the retaining arches 20 and their tips point in the direction of the distal end 2 of the endoprosthesis 1.

The design of the endoprosthesis 1 allows gripping of the endoprosthesis 1 by means of the retaining eyes 30 and minimising the medical device by the longitudinal extension of the endoprosthesis 1 so that the medical device is pulled back into the catheter and removed from the patient's body.

Due to the modular integration of retaining elements (retaining eyes) on the self-expandable endoprosthesis 1, it can also be explanted again by way of a catheter once the endoprosthesis has been implanted. To this end, the distal anchoring region 2 of the endoprosthesis 1 is pulled into a catheter by the several retaining eyes using guide wires within the catheter. In other words, in the reverse of the implantation operation, the endoprosthesis 1 is pulled from its expanded state back into its minimised state and released from the anchoring in the pockets of the incumbent heart valve. As will be described below the design of the endoprosthesis allows reversal of the implantation at any stage during the implantation process. Specifically explantation may be carried out causing minimal damage and/or stress to the heart, the vasculature and the patient.

Further preferred aspects of the invention will now be described with reference to a catheter insertion system.

Reference to the use of the catheter insertion system specifically disclosed herein is not intended to necessarily limit the use of the stent with this catheter insertion system alone. It is the novel features of the catheter tip, which could be supplied in the form of a modular cartridge for example, in combination with the retaining means, which afford the increased reliability in terms of stent release and positioning. Thus such a catheter tip, or cartridge, could be affixed to catheter systems already known in the art.

With reference to FIGS. 14 and 15, use of the stent with a catheter insertion system of a transapical design will be explained for transapical insertion of a self-expandable heart valve stent to a patient's body. FIGS. 14a to d and FIGS. 15a to d respectively illustrate an insertion system in its four different pre-definable functional modes.

The insertion system 1 is suitable for transapical access to a heart valve to be replaced, such as an aortal valve for example. Using the insertion system 1, it is possible to implant a self-expandable heart valve stent in a patient's body transapically, i.e. from the heart apex. To this end, the insertion system 1 has a catheter system 10, by means of which the heart valve stent, not explicitly illustrated in FIGS. 14 and 15, can be inserted in the patient's body in its minimised mode. FIG. 16 illustrates an embodiment of the catheter tip proposed by the invention.

In the insertion system 1 illustrated in FIGS. 14 and 15, a catheter tip 20 is provided at the proximal end 11 of the catheter system 10, in which the heart valve stent to be implanted in the patient's body can be accommodated. At the distal end 12 of the catheter system 10, a handle 30 is also provided, by means of which the catheter tip 20 can be manipulated.

Specifically, the catheter tip 20 of the insertion system 1 illustrated in FIGS. 14 and 15 has a retaining mechanism 21 so that at least the distal region of the stent to be implanted in the patient's body can be releasably attached to the catheter tip. The retaining mechanism will be described in more detail, in particular, with reference to FIG. 16.

The catheter tip 20 also has a housing system for accommodating at least the proximal region of the stent. Specifically, the housing system comprises a first housing portion 23 for accommodating first functional components of the stent, for example for accommodating the retaining arches of the stent, and a second housing portion 24 for accommodating second functional components of the stent, for example for accommodating positioning arches of the stent.

As regards the handle 30 of the insertion system 1, it has a first operating means 33 co-operating with the first housing portion 23 and an operating means 34 co-operating with the second housing portion. The first operating means 33 of the handle 30 co-operates with the first housing portion 23 of the catheter tip 20 so that when the first operating means 33 is operated, it causes a pre-definable longitudinal movement of the first housing portion 23 relative to the fixing mechanism 21. Secondly, the second operating means 34 of the handle 30 co-operates with the second housing portion 24 of the catheter tip 20 so that when the second operating means 34 is operated, it causes a pre-definable longitudinal movement of the second housing portion 24 of the catheter tip relative to the fixing mechanism 21.

With the insertion system 1, shown in FIGS. 14 to 16 for example, the second housing portion 24 of the catheter tip 20 is disposed at the proximal end portion of the catheter tip 20. The first housing portion 23 is disposed between the housing portion 24 and the handle 30. With this transapical insertion system 1, when the associated second operating means 34 of the handle is operated, the second housing portion 24 of the catheter tip 20 can be moved in longitudinal direction L of the catheter tip 20 relative to the fixing mechanism 21 in the proximal direction, i.e. away from the handle 30. When the associated first operating means 33 of the handle 30 is operated, the first housing portion 23 can be moved in the longitudinal direction L of the catheter tip 20 relative to the fixing mechanism in the distal direction, i.e. towards the handle 30.

The insertion system 1 illustrated in FIGS. 14 to 15 also has a gate system 13 co-operating with the catheter system 10 which is connected on the one hand to the portion of the catheter tip 20 facing the handle and on the other hand to the portion of the handle 30 facing the catheter tip. The gate system 13, which is preferably of a hollow design, has in its interior a first mechanism 26, such as a wire system, to enable a force to be transmitted from the first operating means 33 of the handle 30 to the first housing portion 23 of the catheter tip 20.

The gate system 13 is also provided with a second mechanism 27 for transmitting force from the second operating means 34 of the handle 30 to the second housing portion 24 of the catheter tip 20. As with the first force transmitting mechanism 26, the second force transmitting mechanism 27 may be provided in the form of a wire system.

In detail, in the insertion system 1, the second force transmitting mechanism 27, actively connecting the second operating means 34 of the handle 30 with the second housing portion 24 of the catheter tip 20, is provided in the form of a wire extending through the interior of the gate system 13. The wire is connected to the second operating means 34 of the handle 30 on the one hand and to the second housing portion 24 of the catheter tip 20 on the other hand. The first force transmitting mechanism 26 is provided in the form of a sleeve which extends through the interior of the gate system 13 and surrounds the wire constituting the second force transmitting mechanism 27. The first force transmitting mechanism 26 constitutes an extension of the first housing portion 23 of the catheter tip 20 and is actively connected to the first operating means 33 of the handle on the one hand and to the first housing portion 23 of the catheter tip 20 on the other hand. Naturally, however, it would also be conceivable for the first force transmitting mechanism 26 to be provided in the form of a sleeve surrounding the wire constituting the second force transmitting mechanism 27. In which case the sleeve of the first force transmitting mechanism 26 simultaneously also constitutes the gate system 13 and is an extension of the first housing portion 23 which is actively connected to the first operating means 33 of the handle on the one hand and to the first housing portion 23 of the catheter tip 20 on the other hand.

The gate system 13 or the sleeve of the first force transmitting mechanism 26 used with the catheter system 10 of the transapical design of the insertion system 1 is provided in the form of an elongate tube and the second force transmitting mechanism 27. Optionally, the first force transmitting mechanism 26 is disposed in the interior of this tube. The gate system 13 is preferably designed so that its length remains virtually unchanged, especially when subjected to the compression or tensile stress which occurs during the process of inserting the catheter system 10. This function of the gate system 13 is achieved by using an appropriate material for the elongate tube and by an expedient choice of the wall thickness. In particular, it is preferable if the gate system 13 or the sleeve of the first force transmitting mechanism 26 is both resistant to buckling and also flexible so that a bending radius of at least 4 cm and preferably at least 3 cm can be achieved with the gate system 13, at least in the proximal region 14 of the gate system 13.

As regards the fixing mechanism 21 belonging to the catheter tip 20 in the illustrated embodiment of the transapically designed insertion system 1, this fixing mechanism 21 is provided in the form of a crown 21a with a total of three pockets 22 formed therein. The pockets 22 of the crown 21a are of a design complementing retaining elements, for example retaining heads, which are disposed at a distal region of the stent which is to be accommodated or can be accommodated in the catheter tip 20 of the insertion system 1. The pockets 22 formed in the crown 21a establish a releasable engagement with the distal region of the stent so that the stent can be releasably attached to the retaining mechanism 21 of the catheter tip 20.

As may be seen in particular from FIGS. 14 and 15, in the embodiment of the illustrated transapically designed insertion system 1, both the first housing portion 23 of the catheter tip 20 and the second housing portion 24 of the catheter tip 20 are each provided in the form of sleeves or sleeve-type portions and are specifically designed to accommodate the functional components of the stent. Specifically, the internal diameter of the second sleeve-type housing portion 24 is bigger than the external diameter of the first sleeve-type housing portion 23. Accordingly, in the case of the embodiment of the illustrated transapically designed insertion system 1, the second housing portion 24 of the catheter tip 20 is designed to accommodate, in addition to the second functional components of the stent, namely the positioning arches of the stent, the first housing portion 23 of the catheter tip 20 with the first functional components of the stent accommodated in it, namely the retaining arches of the stent.

Turning to the handle 30 used with the embodiment of the insertion system 1 illustrated in FIGS. 14 and 15, the illustrated embodiment of the insertion system 1 is such that the second operating means 34, which co-operates with the second housing portion 24 of the catheter tip 20 via the second force transmitting mechanism 27, has a carriage which is guided in a guide 31' and actively connected to a slide 31". The carriage of the second operating means 34 is actively connected to the second housing portion 24 of the catheter tip 20 co-operating with the second operating means 34 via the second force transmitting mechanism 27 so that when the second operating means 34 is operated, in particular the carriage of the second operating means 34, a force is transmitted directly from the carriage of the second operating means 34 to the second housing portion 24 of the catheter tip 20. In the same way, the first operating means 33, which is actively connected to the first housing portion 23 of the catheter tip 20 via the first force transmitting mechanism 26, also has a carriage which is guided in a guide 32' and is actively connected to another slide 32". The carriage of the first operating means 33 is actively connected to the first housing portion 23 of the catheter tip 20 co-operating with the first operating means 33 via the first force transmitting mechanism 26. Thus, when the first operating means 33 is operated, in particular when the carriage of the first operating means 33 is operated, a force is transmitted directly from the carriage of the first operating means 33 to the first housing portion 23 of the catheter tip 20.

As regards the first operating means 33 of the handle 30 used with the insertion system 1 illustrated in FIGS. 14 and 15, the handle 30 also has a first and a second stop 35, 36. These stops co-operate with the first operating means 33 and are designed to fix the total stroke length of the longitudinal movement of the first housing portion 23 of the catheter tip 20 when the operating means 33 is operated. This is achieved by the fact that the displacement path which can be covered by the slide of the first operating means 33 on the guide 32' is fixed.

The handle 30 also has a third and fourth stop 37, 38 which co-operate with the second operating means 34 and fix the total stroke length of the longitudinal movement. This can be effected by the second housing portion 24 of the catheter tip 20 when the second operating means 34 is operated.

In addition to the third and fourth stops 37, 38, the handle 30 of the embodiment of the insertion system 1 illustrated in FIGS. 14 and 15 also has another, fifth stop 39 co-operating with the second operating means 34. This stop co-operates with the third stop 37 on the one hand and with the fourth stop 38 on the other hand. When the second operating means 34 is operated, a stepped longitudinal movement comprising two individual steps of the carriage on the guide 31' of the second operating means 34 is effected and thus a stepped longitudinal movement occurs comprising two individual steps of moving the second housing portion 24 of the catheter tip 20 relative to the fixing mechanism or crown 21 of the catheter tip 20.

Since the fifth stop 39 co-operating with the second operating means 34 is expediently positioned on the guide 31' of the second operating means 34 between the third stop 37 and the fourth stop 38. The third and fifth stops 37, 39 on the one hand and the fourth and fifth stops 38, 39 on the other hand fix the stroke length of the longitudinal movement of the second housing portion 24 of the catheter tip 20 for each individual step when the second operating means is operated.

As illustrated in FIGS. 14 and 15, in the illustrated embodiment of the insertion system 1, the above-mentioned fifth stop 39 of the handle 30 co-operating with the second operating means 34 of the handle 30 is provided in the form of a stop element 44 releasably secured to the guide 31' of the carriage belonging to the second operating means 34.

Finally, the handle 30 of the insertion system 1 illustrated in FIGS. 14 and 15 is such that both the first operating means 33 and the second operating means 34 are each assigned a locking element 41, 42. Specifically, the first locking element 41, co-operating with the first operating means 33 of the handle 30, is provided in the form of a locking element which can be removed from the carriage or from the slide 32" of the first operating means 33. The locking element 41 co-operates with the first operating means 33 and with the carriage of the first operating means 33 so that a longitudinal movement of the first housing portion 23 of the catheter tip 20, which can be effected by means of the first operating means 33, can be blocked. The second locking element 42 on the other hand, which co-operates with the second operating means 34, is also provided in the form of a locking element which can be removed from the carriage or from the slide 31" of the second operating means 34. The locking element co-operates with the second operating means 34 so that a longitudinal movement of the second housing portion 24 of the catheter tip 20, which can be effected by means of the second operating means 34, can be blocked.

The four different functional modes which can be achieved with the insertion system 1 will be described below with reference to FIGS. 15a to 15d.

Figure 15A:
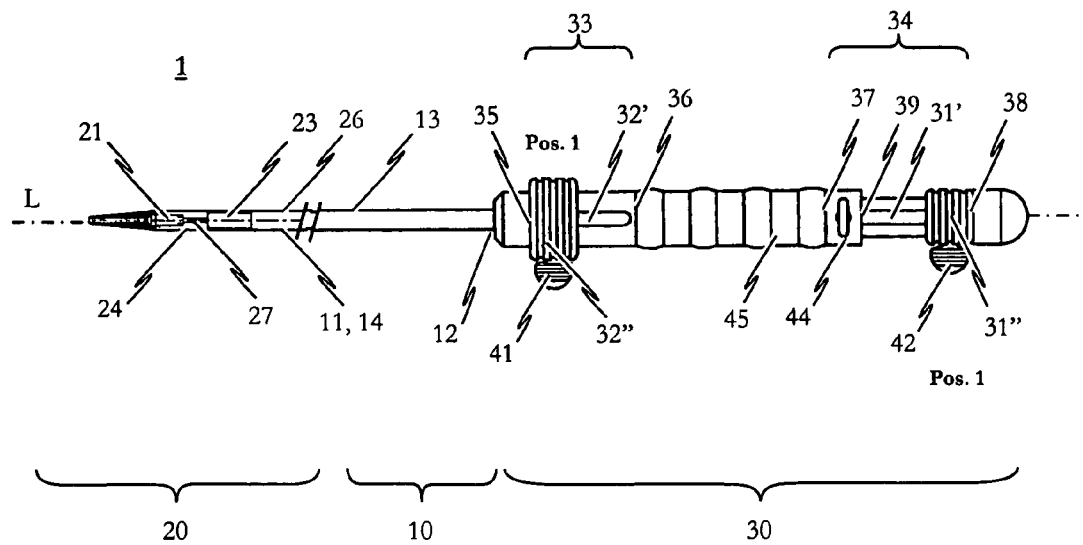
FIGS. 15a to d shows the embodiment of insertion system illustrated in FIG. 14 in its four pre-definable functional modes with a view to illustrating the procedure whereby a stent accommodated in the insertion system is released.

FIG. 15a illustrates the insertion system 1 in its first functional mode, in which the catheter tip 20 is completely closed. As mentioned above, a self-expandable heart valve stent can be accommodated in the catheter tip 20 or in the corresponding housing portions 23 and 24 of the catheter tip 20.

In the first functional mode illustrated in FIG. 15a, the respective slides 31" and 32" and hence the respective carriages 31 of the second and first operating means 34 and 33 are each in their first position (pos. 1). Specifically, the slide 32" of the first operating means 33 lies against the first top 35 provided at the catheter tip end of the guide 32'. In this first position, the slide 32" is fixed by means of the first locking element 41 so that a longitudinal movement of the slide 32" and the carriage of the first operating means 33 on the guide 32' is blocked in the direction of the second stop 36 co-operating with the first operating means 33.

The slide 31" and the carriage of the second operating means 34 are also lying in the first functional mode illustrated in FIG. 15a, likewise in the first position (pos. 1) on the third stop 37 of the second operating means 34. The third stop of the second operating means 34 is disposed at the distal end of the guide 31' of the second operating means 34. In this first position, the slide 31" and the carriage of the second operating means 34 are fixed by means of the second locking element 42 in order to block a longitudinal movement of the slide 31" and carriage along the guide 31' in the direction towards the catheter tip.

As mentioned above, when the insertion system 1 is in the first functional mode as illustrated in FIG. 15a, the catheter tip 20 of the insertion system 1 is in a completely closed mode. In this mode, the first and second housing portions 23 and 24 of the catheter tip 20, provided in the form of sleeve-shaped elements, engage telescopically one inside the other. This feature is achieved by adapting the respective internal and external diameters of these sleeve-shaped elements to one another accordingly. Specifically, the sleeve-type second operating means 34 has an external diameter which is preferably identical to the external diameter of the proximal region 14 of the gate system 13. As will be described in more detail below, the sleeve-type first and second housing portions 23 and 24 of the catheter tip 20 are adapted to one another in terms of their respective internal and external diameters so that the folded retaining arches of the stent to be accommodated in the catheter tip 20 with the heart valve prosthesis attached to it can be accommodated in the sleeve-shaped first housing portion 23 and can be held in their folded or minimised mode. At the same time, the folded positioning arches of the stent are accommodated between the sleeve-shaped first housing portion 23 and the sleeve-shaped second housing portion 24 of the catheter tip 20 and held in their folded mode.

In the first functional mode of the insertion system 1, the catheter tip 20 is inserted in the patient's body and guided to the desired implantation site. In the case of the insertion system 1 based on the first embodiment of the solution proposed by the invention, illustrated in FIG. 15a, the implantation site, i.e. the incumbent heart valve, can be accessed transapically, in other words from the heart apex, because at the proximal region of the catheter tip 20 the retaining mechanism is provided in the form of the crown 21, whilst the first housing portion 23 of the catheter tip 20 is disposed distally with respect to it.

Figure 15B:
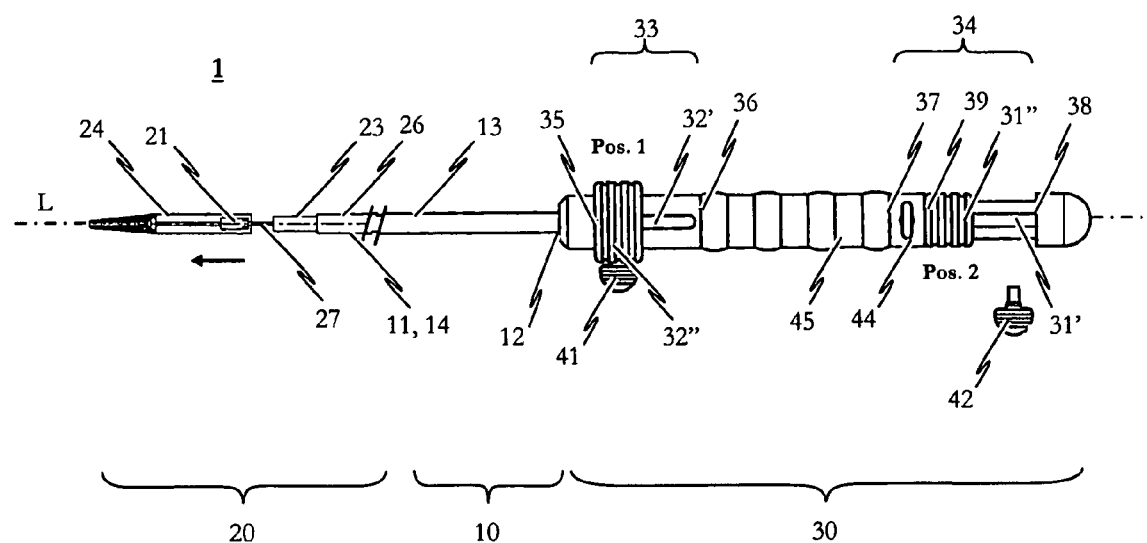

FIG. 15b shows the insertion system 1 illustrated in FIG. 15a in its second functional mode. This second functional mode is assumed immediately the catheter tip 20 of the insertion system 1 has reached the implantation site in the patient's body. As will be explained in more detail with reference to FIGS. 15b to 15d, once the catheter tip 20 has reached the implantation site, the requisite manipulations of the individual housing portions 23, 24 of the catheter tip which are needed to release the stent accommodated in the catheter tip 20 in a predefined sequence of events in steps are effected so that the different functional components of the stent, in particular the positioning arches and the retaining arches of the stent, are released in sequence. Stepped release of the endoprosthesis accommodated in the catheter tip 20 of the insertion system 1 by specific movements of the individual housing portions 23 and 24 of the catheter tip 20 will be explained in detail below.

Once the catheter tip 20 has reached the implantation site, the insertion system 1 is switched from the first functional mode illustrated in FIG. 15a to the second functional mode illustrated in FIG. 15b by operating the second operating means 34. Specifically, the second locking element 42 is removed from the second operating means 34, as a result of which the longitudinal movement of the slide 31" and the carriage of the second operating means 34 is no longer blocked.

After removing the second locking element 42 from the second operating means 34 and after releasing the lock of the slide 31" and the carriage of the second operating means 34, the slide 31" and carriage of the second operating means 34 are moved along the guide 31' in the direction of the catheter tip 20 from the first position (pos. 1) to the second position (pos. 2). The second position (pos. 2) is determined by the fifth stop 39 disposed between the third stop 37 (pos. 1) and the fourth stop 38.

By operating the second operating means 34 in this way, the second housing portion 24 of the catheter tip 20 co-operating with the second operating means 34 is moved in the proximal direction relative to the retaining mechanism 21 of the catheter tip 20. The amount of movement, i.e. The extent of the longitudinal movement of the second housing portion 24 of the catheter tip 20 relative to the fixing mechanism 21 of the catheter tip 20 in the proximal direction in this instance, is fixed by the stroke length of the longitudinal movement which can be effected between the first position (pos. 1) and the second position (pos. 2) effected by the slide 31" and the carriage using the second operating means 34.

The resultant movement of the second housing portion 24 of the catheter tip 20 relative to the fixing mechanism 21 causes release of the telescopic engagement between the two sleeve-shaped first and second housing portions 23 and 24. The extent of the movement of the second housing portion 24 relative to the fixing mechanism 21 or relative to the first housing portion 23, and hence the stroke of the longitudinal movement which can be effected by the slide 31" and carriage using the second operating means 34, is selected so that the sleeve-shaped second housing portion 24 of the catheter tip 20 no longer surrounds the first housing portion 23 of the catheter tip 20 telescopically but still covers the retaining mechanism 21 or crown 21a, in particular the pockets 22 formed in the crown 21a, As a result, in the second functional mode of the insertion system 1, as illustrated in FIG. 17b, the distal retaining region of the heart valve stent accommodated in the catheter tip 20 is held fixed by the catheter tip 20, in particular by the retaining mechanism 21. This is achieved because the retaining heads, etc., provided at the distal end of the stent are engaged with the pockets 22 formed in the crown 21a of the retaining mechanism 21.

As will be explained in more detail below with reference to FIG. 17, when the insertion system 1 is in the second functional mode illustrated in FIG. 15b, the retaining arches of the stent are still held in their minimised mode by the first housing portion 23 of the catheter tip 20. This is because these components of the stent are accommodated in the first housing portion 23 of the catheter tip 20. Engagement between the retaining heads at the distal end of the stent and the pockets 22 formed in the crown 21a of the retaining mechanism 21 is secured by means of the distal end of the second housing portion 24 so that the distal retaining region of the stent is also still held in its minimised mode by the second housing portion 24. As already explained, this is made possible because the distal end of the second housing portion 24 is still covering the crown 21a and the retaining mechanism 21 with the pockets 22 formed therein and the retaining heads of the stent accommodated in the pockets 22.

By manipulating the second operating means 34, the second housing portion 24 of the catheter tip 20 is moved away from the handle 30 in the proximal direction relative to the retaining mechanism 21 and to the first housing portion 23 of the catheter tip 20 so that the positioning arches of the stent are no longer covered by the second housing portion 24. In other words, due to the longitudinal movement of the second housing portion 24, when the insertion system 1 is in the second functional mode, the telescopic hold of the positioning arches of the stent between the first and the second housing portions 23 and 24 of the catheter tip 20 achieved in the first functional mode (see. FIG. 15a) is released. When the insertion system 1 is in the second functional mode (see. FIG. 15b), the second housing portion 24 of the catheter tip 20 no longer assumes the function of holding the positioning arches of the stent in their minimised mode so they are released and are able to unfold accordingly. As illustrated in detail in FIG. 17, the positioning arches of the stent open up once they have been released because of the inherent radial forces in the stent structure. These opened positioning arches can then be positioned in the pockets of the incumbent heart valve.

Figure 15C:
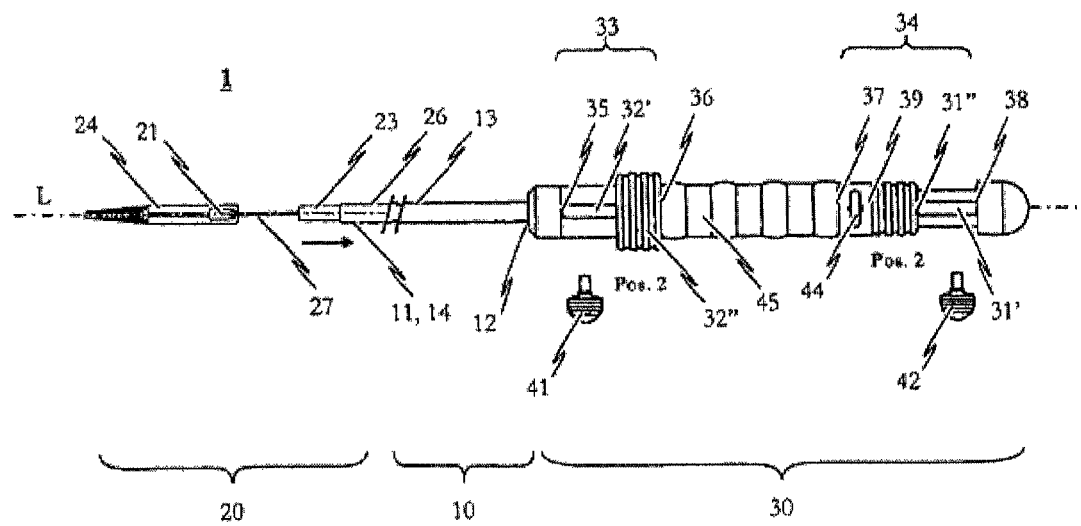
Figure 15D:
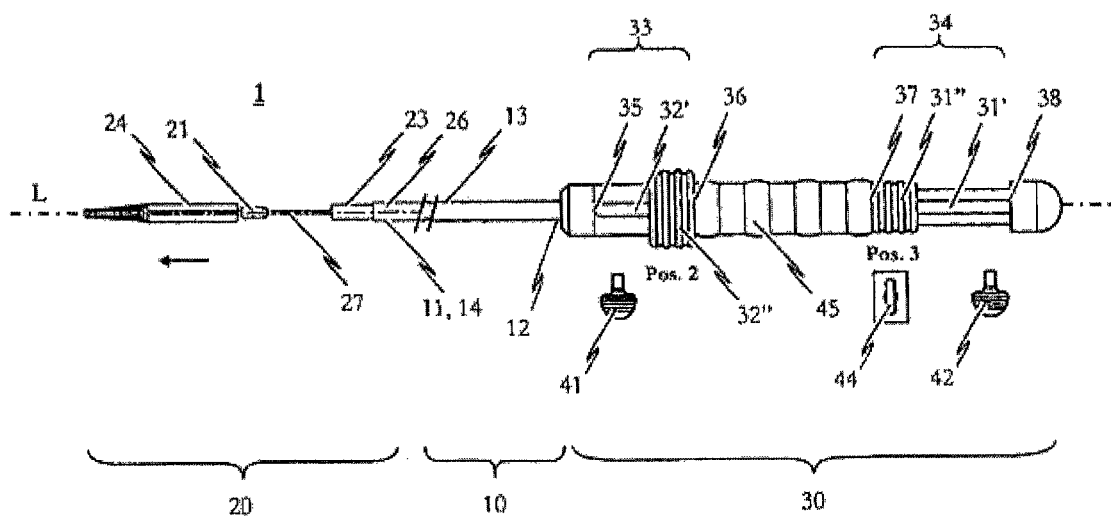

Once the positioning arches of the stent have been positioned in the pockets of the incumbent heart valve, the insertion system 1 is transferred from the second functional mode illustrated in FIG. 15b to the third functional mode illustrated in FIG. 15c. This is achieved by removing the first locking element 41 co-operating with the first operating means 33 of the handle 30 and thus releasing the lock, allowing the slide 32" and the carriage of the first operating means 33 to effect a longitudinal movement.

Once the first locking element 41 has been removed, the slide 32" and carriage of the first operating means 33 are moved along the guide 32' from the first position (pos. 1) into the second position (pos. 2). The stroke of the longitudinal movement is fixed by the second stop 36 of the first operating means 33 disposed at the distal end of the guide 32' of the first operating means 33.

By manipulating the first operating means 33, the first housing portion 23 of the catheter tip 20 co-operating with the first operating means 33 is moved by the stroke of the longitudinal movement. This is effected by the slide 32" and carriage of the first operating means 33 relative to the retaining mechanism 21 of the catheter tip 20 and to the second housing portion 24 in the distal direction towards the handle 30. With this movement of the first housing portion 23 of the catheter tip 20 relative to the retaining mechanism and crown 21a, the first housing portion 23 is no longer covering the proximal anchoring region of the stent and therefore releases the retaining arches of the stent, together with the heart valve prosthesis attached to it. This is due to an expedient selection of the stroke of the longitudinal movement which can be achieved by the first operating means 33. The release of the proximal anchoring region of the stent causes the proximal anchoring region of the stent to unfold completely by virtue of the radial forces acting on it.

When the insertion system 1 is in the third functional mode, as illustrated in FIG. 15c, the distal end of the second housing portion 24 of the catheter tip 20 is still covering the retaining mechanism 21 or the crown 21a. The engagement of the stent retaining heads in pockets 22 formed in the crown 21a continues to exist so that the stent remains actively connected to the catheter system 10 of the insertion system 1. In spite of the fact that its proximal anchoring region has unfolded, the stent with the heart valve prosthesis attached to it can still be retracted back into the catheter and explanted. Explantation takes place in a corresponding sequence but in reverse, whereby the insertion system 1 is firstly switched from the third functional mode to the second functional mode and then to the first functional mode.

Once the proximal anchoring region of the stent has been fully released and after checking that the unfolded heart valve prosthesis is functioning correctly, the stent can be released from the catheter tip. This is achieved by switching the insertion system 1 from its third functional mode illustrated in FIG. 15c to the fourth functional mode illustrated in FIG. 15d. If any abnormalities are found during the check the stent may be explanted as described above.

Figure 14A:
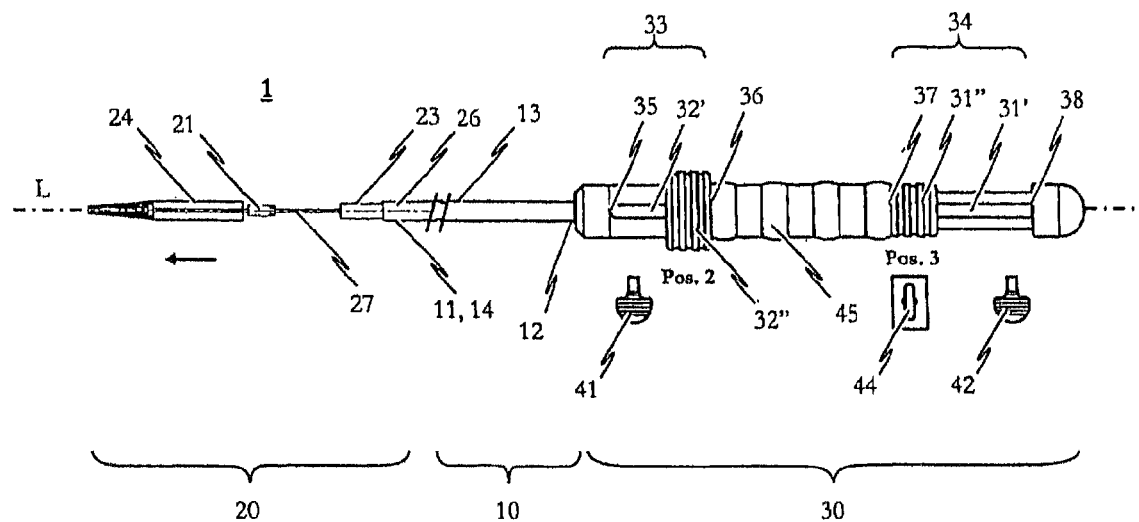
FIGS. 14a to d illustrate a preferred embodiment of the insertion system of a transapical design proposed by the invention as a means of inserting a self-expandable heart valve stent in its four pre-definable functional modes with a view to illustrating the procedure of loading a stent in the insertion system.
Figure 14B:
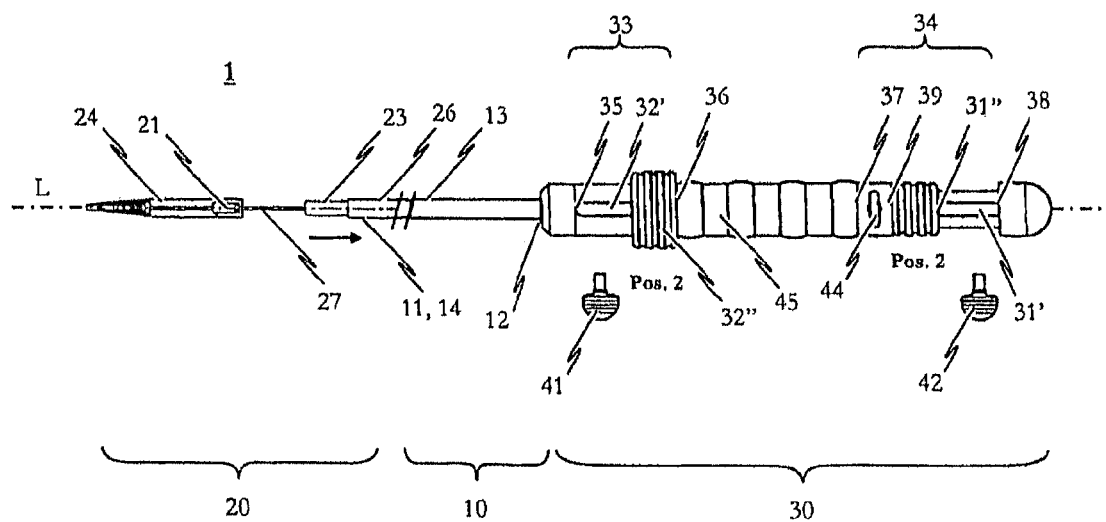
Figure 14C:
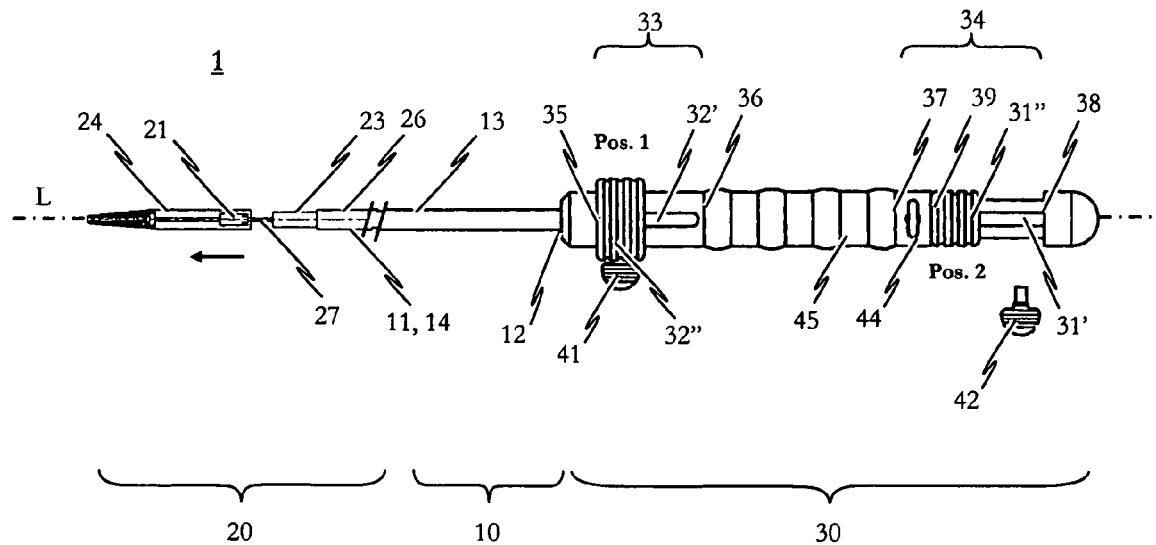

In the fourth functional mode, the catch element or locking element 44 provided between the third stop 37 and fourth stop 38 on the guide 31' of the second operating means 34, which defines the fifth stop 39 in the second functional mode illustrated in FIG. 14b, has been removed. As a result, the slide 31" and carriage of the second operating means 34 can be moved farther in the direction of the catheter tip 20 of the insertion system 1 on the guide 31', from the second position (pos. 2) into the third position (pos. 3). This third position (pos. 3) is defined by the fourth stop 38 at the proximal end of the guide 31' of the second operating means 34. Accordingly, a predefined (additional) movement of the carriage of the second operating means 34 is effected. As a result, the second housing portion 24 of the catheter tip 20 co-operating with the second operating means 34 is moved relative to the retaining mechanism 21 further in the proximal direction, away from the handle 30, due to the stroke of the longitudinal movement caused by the additional manipulation of the second operating means 34.

The stroke of the longitudinal movement caused by the additional manipulation of the second operating means 34 is selected so that when the second housing portion 24 of the catheter tip 20 is moved relative to the retaining mechanism 21, at least the pockets 22 formed in the crown 21a of the retaining mechanism 21 are no longer covered by the distal end of the second housing portion 24. This uncovering of the pockets 22 of the retaining mechanism 21 by the second housing portion 24 causes release of the engagement between the retaining heads provided at the distal end of the stent and the pockets 22 of the retaining mechanism 21. This, in turn, causes the distal retaining region of the stent to be released completely and thus leads to a complete unfolding of the stent.

Figure 14D:
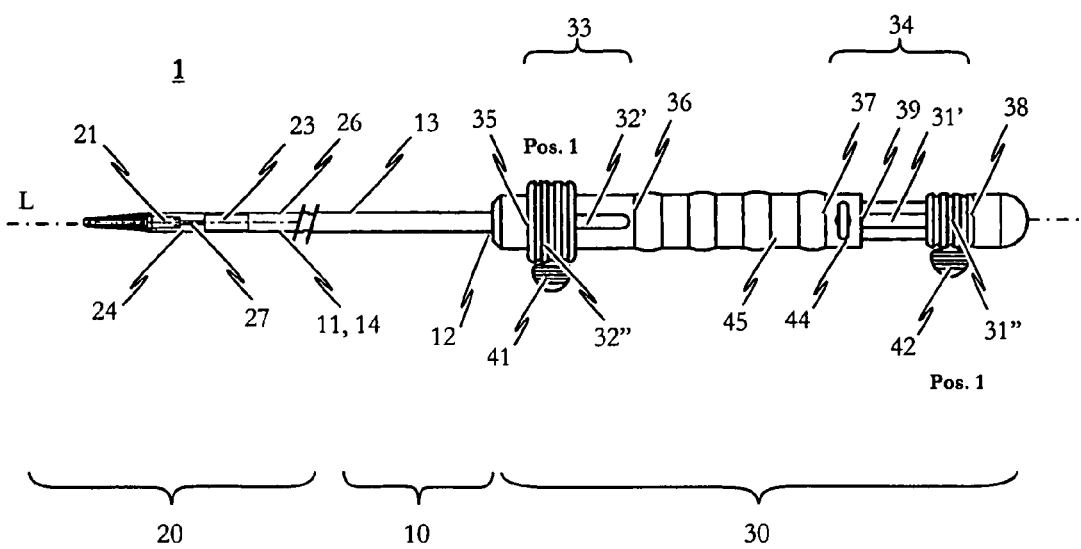

FIGS. 14a to 14d illustrate the insertion system 1 in its four different functional modes described with reference to FIGS. 15a to 15d. However, this time, the diagrams start with the fourth functional mode (FIG. 14a) and then show the third functional mode (FIG. 14b), the second functional mode (FIG. 14c), ending with the first functional mode (FIG. 14d). The sequence illustrated in FIG. 14 is used to load a stent, such as that illustrated in FIG. 17 for example, into the catheter tip 20 of the insertion system 1. The loading procedure, in the steps illustrated in FIGS. 14a to 14d, corresponds to the sequence of the procedure illustrated in FIGS. 15a to 15d but in reverse and is used to remove a stent accommodated in the catheter tip 20 of the insertion system 1. To avoid repetition, reference may be made to the explanations given with respect to FIGS. 15a to 15d.

A preferred embodiment of the retaining mechanism 21 disposed in the catheter tip 20 of the insertion system proposed by the invention will be described in detail below with reference to FIG. 16.

FIG. 16a is a side view showing a preferred embodiment of the retaining mechanism 21. FIG. 16b is a view in cross-section along line A-A indicated in FIG. 16a, illustrating the embodiment of the retaining mechanism 21, whilst FIG. 16c shows a plan view of the distal retaining region 52 of a stent 50 which can be retained in the catheter tip 20 of the insertion system proposed by the invention by means of the retaining mechanism 21 based on the embodiment illustrated in FIG. 16a.

As illustrated, the retaining mechanism 21 has an essentially cylindrical body 21a, the axis of symmetry of which lies on the longitudinal axis L of the catheter tip 20. Several cut-outs or pockets 22—in FIG. 16b three in total—are spaced uniformly apart from one another in the material of the retaining mechanism body 21a, preferably at the proximal end portion of the cylindrical body 21a. These pockets 22 are connected to the proximal-end surface of the cylindrical body 21a by grooves 22b.

The shape and size of the pockets 22a in the material of the body or crown 21a of the retaining mechanism 21 are selected so that a retaining element 55 of the stent 50 complementing the pocket 22a can be accommodated, preferably positively, in each of the pockets 22a. Thus, each retaining element 55 of the stent 50 establishes a releasable engagement with a pocket 22a formed in the crown 21a of the retaining mechanism 21.

As illustrated in FIG. 16c, it is preferable in this respect if the retaining elements 55 of the stent 50 are provided in the form of projecting elements or projecting heads (retaining heads) at the distal end 52 of the stent 50. These retaining elements 55 of the stent 50 in the form of projecting elements are each connected to the positioning arches 54 (and retaining arches 53) of the stent 50 via a neck portion or connecting web 56. When the retaining elements 55 of the stent 50 are positively held in the pockets 22a of the retaining mechanism 21, at least the distal ends of the neck portions 56 lie in the grooves 22b.

Referring to FIG. 15b, the crown 21a of the retaining mechanism 21 is cylindrical, wherein each of the pockets 22a formed in the crown 21a of the retaining mechanism 21 has a shape adapted for substantially accommodating the retaining element 55 provided on the distal region 52 of the stent 50 such that there are no parts of the distal region 52 of the stent 50 protruding from the superficial surface S of the cylindrical crown 21a.

In addition, the crown 21a of the illustrated retaining mechanism 21 comprises snap-on means arranged on the at least one pocket 22a formed in the crown 21a of the retaining mechanism 21 for releasably fixing the retaining element 55 provided on the distal region 52 of the stent 50 in the at least one pocket 22a.

Turning now to FIGS. 17a to 17b, a preferred embodiment of the medical device 100 proposed by the invention will now be described. As illustrated, the medical device 100 has an insertion system 1 designed for transapical access, such as that described in detail above with reference to FIGS. 14 and 15. Naturally, however, it would be conceivable for the medical device to be used with an insertion system designed for transarterial access.

In addition to the insertion system 1, the medical device 100 has a self-expandable heart valve stent 50 accommodated in the catheter tip 20 of the insertion system 1, to which a heart valve prosthesis to be implanted is attached, although this is not explicitly illustrated in FIG. 17. In the first functional mode of the insertion system 1 illustrated in FIG. 17a, the stent 50 has a first pre-definable mode in which it is in a minimised mode. In the implanted mode, on the other hand, the stent 50 is designed to assume a second pre-definable mode in which it is in its expanded configuration.

By using the insertion system 1 described above, the stent 50 is transferred from its first predefined mode into its second predefined mode sequentially on the basis of a pre-definable sequence of events, in steps, during the implantation process.

Specifically, the stent 50 used with the medical device 100 illustrated in FIG. 16 has a proximal anchoring region 51 to which a heart valve prosthesis is attachable. The stent 50 also has a distal retaining region 52 with three retaining elements 55 in the form of retaining heads which can be moved into a releasable engagement with the retaining mechanism 21 of the insertion system 1 and in particular with the pockets 22a formed in the crown 21a of the retaining mechanism 21 of the insertion system 1.

In addition to the proximal anchoring and distal retaining regions 51, 52, the stent 50 also has three first functional components 53 in the form of retaining arches for accommodating the heart valve prosthesis and three second functional components 54 in the form of positioning arches for automatically positioning the stent 50 at the implantation site. The respective positioning arches 54 of the stent 50 are of a functional and structural design such that during the implantation operation and when the stent 50 is in the implanted mode, especially from the point when the insertion system 1 is in the second functional mode, they engage in the pockets of the incumbent heart valve. This being the case, each positioning arch 54 of the stent 50 co-operates with a retaining arch 53, and at the distal region 52 of the stent 50, each end portion 57 of the respective positioning arches 54 is joined to the end portion 58 of the co-operating retaining arch 53.

Specifically, every positioning arch 54 and its co-operating retaining arch 53 of the stent 50 is respectively of an essentially U-shaped or V-shaped structure, which is closed towards the proximal end 51 of the stent 50.

The procedure involved in implanting the stent 50 will now be described in detail with reference to FIGS. 17a to 17b. Specifically, FIG. 17a illustrates the proximal end of a catheter system 10 with the catheter tip 20 and the stent 50 accommodated in the catheter tip 20 with the insertion system 1 in the first functional mode. As already described in connection with FIG. 15a, when the insertion system 1 illustrated in FIG. 17a is in its first functional mode in which the retaining heads 55 of the stent 50 are engaged with the pockets 22a formed in the crown 21a of the retaining mechanism 21 of the catheter tip 20 of the insertion system 1, the retaining arches 53 of the stent with the heart valve prosthesis attached to it are accommodated in the sleeve-shaped first housing portion 23 of the catheter tip 20. When the insertion system 1 is in the first functional mode, the positioning arches 54 of the stent 50 lie between the sleeve-shaped first housing portion 23 and the likewise sleeve-shaped second housing portion 24 of the catheter tip 20. The two housing portions 23 and 24 of the catheter tip 20 are of a mutually telescopic design. Specifically, the sleeve-shaped second housing portion 24 of the catheter tip 20 covers the distal retaining region 52 of the stent 50, the positioning arches 54 of the stent 50 and the sleeve-type first housing portion 23 of the catheter tip 20, in which the proximal anchoring region 51 of the stent 50 with the retaining arches 53 and the heart valve prosthesis 60 (not illustrated in FIG. 17) are accommodated.

As explained above, the material used for the stent is a shape memory material and the shape memory effect and hence the open shape of the stent 50 is triggered by the effect of an external stimulus. By particular preference, this external stimulus is a pre-settable switching temperature which means that the stent material has to be heated to a temperature that is higher than the switching temperature to trigger the shape memory effect and thus restore the memorised open shape of the stent 50. In view of the application for which the medical device 100 is used, it is preferable if the switching temperature is in the range of room temperature and the patient's body temperature. Accordingly, care must be taken when implanting the stent 50 that the stent 50 is appropriately cooled, for example by means of a syringe adapter 43 provided in the handle 30, thereby enabling the catheter system 10 and the catheter tip 20 of the insertion system 1 to be rinsed with an appropriate coolant, such as a salt solution.

In the mode illustrated in FIG. 17a, the catheter tip 20 is fed forwards transapically, i.e. from the heart apex, to the diseased or failing native heart valve.

When the catheter tip 20 with the stent 50 accommodated in the catheter tip 20 has been moved forward to the desired implantation site, cooling is interrupted, as a result of which the stent 50 is heated to the patient's body temperature (36° C.), thereby triggering the shape memory effect of the stent material.

Due to the self-expanding property of the stent 50 triggered as a result, radial forces build up which act on the individual components of the stent 50 and, in particular, on the respective positioning arches 54 and retaining arches 53 of the stent. Since the retaining arches 53 of the stent 50 are still accommodated in the sleeve-type first housing portion 23 of the catheter tip 20 as before, the retaining arches 53 of the stent 50 and the proximal anchoring region 51 of the stent 50 are held in the minimised mode, in spite of the fact that the shape memory effect has been triggered. The positioning arches 54 of the stent 50 and the distal retaining region 52 of the stent 50 are therefore forcibly retained in their folded mode by the sleeve-shaped second housing portion 24.

On reaching the implantation site, the positioning arches 54 of the stent 50 are then released due to an appropriate stepped release of the stent 50 from the insertion system 1. This is done by transferring the insertion system 1 from its first functional mode (see FIG. 15a) to its second functional mode (see FIG. 15b) as described in detail above with reference to FIG. 15a and FIG. 15b, for example and individually illustrated in FIG. 17b. By manipulating the second operating means 34 of the handle 30 used with the insertion system 1, the second housing portion 24 of the catheter tip 20 is moved relative to the retaining mechanism 21 and to the distal retaining region 52 of the stent 50 in the proximal direction, in other words away from the handle. The stroke of the longitudinal movement of the sleeve-type second housing portion 24 effected as a result relative to the retaining mechanism 21 of the catheter tip 20 leads to a situation in which the positioning arches 54 of the stent 50 are no longer surrounded by the sleeve-shaped second housing portion 24 of the catheter tip 20. As a result, the self-expanding property of the positioning arches 54 of the stent 50 opens them due to the radial forces acting in the radial direction. The opened positioning arches 54 of the stent 50 are then positioned in the pockets of the incumbent heart valve. As explained above, the catheter tip 20 of the insertion system 1 can rotate about the longitudinal axis L of the catheter tip 20, which makes positioning of the unfolded positioning arches 54 of the stent 50 in the pockets 70 of the native heart valve easier.

Once the partially expanded stent 50 has been positioned in the pockets of the incumbent heart valve, the insertion system 1 is switched from the second functional mode illustrated in FIG. 17b to the third functional mode. The way in which the insertion system 1 is switched from the second functional mode to the third functional mode was explained in detail above with reference to FIG. 15c. The proximal anchoring region 51 of the stent 50 is released from the first housing portion 23 of the catheter tip 20 when the insertion system 1 is in the third functional mode. The released retaining arches 53 of the stent 50 and the proximal anchoring region 51 of the stent 50, released when the insertion system 1 is in the third functional mode, open due to the radial forces acting in a radial direction and unfold the heart valve prosthesis attached to the retaining arches 53 in the manner of an umbrella.

A check may be made to ensure that the already unfolded heart valve prosthesis is functioning correctly. Once the functioning of the heart valve prosthesis 60 has been checked, the insertion system 1 can then be switched from its third functional mode to its fourth functional mode by another manipulation of the second operating means 34 of the handle 30 of the insertion system 1. The way in which the insertion system 1 is switched to the fourth functional mode was described above with reference to FIG. 15d.

When the second housing portion 24 of the catheter tip 20 is moved further in the proximal direction, in other words away from the handle 30, the distal end portion of the sleeve-type second housing portion 24 of the catheter tip 20 is moved further in the proximal direction so that this distal part of the second housing portion 24 is no longer covering the pockets 22a formed in the crown 21a of the retaining mechanism 21. Accordingly, the hold on the distal retaining region 52 of the stent 50 by the catheter tip 20 is released so that the distal retaining region 52 of the stent 50 also expands in the radial direction, thereby causing the stent 50 to unfold completely.

If, on checking the functioning of the already unfolded heart valve prosthesis in the third functional mode of the insertion system 1, it is ascertained that the implanted heart valve prosthesis is not able to fulfil its function or is not able to do so satisfactorily, or if the stent 50 has not been or can not be optimally positioned at the implantation site, it is possible to switch the insertion system 1 back to the second and then the first functional mode again by moving the co-operating housing portions 23, 24 of the catheter tip 20 in the opposite direction. As a result, the already released and expanded components of the stent 50 can be moved back into the respective housing portions 23, 24 of the catheter tip 20 so that the catheter tip 20 and the stent 50, accommodated in the catheter tip 20 again, can be removed from the patient's body. By returning the stent back into the catheter, damage to vascular system on removal of the stent from the body is minimised.

When the stent 50 has been implanted, the retaining arches 53 of the stent open out in the radial direction, during which the radial forces acting on the retaining arches 53 and also on the distal retaining region 52 of the stent 50 cause the stent 50 to be pressed in a radial direction towards the vessel wall. This provides a reliable anchoring of the stent 50 with the heart valve prosthesis attached to it at the proximal anchoring region 51 at the implantation site and substantially guarantees a reliable seal of the heart valve prosthesis at the proximal anchoring region 51 of the stent 50.

When the heart valve prosthesis is in the implanted mode, the incumbent heart valve is pressed towards the vessel wall due to the self-expanding property of the stent 50. Specifically, the pocket flaps of the insufficient or stenosed heart valve are clamped between the positioning arches 54 and the retaining arches 53 due to the expansion of the stent 50. This permits optimal positioning and stable anchoring of the heart valve prosthesis disposed on the proximal anchoring region 51 of the stent 50.

The above-discussed stent designs, which constitute the basis of the medical device 100 in conjunction with the insertion system 1, are particularly suitable for insertion in a patient's body with minimal invasion using the insertion system 1.

The solution proposed by the invention is distinctive due to an improved insertion system with a stent which can be accommodated in the catheter tip of the insertion system. The stent may be inserted from a transarterial or transapical approach by means of the special insertion system and optimally positioned so that the heart valve prosthesis, stitched to the proximal anchoring region of the stent, can assume the function of the insufficient, narrowed or calcified native heart valve. The radial forces which build up due to the self-expanding property of the stent substantially guarantee a reliable anchoring in the region of the aorta. The catheter system of the insertion system is preferably an 18 to 21F insertion unit, which is compatible with 21F insertion gates and a 0.035"-guide wire. The length of the catheter system should be at least 100 cm in the case of the insertion system designed for transarterial access. The deflecting mechanism which may optionally be provided in the proximal region of the gate system 13 is preferably approximately 30 cm.

The solution proposed by the invention is based on a metal endoprosthesis 1 with a heart valve prosthesis which can be stitched to it or is stitched to it, designed for use in treating diseases of the heart valve which make replacement of the incumbent heart valve necessary. The heart valve stent 1 (endoprosthesis) may be introduced in the inverted position and thus positioned orthotopically in vivo percutaneously and assumes the function of the insufficient or defective native heart valve. The radial forces created due to the self-expanding property of the endoprosthesis 1 substantially guarantee reliable anchoring in the region of the aorta.

A medical instrument comprising an endoprosthesis 1 for positioning and securing a heart valve prosthesis in the aorta of the patient is described, together with an endoprosthesis 1 made from a base of Nitinol as a means of accommodating a heart valve prosthesis for implantation in the body, particularly in the aorta at the site of an aortic heart valve that requires replacement. The ready-to-use medical device proposed by the invention consists of the components comprising the self-expandable Nitinol stent 1 with the valve-supporting segment 20, valve and system for introducing it to the desired site in the body.

In terms of design, the endoprosthesis 1 has three positioning arches for positioning and fixing the medical device in the vessel of the patient and retaining webs for accommodating/attaching the heart valve prosthesis by means of a thread, for example. From a functional point of view, the endoprosthesis 1 exerts high radial forces in its second expanded mode to ensure that the medical device is anchored in the aorta. Eyes 30 are preferably provided on the distal retaining region of the endoprosthesis 1 or medical device, which can be releasably engaged with corresponding components of an introduction catheter system.

The material used to trigger the shape memory effect of the endoprosthesis has a switching temperature between 20° C. and 36° C. and is preferably 22° C. In the cooled state, therefore, the medical device can be introduced into the patient's body by means of a 21F introduction system.

As regards the exact dimensions of the endoprosthesis 1, it is designed to accommodate heart valve prostheses with a valve diameter of 21 mm to 25 mm, in which case the distal retaining region 2 of the endoprosthesis 1 in particular has a diameter that is approximately 10% to 15% bigger than this in order to ensure that the medical device is reliably anchored.

The medical device proposed by the invention has an endoprosthesis which is readily visible by X-ray, which can be achieved by applying markers at the proximal and/or distal region of the endoprosthesis if necessary.

The materials used for the endoprosthesis 1 are materials that have been tried and tested for implantation purposes, for example Nitinol and Tantal. As regards the dimensions of the endoprosthesis, two different stent sizes are currently preferred, which are set out in the table below together with the diameter of the proximal anchoring region and the distal retaining region.

| Stent size | Diameter of the proximal anchoring region | Diameter of the distal retaining region |
| --- | --- | --- |
| Stent No. 1 | 21 to 25 mm | 32 to 34 mm |
| Stent No. 2 | 26 to 31 mm | 35 to 38 mm |

By applying an appropriate finishing treatment, in particular tempering, other dimensions of the stent can be achieved—starting from the two currently preferred stent sizes.

The invention is not restricted to the features described in connection with the preferred embodiments illustrated in the drawings. All combinations of the features described in the specification would be conceivable.

The invention claimed is:

1. A catheter system comprising:
   an endoprosthesis comprising:
     a first portion including a plurality of retaining arches, each retaining arch including a first apex;
     a second portion including a plurality of positioning arches, each positioning arch including a second apex axially aligned with one of the first apices, the first apices and the second apices pointing in a same direction;
     a third portion including a plurality of retaining elements; and
     a heart valve prosthesis directly attached to the plurality of retaining arches; and
   a catheter configured to releasably retain the endoprosthesis in a collapsed state and sequentially release the endoprosthesis from the collapsed state to an expanded state, the catheter comprising:
     a first housing portion for accommodating the first portion of the endoprosthesis;
     a second housing portion for accommodating the second portion of the endoprosthesis;
     a retaining mechanism defining a plurality of pockets formed therein for receiving the plurality of retaining elements of the endoprosthesis; and
     a handle configured to control movement of each of the first housing portion and the second housing portion with respect to the handle;
   wherein the first housing portion and the second housing portion are arranged relative to one another such that movement of the second housing portion in a first direction relative to the endoprosthesis, before movement of the first housing portion relative to the endoprosthesis, uncovers the second portion of the endoprosthesis from the catheter while the first portion of the endoprosthesis is accommodated within the first housing portion and the plurality of retaining elements of the endoprosthesis remains engaged with the plurality of pockets of the retaining mechanism and accommodated within the second housing portion;

wherein the second housing portion is further movable in the first direction to uncover and release the plurality of retaining elements of the endoprosthesis from the retaining mechanism; and wherein the handle includes:
a first slidable element movable with respect to a remainder of the handle along a fixed axial stroke length between first and second limits; and
a second slidable element movable with respect to a remainder of the handle along a fixed axial stroke length between third and fourth limits;
wherein each of the first and second limits has a different axial position than an axial position of the third limit.

2. The catheter system of claim 1, wherein the handle is configured to move the second housing portion with respect to the first housing portion to uncover the second portion of the endoprosthesis while selectively retaining the first portion of the endoprosthesis.

3. The catheter system of claim 2, wherein the first slidable element is coupled to the first housing portion to effect a pre-definable longitudinal displacement of the first housing portion relative to the handle and relative to the endoprosthesis, and wherein the second slidable element is coupled to the second housing portion to effect a pre-definable displacement of the second housing portion relative to the handle and relative to the endoprosthesis.

4. The catheter system of claim 1, wherein both the first housing portion and the second housing portion comprise sleeve elements.

5. The catheter system of claim 1, wherein the first housing portion is movable in a second direction towards the handle of the catheter to uncover the first portion of the endoprosthesis.

6. The catheter system of claim 5, wherein movement of the second slidable element in the first direction corresponds to movement of the second housing portion in the first direction to completely uncover the second portion of the endoprosthesis from the catheter system, and movement of the first slidable element in the second direction corresponds to movement of the first housing portion in the second direction to uncover the first portion of the endoprosthesis.

7. The catheter system of claim 1, wherein the first and second housing portions are arranged telescopically.

8. The catheter system of claim 1, wherein the plurality of pockets of the retaining mechanism includes exactly three pockets having a shape complementary to three retaining elements of the plurality of retaining elements for receiving the three retaining elements.

9. The catheter system of claim 8, wherein the retaining mechanism defines three longitudinal grooves, each groove extending from a corresponding pocket of the plurality of pockets to an end of the retaining mechanism, each groove having a shape complementary to a longitudinal strut portion of a retaining element of the plurality of retaining elements.

10. The catheter system of claim 8, wherein the three pockets are uniformly spaced apart around a circumference of the retaining mechanism, and wherein the retaining mechanism defines three longitudinal grooves, each groove extending from a corresponding pocket to an end of the retaining mechanism, each groove having a shape complementary to a longitudinal strut portion of a retaining element of the endoprosthesis.

11. The catheter system of claim 1, wherein the handle includes a locking element.

12. The catheter system of claim 11, configured to reversibly load and release the endoprosthesis from the catheter system.

13. A catheter system for implanting an endoprosthesis having a plurality of positioning arches, a plurality of retaining arches, and a body portion having a plurality of retaining elements, the catheter system comprising:
a catheter including:
a retaining portion configured to selectively fix the endoprosthesis to the catheter, the retaining portion defining a plurality of pockets formed therein, the plurality of pockets having a shape complementary to the plurality of retaining elements of the endoprosthesis;
a first housing portion configured to selectively retain the plurality of retaining arches in a collapsed state; and
a second housing portion configured to selectively retain the plurality of positioning arches and the body portion in a collapsed state; and
the endoprosthesis, wherein the endoprosthesis includes a heart valve prosthesis directly attached to the plurality of retaining arches, each retaining arch including an apex axially aligned with an apex of a corresponding positioning arch of the plurality of positioning arches and pointing in a same direction as the apex of the corresponding positioning arch;
wherein the first housing portion and the second housing portion are arranged relative to one another such that movement of the second housing portion relative to the endoprosthesis and the retaining portion, before movement of the first housing portion relative to the endoprosthesis and the retaining portion, uncovers the plurality of positioning arches from the catheter while the plurality of retaining arches are retained by the first housing portion and the plurality of retaining elements are retained by the second housing portion.

14. The catheter system of claim 13, wherein the catheter includes a handle, and wherein:
a second operation of the handle moves the first housing portion in a first direction with respect to the retaining portion to uncover the plurality of retaining arches of the endoprosthesis; and
a first operation of the handle moves the second housing portion in a second direction of the catheter, opposite the first direction, with respect to the retaining portion to uncover the plurality of positioning arches of the endoprosthesis.

15. The catheter system of claim 14, wherein the handle includes a first slidable element movable with respect to the handle along a fixed stroke length between first and second limits, and a locking element selectively resisting movement of the first slidable element, wherein the second operation of the handle includes moving the first slidable element along a longitudinal axis of the handle.

16. The catheter system of claim 15, wherein the handle includes a second slidable element movable with respect to the handle along a fixed stroke length between third and fourth limits, wherein the first operation of the handle includes moving the second slidable element along a longitudinal axis of the handle, and wherein each of the first and second limits has a different axial position than an axial position of the third limit.

17. The catheter system of claim 16, wherein the first operation of the handle moves the second housing portion towards a tip of the catheter.

18. The catheter system of claim 15, wherein the second operation of the handle moves the first housing portion towards the handle.

19. The catheter system of claim 13, wherein movement of the second housing portion relative to the endoprosthesis and the retaining portion, before movement of the first housing portion relative to the endoprosthesis and the retaining portion, in a second direction permits the plurality of positioning arches of the endoprosthesis to expand such that the plurality of positioning arches pivot relative to the plurality of retaining arches of the endoprosthesis, and wherein further movement of the second housing portion in the second direction releases the plurality of retaining elements of the endoprosthesis from the plurality of pockets of the retaining portion.

20. The catheter system of claim 19, wherein the plurality of retaining elements are released from the plurality of pockets as a function of the body portion of the endoprosthesis expanding from the collapsed state to an expanded state.

21. The catheter system of claim 19, wherein movement of the first housing portion in a first direction opposite the second direction and with respect to the retaining portion releases the plurality of retaining arches from the collapsed state to an expanded state after the plurality of positioning arches are uncovered and while the plurality of retaining elements of the endoprosthesis remain disposed within the plurality of pockets of the retaining portion.

22. The catheter system of claim 13, wherein the endoprosthesis is configured to clip a flap of a native heart valve between each positioning arch and retaining arch.

23. The catheter system of claim 13, wherein the retaining portion of the catheter is configured to accommodate a portion of the endoprosthesis to which the heart valve prosthesis is not attached.

24. The catheter system of claim 13, wherein the retaining portion defines a plurality of longitudinal grooves each having a cross-sectional dimension smaller than a cross-sectional dimension of each of the plurality of pockets, each groove extending from a corresponding pocket of the plurality of pockets to an end of the retaining portion, each groove having a shape complementary to a longitudinal strut portion of a retaining element of the plurality of retaining elements of the endoprosthesis.

25. A catheter system comprising:
an endoprosthesis comprising:
  a plurality of first arches;
  a plurality of second arches, each second arch pointing in a same direction as the plurality of first arches;
  a plurality of connecting struts parallel to a longitudinal axis of the endoprosthesis when the endoprosthesis is in a collapsed state, wherein each connecting strut connects a pair of adjacent first arches at a first axial location and a pair of adjacent second arches at a second axial location different from the first axial location;
  a plurality of retaining elements; and
  a heart valve prosthesis directly attached to the plurality of second arches;
a catheter including a tip portion at a first end of the catheter and a handle portion at a second end of the catheter configured to sequentially release the endoprosthesis from the collapsed state to an expanded state, the tip portion including:
  a first sleeve element selectively surrounding the first arches of the endoprosthesis and the plurality of retaining elements of the endoprosthesis;
  a second sleeve element selectively surrounding the second arches of the endoprosthesis, and
  a retaining mechanism defining a plurality of pockets formed therein for receiving the plurality of retaining elements of the endoprosthesis;
wherein the handle portion is configured to manipulate the tip portion to sequentially release the endoprosthesis by:
  a first movement of the first sleeve element in a first direction relative to the retaining mechanism to completely uncover the first arches of the endoprosthesis from the catheter while the second arches are covered by the second sleeve element,
  a second movement of the second sleeve element in a second direction, opposite the first direction, relative to the retaining mechanism to uncover the second arches of the endoprosthesis after the first movement, and
  a third movement of the first sleeve element further in the first direction to uncover the plurality of retaining elements of the endoprosthesis after the second movement.

26. The catheter system of claim 25, wherein each pocket has a curved circumference to match a convex head portion of one of the retaining elements of the endoprosthesis.

27. The catheter system of claim 25, wherein the retaining mechanism is configured to accommodate a portion of the endoprosthesis to which the heart valve prosthesis is not attached.

28. The catheter system of claim 25, wherein the retaining mechanism defines a plurality of longitudinal grooves, each groove extending from a pocket of the plurality of pockets to an end of the retaining mechanism, each groove having a shape complementary to a longitudinal strut portion of a retaining element of the plurality of retaining elements of the endoprosthesis.

29. A catheter system, comprising:
a catheter including a tip portion at a first end of the catheter for sequentially releasing an endoprosthesis from a collapsed state to an expanded state, and a handle portion at a second end of the catheter, opposite the first end, for sequentially manipulating the tip portion; and
the endoprosthesis including a plurality of positioning arches having respective apices projecting toward the handle portion when the endoprosthesis is in the collapsed state, a plurality of retaining arches having respective apices projecting toward the handle portion when the endoprosthesis is in the collapsed state, each apex of a positioning arch being axially aligned with a corresponding apex of one of the retaining arches, wherein the apices of the plurality of the retaining arches define a proximal-most end of the endoprosthesis, and three retaining elements disposed closer to a tip of the catheter than the positioning arches and the retaining arches when the endoprosthesis is in the collapsed state;
wherein the tip portion of the catheter includes:
  a first sleeve element surrounding the plurality of positioning arches and the plurality of retaining elements of the endoprosthesis when the endoprosthesis is in the collapsed state,
  a second sleeve element surrounding the plurality of retaining arches of the endoprosthesis when the endoprosthesis is in the collapsed state, and a retaining portion defining three pockets formed therein for receiving head portions of the three retaining elements of the endoprosthesis to fix the location of the endoprosthesis relative to the handle portion and the tip portion of the catheter;

wherein a first manipulation of the handle portion moves the first sleeve element away from the handle portion to uncover the plurality of positioning arches of the endoprosthesis, thereby permitting the positioning arches to expand while the retaining portion and the second sleeve element remain stationary relative to the endoprosthesis, the second sleeve element surrounding the plurality of retaining arches of the endoprosthesis to retain the plurality of retaining arches in the collapsed state; and wherein a second manipulation of the handle portion, separate from the first manipulation, moves the second sleeve element toward the handle portion to uncover the plurality of retaining arches of the endoprosthesis, thereby permitting the retaining arches of the endoprosthesis to expand while the first sleeve element surrounds the exactly three retaining elements of the endoprosthesis.

30. The catheter system of claim 29, wherein a third manipulation of the handle portion moves the first sleeve element away from the handle portion to uncover the exactly three retaining elements of the endoprosthesis, thereby permitting the retaining elements to expand.

31. The catheter system of claim 30, wherein the first manipulation occurs before the second and third manipulations and the second manipulation occurs before the third manipulation.

32. The catheter system of claim 30, wherein the catheter includes a first slidable element operatively connected to the first sleeve element and movable with respect to the handle portion, wherein the third manipulation of the handle portion moves the first slidable element along a longitudinal axis of the catheter.

33. The catheter system of claim 29, wherein the first manipulation occurs before the second manipulation.

34. The catheter system of claim 29, wherein the handle portion includes a mechanism limiting movement of the first sleeve during the first manipulation.

35. The catheter system of claim 29, wherein the catheter includes a first slidable element operatively connected to the first sleeve element and movable with respect to the handle portion, wherein the first manipulation of the handle portion moves the first slidable element along a longitudinal axis of the catheter.

36. The catheter system of claim 35, wherein the catheter includes a second slidable element operatively connected to the second sleeve element and movable with respect to the handle portion, wherein the second manipulation of the handle portion moves the second slidable element along the longitudinal axis of the catheter.

37. The catheter system of claim 29, wherein the plurality of retaining arches includes three retaining arches and the plurality of positioning arches includes three positioning arches.

38. The catheter system of claim 37, wherein the endoprosthesis is configured to clip a flap of a native heart valve between each positioning arch and retaining arch.

* * * * *